(12) United States Patent
Frank et al.

(10) Patent No.: US 11,154,203 B2
(45) Date of Patent: Oct. 26, 2021

(54) DETECTING FEVER FROM IMAGES AND TEMPERATURES

(71) Applicant: Facense Ltd., Kiryat Tivon (IL)

(72) Inventors: Ari M Frank, Haifa (IL); Arie Tzvieli, Berkeley, CA (US); Ori Tzvieli, Berkeley, CA (US); Gil Thieberger, Kiryat Tivon (IL)

(73) Assignee: Facense Ltd., Kiryat Tivon (IL)

( * ) Notice: Subject to any disclaimer, the term of this patent is extended or adjusted under 35 U.S.C. 154(b) by 0 days.

(21) Appl. No.: 17/009,655

(22) Filed: Sep. 1, 2020

(65) Prior Publication Data

US 2020/0397306 A1    Dec. 24, 2020

Related U.S. Application Data

(63) Continuation-in-part of application No. 17/005,259, filed on Aug. 27, 2020, which is a
(Continued)

(51) Int. Cl.
*A61B 5/00* (2006.01)
*A61B 5/01* (2006.01)
(Continued)

(52) U.S. Cl.
CPC ............ *A61B 5/015* (2013.01); *A61B 5/0075* (2013.01); *A61B 5/165* (2013.01); *A61B 5/6803* (2013.01);
(Continued)

(58) Field of Classification Search
CPC . A61B 90/361; A61B 5/02438; A61B 5/0245; A61B 5/14542; A61B 5/02405;
(Continued)

(56) References Cited

U.S. PATENT DOCUMENTS 5,757,002 A    5/1998    Yamasaki et al.
5,842,979 A *  12/1998   Jarman .............. A61B 5/14552
                                              600/322
(Continued)

FOREIGN PATENT DOCUMENTS

EP         2087802 A2 *  8/2009   ........... A42B 3/0433
WO    WO2019181150 A1    9/2019

OTHER PUBLICATIONS

Ahn, J. M. (2017). New aging index using signal features of both photoplethysmograms and acceleration plethysmograms. Healthcare informatics research, 23(1), 53-59.
(Continued)

*Primary Examiner* — Gail Kaplan Verbitsky
(74) *Attorney, Agent, or Firm* — Active Knowledge Ltd.

(57) ABSTRACT

Described herein are embodiments of systems and methods that utilize temperature measurements taken with head-mounted sensors as well as images of a user's face to detect fever and/or intoxication. One embodiment of a system to detect fever includes a first head-mounted temperature sensor that measures skin temperature ($T_{skin}$) at a first region on a user's head, a second head-mounted temperature sensor that measures a temperature of the environment ($T_{env}$), and a computer. The computer receives images of a second region on the user's face, captured by a camera sensitive to wavelengths below 1050 nanometer, and calculates, based on the images, values indicative of hemoglobin concentrations at three or more regions on the user's face. The computer can then detect whether the user has a fever based on $T_{skin}$, $T_{env}$ and the values.

20 Claims, 18 Drawing Sheets

Related U.S. Application Data continuation-in-part of application No. 16/854,883, filed on Apr. 21, 2020, now Pat. No. 10,813,559, and a continuation-in-part of application No. 16/689,929, filed on Nov. 20, 2019, now Pat. No. 11,064,892, and a continuation-in-part of application No. 16/689,959, filed on Nov. 20, 2019, now Pat. No. 10,799,122, which is a continuation-in-part of application No. 16/453,993, filed on Jun. 26, 2019, now Pat. No. 10,667,697, which is a continuation-in-part of application No. 16/831,413, filed on Mar. 26, 2020, now Pat. No. 10,791,938, which is a continuation-in-part of application No. 16/551,654, filed on Aug. 26, 2019, now Pat. No. 10,638,938, which is a continuation-in-part of application No. 16/453,993, filed on Jun. 26, 2019, now Pat. No. 10,667,697, which is a continuation-in-part of application No. 16/375,841, filed on Apr. 4, 2019, now Pat. No. 10,376,163, which is a continuation-in-part of application No. 16/156,493, filed on Oct. 10, 2018, now Pat. No. 10,524,667, which is a continuation-in-part of application No. 15/635,178, filed on Jun. 27, 2017, now Pat. No. 10,136,856, and a continuation-in-part of application No. 15/231,276, filed on Aug. 8, 2016, now abandoned, and a continuation-in-part of application No. 15/832,855, filed on Dec. 6, 2017, now Pat. No. 10,130,308, which is a continuation-in-part of application No. 15/182,592, filed on Jun. 14, 2016, now Pat. No. 10,165,949, and a continuation-in-part of application No. 15/231,276, filed on Aug. 8, 2016, now abandoned, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017, now Pat. No. 10,523,852, and a continuation-in-part of application No. 15/182,566, filed on Jun. 14, 2016, now Pat. No. 9,867,546, which is a continuation-in-part of application No. 15/833,115, filed on Dec. 6, 2017, now Pat. No. 10,130,261, which is a continuation-in-part of application No. 15/182,592, filed on Jun. 14, 2016, now Pat. No. 10,165,949, and a continuation-in-part of application No. 15/231,276, filed on Aug. 8, 2016, now abandoned, and a continuation-in-part of application No. 15/284,528, filed on Oct. 3, 2016, now Pat. No. 10,113,913, and a continuation-in-part of application No. 15/635,178, filed on Jun. 27, 2017, now Pat. No. 10,136,856, and a continuation-in-part of application No. 15/722,434, filed on Oct. 2, 2017, now Pat. No. 10,523,852, which is a continuation-in-part of application No. 16/147,695, filed on Sep. 29, 2018, now Pat. No. 10,376,153, which is a continuation of application No. 15/182,592, filed on Jun. 14, 2016, now Pat. No. 10,165,949, which is a continuation-in-part of application No. 16/156,586, filed on Oct. 10, 2018, now Pat. No. 10,524,696, which is a continuation-in-part of application No. 15/832,815, filed on Dec. 6, 2017, now Pat. No. 10,136,852, and a continuation-in-part of application No. 15/859,772, filed on Jan. 2, 2018, now Pat. No. 10,159,411.

(60) Provisional application No. 63/048,638, filed on Jul. 6, 2020, provisional application No. 63/024,471, filed on May 13, 2020, provisional application No. 63/006,827, filed on Apr. 8, 2020, provisional application No. 62/960,913, filed on Jan. 14, 2020, provisional application No. 62/945,141, filed on Dec. 7, 2019, provisional application No. 62/928,726, filed on Oct. 31, 2019, provisional application No. 62/722,655, filed on Aug. 24, 2018, provisional application No. 62/354,833, filed on Jun. 27, 2016, provisional application No. 62/372,063, filed on Aug. 8, 2016, provisional application No. 62/652,348, filed on Apr. 4, 2018, provisional application No. 62/667,453, filed on May 5, 2018, provisional application No. 62/202,808, filed on Aug. 8, 2015, provisional application No. 62/236,868, filed on Oct. 3, 2015, provisional application No. 62/456,105, filed on Feb. 7, 2017, provisional application No. 62/480,496, filed on Apr. 2, 2017, provisional application No. 62/566,572, filed on Oct. 2, 2017, provisional application No. 62/175,319, filed on Jun. 14, 2015, provisional application No. 62/202,808, filed on Aug. 8, 2015, provisional application No. 62/175,319, filed on Jun. 14, 2015, provisional application No. 62/202,808, filed on Aug. 8, 2015, provisional application No. 62/236,868, filed on Oct. 3, 2015, provisional application No. 62/354,833, filed on Jun. 27, 2016, provisional application No. 62/372,063, filed on Aug. 8, 2016, provisional application No. 62/175,319, filed on Jun. 14, 2015, provisional application No. 62/202,808, filed on Aug. 8, 2015, provisional application No. 62/456,105, filed on Feb. 7, 2017, provisional application No. 62/480,496, filed on Apr. 2, 2017, provisional application No. 62/566,572, filed on Oct. 2, 2017.

(51) Int. Cl.
*G01J 5/12* (2006.01)
*G01J 5/02* (2006.01)
*A61B 5/16* (2006.01)
*G01J 5/00* (2006.01)

(52) U.S. Cl.
CPC .......... *A61B 5/6814* (2013.01); *A61B 5/7282* (2013.01); *A61B 5/748* (2013.01); *G01J 5/0265* (2013.01); *G01J 5/12* (2013.01); *A61B 5/0077* (2013.01); *A61B 2562/0271* (2013.01); *A61B 2562/0276* (2013.01); *A61B 2576/00* (2013.01); *G01J 2005/0077* (2013.01); *G01J 2005/0085* (2013.01)

(58) Field of Classification Search
CPC ....... A61B 5/333; A61B 5/015; A61B 5/0075; A61B 5/6803; A61B 5/6814; A61B 5/748; A61B 5/077; A61B 2562/0271; A61B 2562/0276; A61B 2576/00; A61B 5/0077; A61B 5/01; A61B 5/4884; A61B 5/024; A61B 5/0878; A61B 5/1128; A61B 5/11; A61B 5/0008; A61B 5/14535; A61B 5/1477; G16H 5/20; G16H 5/30; G16H 10/60; G01N 2021/6419; G01N 2021/6493; G01N 2033/4975; G01N 21/6458; G01N 21/6486; G01N 33/0036; G01N 33/497; G01N 33/50; G01N 33/5097; G01J 5/0025; G01J 2005/0077; G01J 2005/0085; G01J 2005/0081; G01J 3/0272; G01J 5/0265; G01J 5/12
See application file for complete search history.

(56) References Cited

U.S. PATENT DOCUMENTS

| | | | |
|---|---|---|---|
| 6,255,650 B1* | 7/2001 | Warner | G02B 23/125 250/330 |
| 6,819,950 B2 | 11/2004 | Mills | |
| 6,995,665 B2* | 2/2006 | Appelt | G08B 21/02 128/204.23 |
| 7,111,980 B2* | 9/2006 | Pavlidis | A61B 5/015 374/45 |
| 7,384,395 B2 | 6/2008 | Hatlestsad et al. | |
| 8,085,144 B2* | 12/2011 | Appelt | A62B 18/08 340/539.11 |
| 8,109,882 B2* | 2/2012 | Baker, Jr. | A61B 5/6814 600/500 |
| 8,175,670 B2 | 5/2012 | Baker, Jr. et al. | |
| 8,251,903 B2 | 8/2012 | LeBoeuf et al. | |
| 8,328,420 B2* | 12/2012 | Abreu | A61B 5/01 374/208 |
| 8,512,253 B2 | 8/2013 | Reichman et al. | |
| 8,617,081 B2 | 12/2013 | Mestha et al. | |
| 8,768,424 B2 | 7/2014 | Crowe et al. | |
| 8,768,438 B2 | 7/2014 | Mestha et al. | |
| 8,855,384 B2 | 10/2014 | Kyal et al. | |
| 8,977,347 B2 | 3/2015 | Mestha et al. | |
| 9,020,185 B2 | 4/2015 | Mestha et al. | |
| 9,044,180 B2 | 6/2015 | LeBoeuf et al. | |
| 9,220,856 B2 | 12/2015 | Martin et al. | |
| 9,355,356 B2* | 5/2016 | Weast | G06F 3/011 |
| 9,414,769 B2 | 8/2016 | Karst et al. | |
| 9,489,817 B2 | 11/2016 | Gui | |
| 9,610,035 B2 | 4/2017 | Aarts et al. | |
| 9,805,475 B2 | 10/2017 | Rubinstein et al. | |
| 9,808,204 B2 | 11/2017 | LeBoeuf et al. | |
| 9,848,780 B1 | 12/2017 | DeBusschere et al. | |
| 9,940,710 B2 | 4/2018 | Watanabe | |
| 9,980,650 B2 | 5/2018 | Bezemer | |
| 10,070,796 B2* | 9/2018 | Ostroverkhov | A61B 5/6815 |
| 10,152,869 B2 | 12/2018 | Peyrard | |
| 10,216,981 B2 | 2/2019 | Tzvieli et al. | |
| 10,317,672 B2 | 6/2019 | Sarkar | |
| 10,349,887 B1 | 7/2019 | Tzvieli et al. | |
| 10,376,163 B1 | 8/2019 | Tzvieli et al. | |
| 10,506,960 B2 | 12/2019 | Kaestle | |
| 10,638,938 B1 | 5/2020 | Tzvieli et al. | |
| 10,791,938 B2 | 10/2020 | Tzvieli et al. | |
| 10,799,122 B2 | 10/2020 | Tzvieli et al. | |
| 2004/0004547 A1* | 1/2004 | Appelt | G08B 21/182 340/573.1 |
| 2005/0001728 A1* | 1/2005 | Appelt | G08B 21/182 340/573.1 |
| 2005/0159055 A1* | 7/2005 | Nakase | B63C 9/1255 441/106 |
| 2005/0271117 A1* | 12/2005 | Grassl | G01J 5/10 374/121 |
| 2007/0276632 A1 | 11/2007 | Banet et al. | |
| 2009/0018407 A1* | 1/2009 | Jung | A61B 5/4076 600/301 |
| 2009/0182688 A1 | 7/2009 | van der Zwan et al. | |
| 2010/0241011 A1 | 9/2010 | McCombie et al. | |
| 2012/0022349 A1 | 1/2012 | Poupko et al. | |
| 2012/0029320 A1 | 2/2012 | Watson et al. | |
| 2013/0215244 A1 | 8/2013 | Mestha et al. | |
| 2014/0095209 A1* | 4/2014 | Molny | G06F 19/00 705/3 |
| 2014/0213917 A1 | 7/2014 | Hobeika et al. | |
| 2014/0303690 A2* | 10/2014 | Agro | A61N 1/38 607/62 |
| 2015/0005646 A1 | 1/2015 | Balakrishnan et al. | |
| 2015/0099946 A1* | 4/2015 | Sahin | G16H 50/20 600/301 |
| 2015/0112606 A1 | 4/2015 | He et al. | |
| 2015/0297126 A1 | 10/2015 | Atsumori et al. | |
| 2016/0007899 A1* | 1/2016 | Durkee | A61B 5/7267 600/544 |
| 2016/0007935 A1 | 1/2016 | Hernandez et al. | |
| 2016/0022157 A1 | 1/2016 | Melker et al. | |
| 2016/0070122 A1 | 3/2016 | Sales et al. | |
| 2016/0098592 A1 | 4/2016 | Lee et al. | |
| 2016/0120411 A1 | 5/2016 | Hadley et al. | |
| 2016/0167672 A1 | 6/2016 | Krueger | |
| 2016/0206216 A1 | 7/2016 | Kirenko | |
| 2016/0296124 A1 | 10/2016 | Wegerich et al. | |
| 2016/0302677 A1 | 10/2016 | He | |
| 2017/0007167 A1 | 1/2017 | Kostic et al. | |
| 2017/0011210 A1 | 1/2017 | Cheong et al. | |
| 2017/0039881 A1* | 2/2017 | Belch | G06K 9/00342 |
| 2017/0095157 A1 | 4/2017 | Frank | |
| 2017/0112376 A1 | 4/2017 | Gill et al. | |
| 2017/0202505 A1 | 7/2017 | Kirenko et al. | |
| 2017/0231490 A1 | 8/2017 | Toth et al. | |
| 2017/0367590 A1 | 12/2017 | Sebe et al. | |
| 2017/0367651 A1 | 12/2017 | Tzvieli et al. | |
| 2018/0031372 A1 | 2/2018 | Gill | |
| 2018/0042486 A1 | 2/2018 | Yoshizawa et al. | |
| 2018/0146870 A1 | 5/2018 | Shemesh et al. | |
| 2018/0177416 A1 | 6/2018 | Church et al. | |
| 2018/0192950 A1 | 7/2018 | LeBoeuf et al. | |
| 2018/0199870 A1 | 7/2018 | Lee et al. | |
| 2018/0206733 A1 | 7/2018 | Kasan et al. | |
| 2018/0206735 A1 | 7/2018 | Holz et al. | |
| 2018/0210547 A1 | 7/2018 | Sarkar | |
| 2018/0214079 A1 | 8/2018 | Banet et al. | |
| 2018/0279893 A1* | 10/2018 | McDuff | A61B 5/02427 |
| 2018/0314879 A1 | 11/2018 | Khwaja et al. | |
| 2019/0021615 A1 | 1/2019 | Rundo et al. | |
| 2019/0037834 A1* | 2/2019 | Yoshida | A01N 1/0294 |
| 2019/0117096 A1 | 4/2019 | Rundo et al. | |
| 2019/0159735 A1 | 5/2019 | Rundo et al. | |
| 2019/0174039 A1 | 6/2019 | Jung et al. | |
| 2019/0196179 A1 | 6/2019 | Sarkar et al. | |
| 2019/0204912 A1 | 7/2019 | Yang et al. | |
| 2019/0216340 A1 | 7/2019 | Holz et al. | |
| 2019/0269353 A1* | 9/2019 | Venkatraman | A61B 5/744 |
| 2019/0313914 A1 | 10/2019 | Kirenko et al. | |
| 2019/0313915 A1 | 10/2019 | Tzvieli et al. | |
| 2019/0320984 A1* | 10/2019 | Elliott | A61B 5/02225 |
| 2020/0156648 A1 | 5/2020 | Zhang et al. | |
| 2020/0192089 A1* | 6/2020 | Haddick | G06F 3/016 |
| 2020/0225760 A1* | 7/2020 | Ofir | A61B 5/11 |
| 2020/0285069 A1* | 9/2020 | Villalpando | G02C 11/06 |
| 2020/0337631 A1* | 10/2020 | Sahin | A61B 5/1123 |
| 2021/0012549 A1* | 1/2021 | Comer | G06K 9/00288 |
| 2021/0105456 A1* | 4/2021 | Edwin | G06F 3/0346 |

OTHER PUBLICATIONS

Alghoul, K., Alharthi, S., Al Osman, H., & El Saddik, A. (2017). Heart rate variability extraction from videos signals: ICA vs. EVM comparison. IEEE Access, 5, 4711-4719.

Allen, J. (2007). Photoplethysmography and its application in clinical physiological measurement. Physiological measurement, 28(3), R1.

Al-Naji, A., Gibson, K., Lee, S. H., & Chahl, J. (2017). Monitoring of cardiorespiratory signal: Principles of remote measurements and review of methods. IEEE Access, 5, 15776-15790.

Alzahrani, A., Hu, S., Azorin-Peris, V., Barrett, L., Esliger, D., Hayes, M., . . . & Kuoch, S. (2015). A multi-channel opto-electronic sensor to accurately monitor heart rate against motion artefact during exercise. Sensors, 15(10), 25681-25702.

Avolio, A. P., Butlin, M., & Walsh, A. (2009). Arterial blood pressure measurement and pulse wave analysis—their role in enhancing cardiovascular assessment. Physiological measurement, 31(1), R1.

Ballinger, B., Hsieh, J., Singh, A., Sohoni, N., Wang, J., Tison, G. H., . . . & Pletcher, M. J. (Apr. 2018). DeepHeart: semi-supervised sequence learning for cardiovascular risk prediction. In Thirty-Second AAAI Conference on Artificial Intelligence.

Birrenkott, D. A., Pimentel, M. A., Watkinson, P. J., & Clifton, D. A. (Aug. 2016). Robust estimation of respiratory rate via ECG-and PPG-derived respiratory quality indices. In 2016 38th Annual International Conference of the IEEE Engineering in Medicine and Biology Society (EMBC) (pp. 676-679). IEEE.

(56) References Cited

OTHER PUBLICATIONS

Buxi, D., Redoute, J. M., & Yuce, M. R. (2015). A survey on signals and systems in ambulatory blood pressure monitoring using pulse transit time. Physiological measurement, 36(3), R1.

Callego, E. C., & de Haan, G. (Mar. 2015). Automatic ROI for remote photoplethysmography using PPG and color features. In 10th International Conference on Computer Vision Theory and Applications VISAPP—2015.

Castaneda, D., Esparza, A., Ghamari, M., Soltanpur, C., & Nazeran, H. (2018). A review on wearable photoplethysmography sensors and their potential future applications in health care. International journal of biosensors & bioelectronics, 4(4), 195.

Charlton, P. H., Celka, P., Farukh, B., Chowienczyk, P., & Alastruey, J. (2018). Assessing mental stress from the photoplethysmogram: a numerical study. Physiological measurement, 39(5), 054001.

Constant, N., Douglas-Prawl, O., Johnson, S., & Mankodiya, K. (Jun. 2015). Pulse—Glasses: An unobtrusive, wearable HR monitor with Internet-of-Things functionality. In 2015 IEEE 12th International Conference on Wearable and Implantable Body Sensor Networks (BSN) (pp. 1-5). IEEE.

Corral, F., Paez, G., & Strojnik, M. (2014). A photoplethysmographic imaging system with supplementary capabilities. Optica Applicata, 44(2).

Ding, X. R., Zhao, N., Yang, G. Z., Pettigrew, R. I., Lo, B., Miao, F., . . . & Zhang, Y. T. (2016). Continuous blood pressure measurement from invasive to unobtrusive: celebration of 200th birth anniversary of Carl Ludwig. IEEE journal of biomedical and health informatics, 20(6), 1455-1465.

Elgendi, M. (2012). On the analysis of fingertip photoplethysmogram signals. Current cardiology reviews, 8(1), 14-25.

Escobar Restrepo, B., Torres Villa, R., & Kyriacou, P. (2018). Evaluation of the Linear Relationship Between Pulse Arrival Time and Blood Pressure in ICU Patients: Potential and Limitations. Frontiers in physiology, 9, 1848.

Fallet, S., Schoenenberger, Y., Martin, L., Braun, F., Moser, V., & Vesin, J. M. (Sep. 2017). Imaging photoplethysmography: A real-time signal quality index. In 2017 Computing in Cardiology (CinC) (pp. 1-4). IEEE.

Feng, L., Po, L. M., Xu, X., Li, Y., Cheung, C. H., Cheung, K. W., & Yuan, F. (Apr. 2015). Dynamic ROI based on K-means for remote photoplethysmography. In 2015 IEEE International Conference on Acoustics, Speech and Signal Processing (ICASSP) (pp. 1310-1314). IEEE.

Flament, F., Francois, G., Qiu, H., Ye, C., Hanaya, T., Batisse, D., . . . & Bazin, R. (2015). Facial skin pores: a multiethnic study. Clinical, cosmetic and investigational dermatology, 8, 85.

Fung, P., Dumont, G., Ries, C., Mott, C., & Ansermino, M. (Sep. 2004). Continuous noninvasive blood pressure measurement by pulse transit time. In The 26th annual international conference of the IEEE engineering in medicine and biology society (vol. 1, pp. 738-741). IEEE.

Holton, B. D., Mannapperuma, K., Lesniewski, P. J., & Thomas, J. C. (2013). Signal recovery in imaging photoplethysmography. Physiological measurement, 34(11), 1499.

Holz, C., & Wang, E. J. (2017). Glabella: Continuously sensing blood pressure behavior using an unobtrusive wearable device. Proceedings of the ACM on Interactive, Mobile, Wearable and Ubiquitous Technologies, 1(3), 58.

Huang, P. W., Lin, C. H., Chung, M. L., Lin, T. M., & Wu, B. F. (Nov. 2017). Image based contactless blood pressure assessment using Pulse Transit Time. In 2017 International Automatic Control Conference (CACS) (pp. 1-6). IEEE.

Huang, S. C., Hung, P. H., Hong, C. H., & Wang, H. M. (2014). A new image blood pressure sensor based on PPG, RRT, BPTT, and harmonic balancing. IEEE sensors Journal, 14(10), 3685-3692.

Ishikawa, T., Hyodo, Y., Miyashita, K., Yoshifuji, K., Komoriya, Y., & Imai, Y. (Feb. 2017). Wearable Motion Tolerant PPG Sensor for Instant Heart Rate in Daily Activity. In Biosignals (pp. 126-133).

Jain, M., Deb, S., & Subramanyam, A. V. (Sep. 2016). Face video based touchless blood pressure and heart rate estimation. In 2016 IEEE 18th International Workshop on Multimedia Signal Processing (MMSP) (pp. 1-5). IEEE.

Jarchi, D., & Casson, A. J. (2017). Towards photoplethysmography-based estimation of instantaneous heart rate during physical activity. IEEE Transactions on Biomedical Engineering, 64(9), 2042-2053.

Jarchi, D., Salvi, D., Tarassenko, L., & Clifton, D. (2018). Validation of Instantaneous Respiratory Rate Using Reflectance PPG from Different Body Positions. Sensors, 18(11), 3705.

Kachuee, M., Kiani, M. M., Mohammadzade, H., & Shabany, M. (2016). Cuffless blood pressure estimation algorithms for continuous health-care monitoring. IEEE Transactions on Biomedical Engineering, 64(4), 859-869.

Kamshilin, A. A., Miridonov, S., Teplov, V., Saarenheimo, R., & Nippolainen, E. (2011). Photoplethysmographic imaging of high spatial resolution. Biomedical optics express, 2(4), 996-1006.

Kamshilin, A. A., Sidorov, I. S., Babayan, L., Volynsky, M. A., Giniatullin, R., & Mamontov, O. V. (2016). Accurate measurement of the pulse wave delay with imaging photoplethysmography. Biomedical optics express, 7(12), 5138-5147.

Kamshilin, A. A., Teplov, V., Nippolainen, E., Miridonov, S., & Giniatullin, R. (2013). Variability of microcirculation detected by blood pulsation imaging. PloS one, 8(2), e57117.

Kong, L., Zhao, Y., Dong, L., Jian, Y., Jin, X., Li, B., . . . & Wu, H. (2013). Non-contact detection of oxygen saturation based on visible light imaging device using ambient light. Optics express, 21(15), 17464-17471.

Kumar, M., Veeraraghavan, A., & Sabharwal, A. (2015). DistancePPG: Robust non-contact vital signs monitoring using a camera. Biomedical optics express, 6(5), 1565-1588.

Li, T., & Zhou, X. (Oct. 2018). Battery-free eye tracker on glasses. In Proceedings of the 24th Annual International Conference on Mobile Computing and Networking (pp. 67-82). ACM.

Lin, S. T., Chen, W. II., & Lin, Y. II. (2017). A pulse rate detection method for mouse application based on multi-PPG sensors. Sensors, 17(7), 1628.

Liu, J., Yan, B. P. Y., Dai, W. X., Ding, X. R., Zhang, Y. T., & Zhao, N. (2016). Multi-wavelength photoplethysmography method for skin arterial pulse extraction. Biomedical optics express, 7(10), 4313-4326.

McDuff, D. J., Estepp, J. R., Piasecki, A. M., & Blackford, E. B. (Aug. 2015). A survey of remote optical photoplethysmographic imaging methods. In 2015 37th annual international conference of the IEEE engineering in medicine and biology society (EMBC) (pp. 6398-6404). IEEE.

McDuff, D., Gontarek, S., & Picard, R. W. (2014). Improvements in remote cardiopulmonary measurement using a five band digital camera. IEEE Transactions on Biomedical Engineering, 61(10), 2593-2601.

McDuff, D., Gontarek, S., & Picard, R. W. (2014). Remote detection of photoplethysmographic systolic and diastolic peaks using a digital camera. IEEE Transactions on Biomedical Engineering, 61(12), 2948-2954.

Mcduff, D., Hurter, C., & Gonzalez-Franco, M. (Nov. 2017). Pulse and vital sign measurement in mixed reality using a HoloLens. In Proceedings of the 23rd ACM Symposium on Virtual Reality Software and Technology (p. 34). ACM.

Meredith, D. J., Clifton, D., Charlton, P., Brooks, J., Pugh, C. W., & Tarassenko, L. (2012). Photoplethysmographic derivation of respiratory rate: a review of relevant physiology. Journal of medical engineering & technology, 36(1), 1-7.

Moco, A. V., Stuijk, S., & De Haan, G. (2016). Ballistocardiographic artifacts in PPG imaging. IEEE Transactions on Biomedical Engineering, 63(9), 1804-1811.

Moço, A., Stuijk, S., & de Haan, G. (2019). Posture effects on the calibratability of remote pulse oximetry in visible light. Physiological measurement, 40(3), 035005.

Moço, A., Stuijk, S., van Gastel, M., & de Haan, G. (2018). Impairing Factors in Remote-PPG Pulse Transit Time Measurements on the Face. In Proceedings of the IEEE Conference on Computer Vision and Pattern Recognition Workshops (pp. 1358-1366).

(56) References Cited

OTHER PUBLICATIONS

Po, L. M., Feng, L., Li, Y., Xu, X., Cheung, T. C. H., & Cheung, K. W. (2018). Block-based adaptive ROI for remote photoplethysmography. Multimedia Tools and Applications, 77(6), 6503-6529.

Poh, M. Z., McDuff, D. J., & Picard, R. W. (2010). Non-contact, automated cardiac pulse measurements using video imaging and blind source separation. Optics express, 18(10), 10762-10774.

Proença, J., Muehlsteff, J., Aubert, X., & Carvalho, P. (Aug. 2010). Is pulse transit time a good indicator of blood pressure changes during short physical exercise in a young population?. In 2010 Annual International Conference of the IEEE Engineering in Medicine and Biology (pp. 598-601). IEEE.

Ramirez, G. A., Fuentes, O., Crites Jr, S. L., Jimenez, M., & Ordonez, J. (2014). Color analysis of facial skin: Detection of emotional state. In Proceedings of the IEEE Conference on Computer Vision and Pattern Recognition Workshops (pp. 468-473).

Rouast, P. V., Adam, M. T., Chiong, R., Cornforth, D., & Lux, E. (2018). Remote heart rate measurement using low-cost RGB face video: a technical literature review. Frontiers of Computer Science, 12(5), 858-872.

Rundo, F., Conoci, S., Ortis, A., & Battiato, S. (2018). An advanced bio-inspired photoplethysmography (PPG) and ECG pattern recognition system for medical assessment. Sensors, 18(2), 405.

Saadatzi, M. N., Tafazzoli, F., Welch, K. C., & Graham, J. H. (Aug. 2016). Emotigo: Bluetooth-enabled eyewear for unobtrusive physiology-based emotion recognition. In 2016 IEEE International Conference on Automation Science and Engineering (CASE) (pp. 903-909). IEEE.

Samria, R., Jain, R., Jha, A., Saini, S., & Chowdhury, S. R. (Apr. 2014). Noninvasive cuffless estimation of blood pressure using Photoplethysmography without electrocardiograph measurement. In 2014 IEEE Region 10 Symposium (pp. 254-257). IEEE.

Shao, D., Tsow, F., Liu, C., Yang, Y., & Tao, N. (2017). Simultaneous monitoring of ballistocardiogram and photoplethysmogram using a camera. IEEE Transactions on Biomedical Engineering, 64(5), 1003-1010.

Sharma, M., Barbosa, K., Ho, V., Griggs, D., Ghirmai, T., Krishnan, S., . . . & Cao, H. (2017). Cuff-less and continuous blood pressure monitoring: A methodological review. Technologies, 5(2), 21.

Shirbani, F., Blackmore, C., Kazzi, C., Tan, I., Butlin, M., & Avolio, A. P. (Jul. 2018). Sensitivity of Video-Based Pulse Arrival Time to Dynamic Blood Pressure Changes. In 2018 40th Annual International Conference of the IEEE Engineering in Medicine and Biology Society (EMBC) (pp. 3639-3641). IEEE.

Solà, J., Proença, M., Braun, F., Pierrel, N., Degiorgis, Y., Verjus, C., . . . & Schoettker, P. (2016). Continuous non-invasive monitoring of blood pressure in the operating room: a cuffless optical technology at the fingertip. Current Directions in Biomedical Engineering, 2(1), 267-271.

Song, S. H., Cho, J. S., Oh, H. S., Lee, J. S., & Kim, I. Y. (Sep. 2009). Estimation of blood pressure using photoplethysmography on the wrist. In 2009 36th Annual Computers in Cardiology Conference (CinC) (pp. 741-744). IEEE.

Sun, Y., & Thakor, N. (2016). Photoplethysmography revisited: from contact to noncontact, from point to imaging. IEEE Transactions on Biomedical Engineering, 63(3), 463-477.

Trumpp, A., Rasche, S., Wedekind, D., Rudolf, M., Malberg, H., Matschke, K., & Zaunseder, S. (2017). Relation between pulse pressure and the pulsation strength in camera-based photoplethysmograms. Current Directions in Biomedical Engineering, 3(2), 489-492.

Vuksanović, V., Sheppard, L. W., & Stefanovska, A. (2008). Non-linear relationship between level of blood flow and skin temperature for different dynamics of temperature change. Biophysical journal, 94(10), L78-L80.

Wang, W., den Brinker, A. C., Stuijk, S., & de Haan, G. (2016). Algorithmic principles of remote PPG. IEEE Transactions on Biomedical Engineering, 64(7), 1479-1491.

Warren, K., Harvey, J., Chon, K., & Mendelson, Y. (2016). Improving pulse rate measurements during random motion using a wearable multichannel reflectance photoplethysmograph. Sensors, 16(3), 342.

Wu, B. F., Huang, P. W., Lin, C. H., Chung, M. L., Tsou, T. Y., & Wu, Y. L. (2018). Motion resistant image-photoplethysmography based on spectral peak tracking algorithm. IEEE Access, 6, 21621-21634.

Zaunseder, S., Trumpp, A., Wedekind, D., & Malberg, H. (2018). Cardiovascular assessment by imaging photoplethysmography—a review. Biomedical Engineering/Biomedizinische Technik, 63(5), 617-634.

Zhang, G., Shan, C., Kirenko, I., Long, X., & Aarts, R. (2017). Hybrid optical unobtrusive blood pressure measurements. Sensors, 17(7), 1541.

Niedermann, R., Wyss, E., Annaheim, S., Psikuta, A., Davey, S., & Rossi, R. M. (2014). Prediction of human core body temperature using non-invasive measurement methods. International journal of biometeorology, 58(1), 7-15.

Cheng, X., Yang, B., Hedman, A., Olofsson, T., Li, H., & Van Gool, L. (2018). Non-invasive thermal comfort perception based on subtleness magnification and deep learning for energy efficiency. arXiv preprint arXiv:1811.08006.

Looney, D. P., Buller, M. J., Gribok, A. V., Leger, J. L., Potter, A. W., Rumpler, W. V., . . . & Hoyt, R. W. (2018). Estimating resting core temperature using heart rate. Journal for the Measurement of Physical Behaviour, 1(2), 79-86.

Cheng, X., Yang, B., Tan, K., Isaksson, E., Li, L., Hedman, A., . . . & Li, H. (2019). A contactless measuring method of skin temperature based on the skin sensitivity index and deep learning. Applied Sciences, 9(7), 1375.

Cheng, X., Yang, B., Olofsson, T., Liu, G., & Li, H. (2017). A pilot study of online non-invasive measuring technology based on video magnification to determine skin temperature. Building and Environment, 121, 1-10.

AlZubaidi, A. K., Ethawi, Y., Schmölzer, G. M., Sherif, S., Narvey, M., & Seshia, M. (2018). Review of biomedical applications of contactless imaging of neonates using infrared thermography and beyond. Methods and Protocols, 1(4), 39.

Antink, C. H., Lyra, S., Paul, M., Yu, X., & Leonhardt, S. (2019). A broader look: Camera-based vital sign estimation across the spectrum. Yearbook of medical informatics, 28(1), 102.

Van Gastel, M., Stuijk, S., & De Haan, G. (2016). New principle for measuring arterial blood oxygenation, enabling motion-robust remote monitoring. Scientific reports, 6(1), 1-16.

Lenhardt, R., & Sessler, D. I. (2006). Estimation of mean body temperature from mean skin and core temperature. Anesthesiology: The Journal of the American Society of Anesthesiologists, 105(6), 1117-1121.

Arpornsuwan, M., & Arpornsuwan, M. (2020). Invisible Facial Flushing in Two Cases of Dengue Infection and Influenza Detected by PC Program and Smartphone App: Decorrelation Stretching and K-Means Clustering. Case Reports in Infectious Diseases, 2020.

International search report, PCT/IB2020/060196, dated Feb. 7, 2021.

Written opinion of the international searching authority, PCT/IB2020/060196, dated Feb. 7, 2021.

* cited by examiner

FIG. 1a      FIG. 1b

Two months later
$

Two months later
$$$$$$$

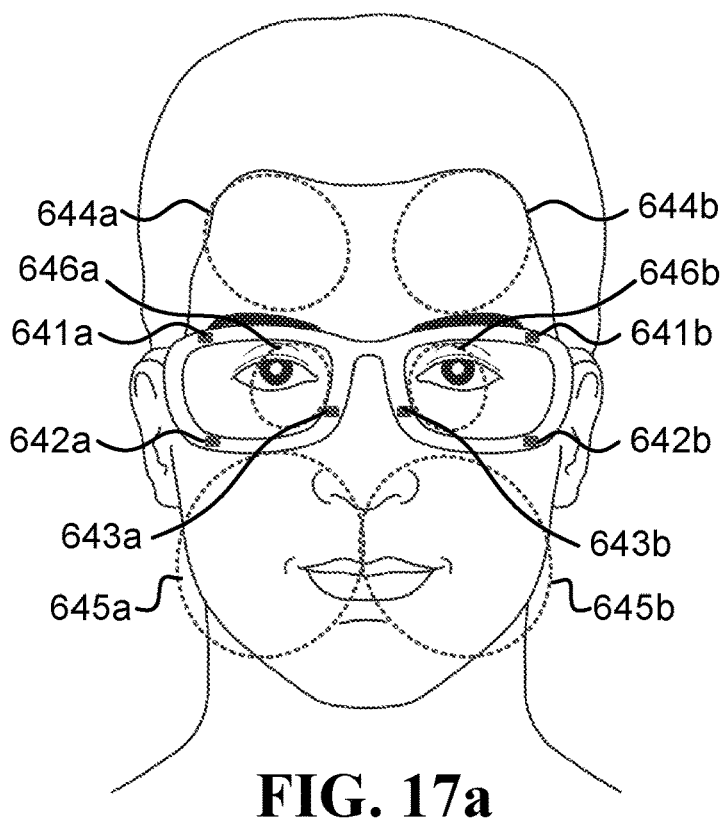
FIG. 17a
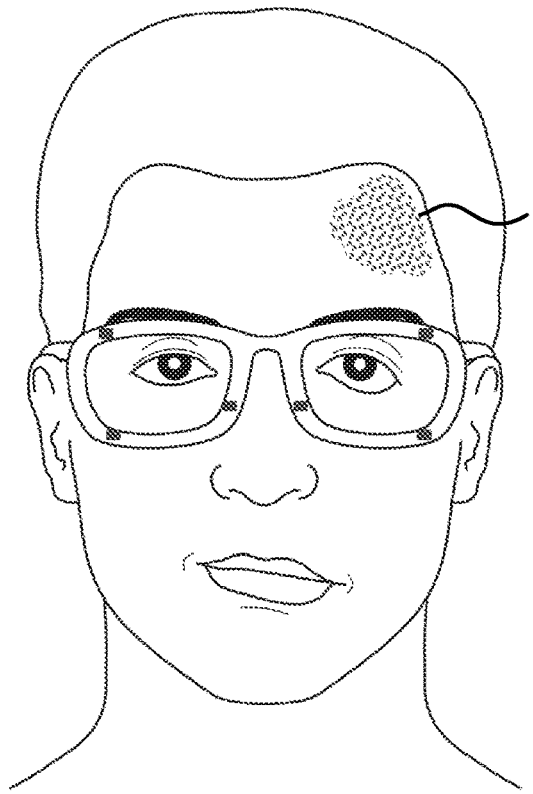 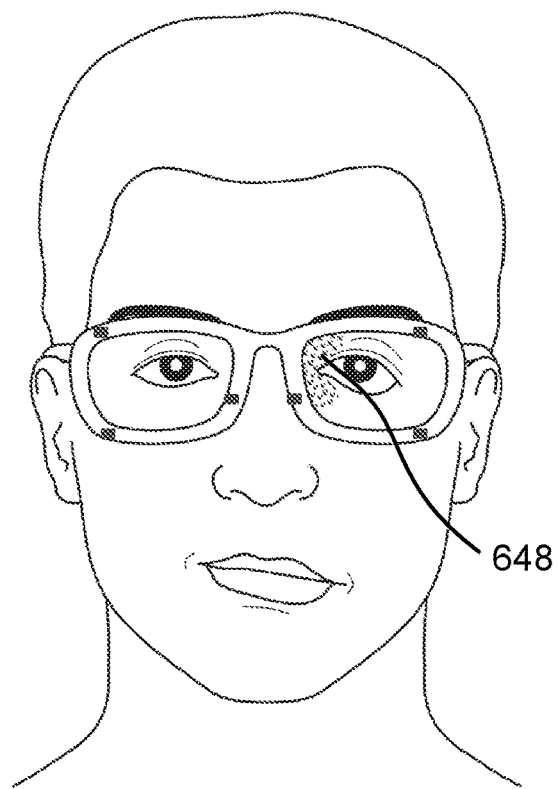
FIG. 17b        FIG. 17c

DETECTING FEVER FROM IMAGES AND TEMPERATURES

CROSS-REFERENCE TO RELATED APPLICATIONS

This application claims priority to U.S. Provisional Patent Application No. 62/928,726, filed Oct. 31, 2019, U.S. Provisional Patent Application No. 62/945,141, filed Dec. 7, 2019, U.S. Provisional Patent Application No. 62/960,913, filed Jan. 14, 2020, U.S. Provisional Patent Application No. 63/006,827, filed Apr. 8, 2020, U.S. Provisional Patent Application No. 63/024,471, filed May 13, 2020, and U.S. Provisional Patent Application No. 63/048,638, filed Jul. 6, 2020.

This application is a Continuation-In-Part of U.S. application Ser. No. 17/005,259, filed Aug. 27, 2020. U.S. Ser. No. 17/005,259 is a Continuation-In-Part of U.S. application Ser. No. 16/689,959, filed Nov. 20, 2019, which claims priority to U.S. Provisional Patent Application No. 62/874,430, filed Jul. 15, 2019. U.S. Ser. No. 17/005,259 is also a Continuation-In-Part of U.S. application Ser. No. 16/854,883, filed Apr. 21, 2020, which is a Continuation-In-Part of U.S. application Ser. No. 16/453,993, filed Jun. 26, 2019, now U.S. Pat. No. 10,667,697. U.S. Ser. No. 17/005,259 is also a Continuation-In-Part of U.S. application Ser. No. 16/831,413, filed Mar. 26, 2020, which is a Continuation-In-Part of U.S. application Ser. No. 16/551,654, filed Aug. 26, 2019, now U.S. Pat. No. 10,638,938. U.S. Ser. No. 16/551,654 is a Continuation-In-Part of U.S. application Ser. No. 16/453,993, filed Jun. 26, 2019. U.S. Ser. No. 16/453,993 is a Continuation-In-Part of U.S. application Ser. No. 16/375,841, filed Apr. 4, 2019. U.S. Ser. No. 16/375,841 is a Continuation-In-Part of U.S. application Ser. No. 16/156,493, now U.S. Pat. No. 10,524,667, filed Oct. 10, 2018. U.S. Ser. No. 16/156,493, is a Continuation-In-Part of U.S. application Ser. No. 15/635,178, filed Jun. 27, 2017, now U.S. Pat. No. 10,136,856, which claims priority to U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/231,276, filed Aug. 8, 2016, which claims priority to U.S. Provisional Patent Application No. 62/202,808, filed Aug. 8, 2015, and U.S. Provisional Patent Application No. 62/236,868, filed Oct. 3, 2015.

U.S. Ser. No. 16/156,493 is also a Continuation-In-Part of U.S. application Ser. No. 15/832,855, filed Dec. 6, 2017, now U.S. Pat. No. 10,130,308, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 15/832,855 is a Continuation-In-Part of U.S. application Ser. No. 15/182,592, filed Jun. 14, 2016, now U.S. Pat. No. 10,165,949, a Continuation-In-Part of U.S. application Ser. No. 15/231,276, filed Aug. 8, 2016, a Continuation-In-Part of U.S. application Ser. No. 15/284,528, filed Oct. 3, 2016, now U.S. Pat. No. 10,113,913, a Continuation-In-Part of U.S. application Ser. No. 15/635,178, filed Jun. 27, 2017, now U.S. Pat. No. 10,136,856, and a Continuation-In-Part of U.S. application Ser. No. 15/722,434, filed Oct. 2, 2017.

U.S. Ser. No. 15/832,855 is a Continuation-In-Part of U.S. application Ser. No. 15/182,566, filed Jun. 14, 2016, now U.S. Pat. No. 9,867,546, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/182,592 claims priority to U.S. Provisional Patent Application No. 62/175,319, filed Jun. 14, 2015, and U.S. Provisional Patent Application No. 62/202,808, filed Aug. 8, 2015.

U.S. Ser. No. 15/284,528 claims priority to U.S. Provisional Patent Application No. 62/236,868, filed Oct. 3, 2015, and U.S. Provisional Patent Application No. 62/354,833, filed Jun. 27, 2016, and U.S. Provisional Patent Application No. 62/372,063, filed Aug. 8, 2016.

U.S. Ser. No. 16/156,493 is also a Continuation-In-Part of U.S. application Ser. No. 15/833,115, filed Dec. 6, 2017, now U.S. Pat. No. 10,130,261. U.S. Ser. No. 15/833,115 is a Continuation-In-Part of U.S. application Ser. No. 15/182,592, a Continuation-In-Part of U.S. application Ser. No. 15/231,276, filed Aug. 8, 2016, a Continuation-In-Part of U.S. application Ser. No. 15/284,528, a Continuation-In-Part of U.S. application Ser. No. 15/635,178, and a Continuation-In-Part of U.S. application Ser. No. 15/722,434, filed Oct. 2, 2017.

U.S. Ser. No. 16/453,993 is also a Continuation-In-Part of U.S. application Ser. No. 16/147,695, filed Sep. 29, 2018. U.S. Ser. No. 16/147,695 is a Continuation of U.S. application Ser. No. 15/182,592, filed Jun. 14, 2016, which claims priority to U.S. Provisional Patent Application No. 62/175,319, filed Jun. 14, 2015, and U.S. Provisional Patent Application No. 62/202,808, filed Aug. 8, 2015.

U.S. Ser. No. 17/005,259 is also a Continuation-hi-Part of U.S. Ser. No. 16/689,929, filed Nov. 20, 2019, that is a Continuation-In-Part of U.S. Ser. No. 16/156,586, filed Oct. 10, 2018, that is a Continuation-hi-Part of U.S. application Ser. No. 15/832,815, filed Dec. 6, 2017, which claims priority to U.S. Provisional Patent Application No. 62/456,105, filed Feb. 7, 2017, and U.S. Provisional Patent Application No. 62/480,496, filed Apr. 2, 2017, and U.S. Provisional Patent Application No. 62/566,572, filed Oct. 2, 2017. U.S. Ser. No. 16/156,586 is also a Continuation-In-Part of U.S. application Ser. No. 15/859,772 Jan. 2, 2018, now U.S. Pat. No. 10,159,411.

ACKNOWLEDGMENTS

Gil Thieberger would like to thank his holy and beloved teacher, Lama Dvora-hla, for her extraordinary teachings and manifestation of wisdom, love, compassion and morality, and for her endless efforts, support, and skills in guiding him and others on their paths to freedom and ultimate happiness. Gil would also like to thank his beloved parents for raising him with love and care.

BACKGROUND

It is often difficult to detect fever, to calculate core body temperature, and/or to detect alcohol intoxication from facial measurements. This is especially true in some real-life circumstances, such as when an air conditioner hose is directed towards the user's face, while sitting close to a heater, while being outside in the sun, or while being in cold wind. It is also difficult to measure the temperature of the environment by a smartwatch or a non-wearable temperature sensor, because the hand with the smartwatch may be covered, and the non-wearable temperature sensor may not be exposed to radiation or wind hitting the face.

However, detecting fever and calculating core body temperature are very important. Fever is a common symptom of many medical conditions: infectious disease, such as COVID-19, dengue, Ebola, gastroenteritis, influenza, Lyme disease, malaria, as well as infections of the skin. It is important to track fever in order to be able to identify when a person might be sick and should be isolated (when an infectious disease is suspected).

The most common way to track fever involves using a thermometer, which interrupts day-to-day activities. The most common way to track alcohol intoxication (drunkenness) involves using a breathalyzer, which also interrupts the day-to-day activities. As a result, there is a need for a relatively inexpensive and unobtrusive way to accurately detect whether a user has a fever and/or is intoxicated, without interrupting the user's daily activities.

SUMMARY

Described herein are embodiments of systems and methods that utilize images of a user's face, as well as temperature measurements of the user's face and the environment, for various purposes such as detecting fever, estimating core body temperature, detecting intoxication, and additional applications. The images may be captured using different hardware setups. In some embodiments, the images are captured using one or more inward facing head-mounted cameras (e.g., one or more cameras attached to, or embedded in, smartglasses frames, helmets, or goggles). In other embodiments, the images may be captured using an external, non-head-mounted camera, such as a camera in a smartphone held by the user.

Some aspects of this disclosure involve utilization of sensors that are physically coupled to smartglasses in order to conveniently, and optionally continuously, monitor users. Smartglasses are generally comfortable to wear, lightweight, and can have extended battery life. Thus, they are well suited as an instrument for long-term monitoring of patient's physiological signals and activity, in order to determine whether the user has a fever and/or whether the user is intoxicated.

One aspect of this disclosure involves a system configured to detect fever. In one embodiment, the system includes a first head-mounted temperature sensor configured to measure skin temperature ($T_{skin}$) at a first region on a user's head, a second head-mounted temperature sensor configured to measure temperature of the environment ($T_{env}$), and a computer. The computer is configured to: receive images of a second region on the user's face, captured by a camera sensitive to wavelengths below 1050 nanometer, calculate, based on the images, values indicative of hemoglobin concentrations at three or more regions on the user's face; and detect whether the user has a fever based on $T_{skin}$, $T_{env}$, and the values.

In one embodiment, the first region covers a portion of skin that is not located above a portion of a branch of the external carotid artery, and the computer detects whether the user has the fever by (i) generating feature values based on: $T_{skin}$, $T_{env}$, and the values indicative of hemoglobin concentrations, and (ii) utilizing a machine learning based model to calculate, based on the feature values, a values indicative of whether the user has the fever.

In one example, the first head-mounted temperature sensor is a contact temperature sensor that is not located above a portion of a branch of the external carotid artery, the second region is larger than 3 cm², and the camera is not head-mounted and is configured to capture the images from a distance longer than 5 cm from the user's head.

In another example, the first head-mounted temperature sensor includes an inward-facing thermal camera located more than 2 mm away from the user's head, the second region is larger than 2 cm², and the camera is an inward facing head-mounted camera configured to capture the images from a distance between 5 mm and 5 cm from the user's head.

In one embodiment, the computer utilizes one or more calibration measurements of the user's core body temperature, taken by a different device, to calibrate a model, and utilizes said calibrated model to calculate the user's core body temperature based on $T_{skin}$, $T_{env}$, and the indicative of hemoglobin concentrations at three or more regions on the user's face. Optionally, the computer shares a fever history of the user upon receiving a permission from the user.

In one embodiment, the computer calculates the values indicative of hemoglobin concentrations based on detecting imaging photoplethysmogram signals in the images. Optionally, the computer utilize one or more calibration measurements of the user's core body temperature, taken by a different device (which is not the camera or head-mounted temperature sensors), prior to a certain time, and to calculate the user's core body temperature based on $T_{skin}$, $T_{env}$, and the values, which were taken after the certain time.

In one embodiment, the system includes a head-mounted acoustic sensor that takes audio recordings of the user, and a head-mounted movement sensor that measures a signal indicative of movements of the user's head (head-movement signal). In this embodiment, the computer (i) generates feature values based on $T_{skin}$, $T_{env}$, the values indicative of hemoglobin concentrations, the audio recordings, and the head-movement signal, and (ii) utilizes a machine learning based model to calculate, based on the feature values, level of dehydration of the user. Optionally, for generating the feature values based on the audio recordings, the computer extracts features indicative of the user's respiratory rate and vocal changes. Dehydration is often associated with an increase in the respiratory rate and a decrease in the speed quotient at low pitch phonation.

In another embodiment, the system includes a head-mounted acoustic sensor configured to take audio recordings of the user. In this embodiment, the computer (i) generates feature values based on $T_{skin}$, $T_{env}$, the values indicative of hemoglobin concentrations, and the audio recordings, and (ii) utilizes a machine learning-based model to detect, based on the feature values, the user's core body temperature and/or whether the user has the fever, hyperthermia, or hypothermia. Optionally, the feature values generated based on the audio recordings are indicative of the user's respiration rate.

In yet another embodiment, the system includes a head-mounted movement sensor that measures a signal indicative of movements of the user's head (head-movement signal). In this embodiment, the computer (i) generates feature values based on $T_{skin}$, $T_{env}$, the values indicative of hemoglobin concentrations, and the head-movement signal, and (ii) utilizes a machine learning-based model to detect, based on the feature values, the user's core body temperature and/or whether the user has the fever, hyperthermia, or hypothermia. Optionally, the feature values based on the head-movement signal are indicative of the user's physical activity level.

In still another embodiment, the system includes a head-mounted anemometer that measures a signal indicative of wind speed hitting the user's head (wind signal), and a head-mounted hygrometer that measures a signal indicative of humidity (humidity signal). In this embodiment, the computer (i) generates feature values based on $T_{skin}$, $T_{env}$, the values indicative of hemoglobin concentrations, the wind signal, and the humidity signal, and (ii) utilizes a machine learning-based model to detect, based on the feature values, the user's core body temperature and/or whether the user has the fever, hyperthermia, or hypothermia.

Embodiments of the system may be implemented using various head-mounted objects that are worn on the user's head. In one example, the system includes a helmet or goggles configured to be worn on the user's head, the first head-mounted temperature sensor is physically coupled to the helmet or goggles, and the first region is located on the user's forehead, cheekbone, or temple. In another example, the system includes an eyeglasses frame configured to be worn on the user's head, the first head-mounted temperature sensor is physically coupled to the frame, and the first region is located on the user's nose or temple. Optionally, in this example, the computer configured to: calculate, based on additional images captured with the camera while the user had a fever, additional values indicative of hemoglobin concentrations at the three or more regions on the user's face while the user had the fever, and base the detection of whether the user has the fever also on a deviation of the values from the additional values.

In one embodiment, the images of the second region on the user's face include a first channel corresponding to wavelengths that are mostly below 580 nanometers and a second channel corresponding to wavelengths mostly above 580 nanometers. Optionally, the values indicative of hemoglobin concentrations include: (i) first values derived based on the first channel in the images, and (ii) second values derived based on the second channel in the images. Having separate values for different wavelengths may enable to account for interference from the environment when detecting whether the user has the fever.

Another aspect of this disclosure is a method for detecting fever. In one embodiment, the method includes at least the following steps: In Step 1, receiving, from a first head-mounted temperature sensor, measurements of skin temperature ($T_{skin}$) at a first region on a user's head; In Step 2, receiving, from a second head-mounted temperature sensor, measurements of temperature of the environment ($T_{env}$); In Step 3, receiving, from a camera sensitive to wavelengths below 1050 nanometer, images of a second region on the user's face; In Step 4, calculating, based on the images, values indicative of hemoglobin concentrations at three or more regions on the user's face; And in Step 5, detecting whether the user has a fever based on $T_{skin}$, $T_{env}$, and the values indicative of hemoglobin concentrations.

In one embodiment, the first region covers a portion of skin that is not located above a portion of a branch of the external carotid artery, and detecting of whether the user has the fever in Step 5 involves (i) generating feature values based on: $T_{skin}$, $T_{env}$, and the values indicative of hemoglobin concentrations, and (ii) utilizing a machine learning based model to calculate, based on the feature values, a values indicative of whether the user has the fever.

Yet another aspect of this disclosure involves a system configured to detect alcohol intoxication. In one embodiment, the system includes a first head-mounted temperature sensor configured to measure skin temperature Dakin) at a first region on a user's head, a second head-mounted temperature sensor configured to measure temperature of the environment ($T_{env}$), and a computer. The computer is configured to: receive images of a second region on the user's face, captured by a camera sensitive to wavelengths below 1050 nanometer; calculate, based on the images, values indicative of hemoglobin concentrations at three or more regions on the user's face; and detect whether the user is intoxicated based on $T_{skin}$, $T_{env}$, and the values.

In one embodiment, the computer performs the detection of whether the user is intoxicated by (i) generating feature values based on: $T_{skin}$, $T_{env}$, and the values indicative of hemoglobin concentrations; and (ii) utilizing a machine learning-based model to calculate, based on the feature values, a values indicative of whether the user is intoxicated. Optionally, the machine learning-based model was trained based on previous data sets comprising: (i) $T_{skin}$, $T_{env}$, and previous values indicative of hemoglobin concentrations captured by the camera while the user was sober, and (ii) $T_{skin}$, $T_{env}$, and previous values indicative of hemoglobin concentrations captured by the camera while the user was intoxicated.

In one embodiment, the second region is larger than 2 $cm^2$, the camera is an inward facing head-mounted camera configured to capture the images from a distance between 5 mm and 5 cm from the user's head, and the computer calculates the values indicative of hemoglobin concentrations based on detecting facial flushing patterns in the images.

In another embodiment, the camera is an inward facing head-mounted camera configured to capture the images from a distance between 5 mm and 5 cm from the user's head, and the computer calculates the values indicative of hemoglobin concentrations based on detecting imaging photoplethysmogram signals in the images.

BRIEF DESCRIPTION OF THE DRAWINGS

The embodiments are herein described by way of example only, with reference to the following drawings:

FIG. 1a illustrates an example of a hemoglobin concentration pattern of a sober person;

FIG. 1b illustrates an example of the hemoglobin concentration pattern of the same person when intoxicated;

FIG. 17a illustrates one embodiment of a system that includes multiple pairs of right and left cameras and locations on the face that they may be used to measure;

FIG. 17b illustrates a stroke sign that involves decreased blood flow in the forehead;

FIG. 17c illustrates a stroke sign that involves decreased blood flow in a periorbital region;

DETAILED DESCRIPTION

Figure 1C:
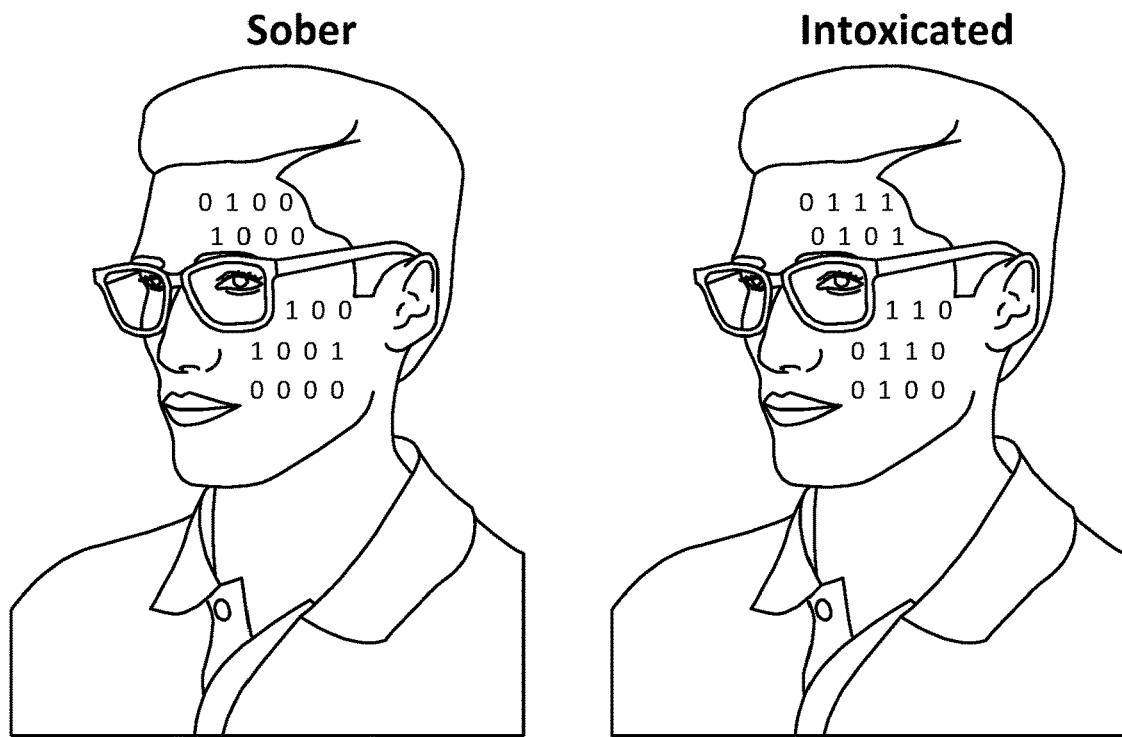
FIG. 1c is a schematic illustration of components of a system to detect fever and/or intoxication.
Figure 1C:
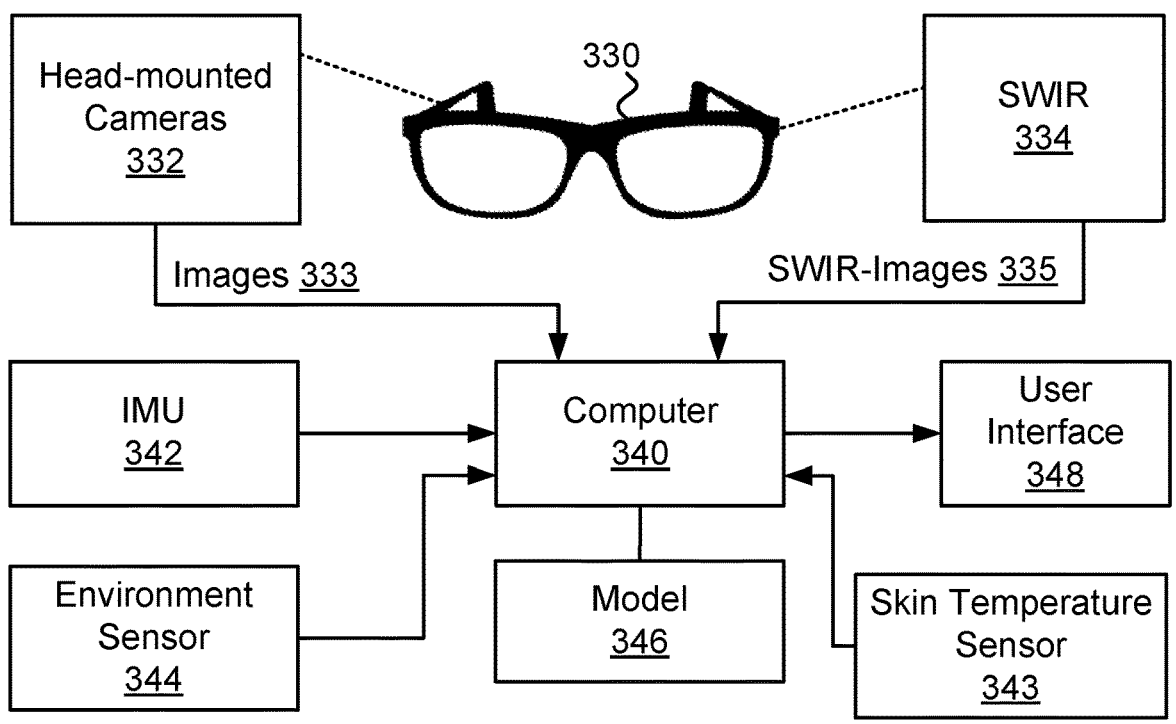

Herein the terms "photoplethysmogram signal", "photoplethysmographic signal", "photoplethysmography signal", and other similar variations are interchangeable and refer to the same type of signal. A photoplethysmogram signal may be referred to as a "PPG signal", or an "iPPG signal" when specifically referring to a PPG signal obtained from a camera. The terms "photoplethysmography device", "photoplethysmographic device", "photoplethysmogram device", and other similar variations are also interchangeable and refer to the same type of device that measures a signal from which it is possible to extract the photoplethysmogram signal. The photoplethysmography device may be referred to as "PPG device".

Sentences in the form of "a sensor configured to measure a signal indicative of a photoplethysmogram signal" refer to at least one of: (i) a contact PPG device, such as a pulse oximeter that illuminates the skin and measures changes in light absorption, where the changes in light absorption are indicative of the PPG signal, and (ii) a non-contact camera that captures images of the skin, where a computer extracts the PPG signal from the images using an imaging photoplethysmography (iPPG) technique. Other names known in the art for iPPG include: remote photoplethysmography (rPPG), remote photoplethysmographic imaging, remote imaging photoplethysmography, remote-PPG, and multi-site photoplethysmography (MPPG). Additional names known in the art for iPPG from the face include: facial hemoglobin concentration changes, dynamic hemoglobin concentration/information extraction, facial blood flow changes, and transdermal optical imaging.

A PPG signal is often obtained by using a pulse oximeter, which illuminates the skin and measures changes in light absorption. Another possibility for obtaining the PPG signal is using an imaging photoplethysmography (iPPG) device. As opposed to contact PPG devices, iPPG does not require contact with the skin and is obtained by a non-contact sensor, such as a video camera.

A time series of values measured by a PPG device, which is indicative of blood flow changes due to pulse waves, is typically referred to as a waveform (or PPG waveform to indicate it is obtained with a PPG device). It is well known that PPG waveforms show significant gender-related differences, age-related differences, and health-related differences. As a result, the PPG waveforms of different people often display different characteristics (e.g., slightly different shapes and/or amplitudes). In addition, the PPG waveform depends on the site at which it is measured, skin temperature, skin tone, and other parameters.

The analysis of PPG signals usually includes the following steps: filtration of a PPG signal (such as applying bandpass filtering and/or heuristic filtering), extraction of feature values from fiducial points in the PPG signal (and in some cases may also include extraction of feature values from non fiducial points in the PPG signal), and analysis of the feature values.

One type of features that is often used when performing calculations involving PPG signals involves fiducial points related to the waveforms of the PPG signal and/or to functions thereof (such as various derivatives of the PPG signal). There are many known techniques to identify the fiducial points in the PPG signal, and to extract the feature values. The following are some non-limiting examples of how to identify fiducial points.

Figure 2A:
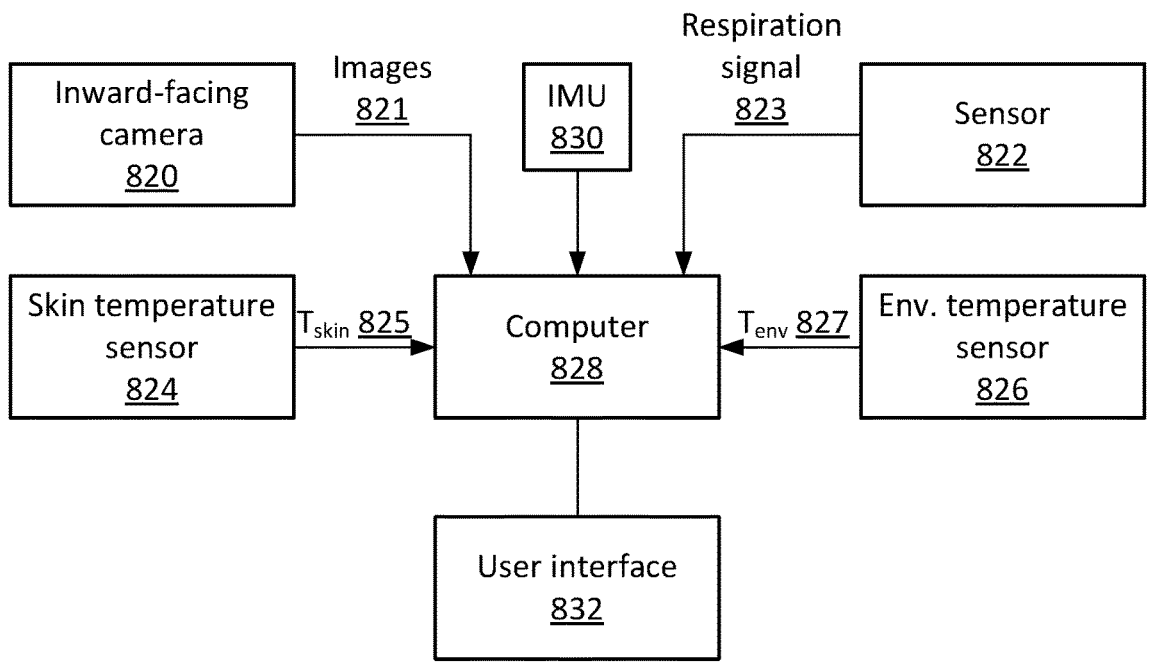
FIG. 2a is a schematic illustration of components of a system to calculate an extent of CHF and/or identify exacerbation of CHF.
Figure 2B:
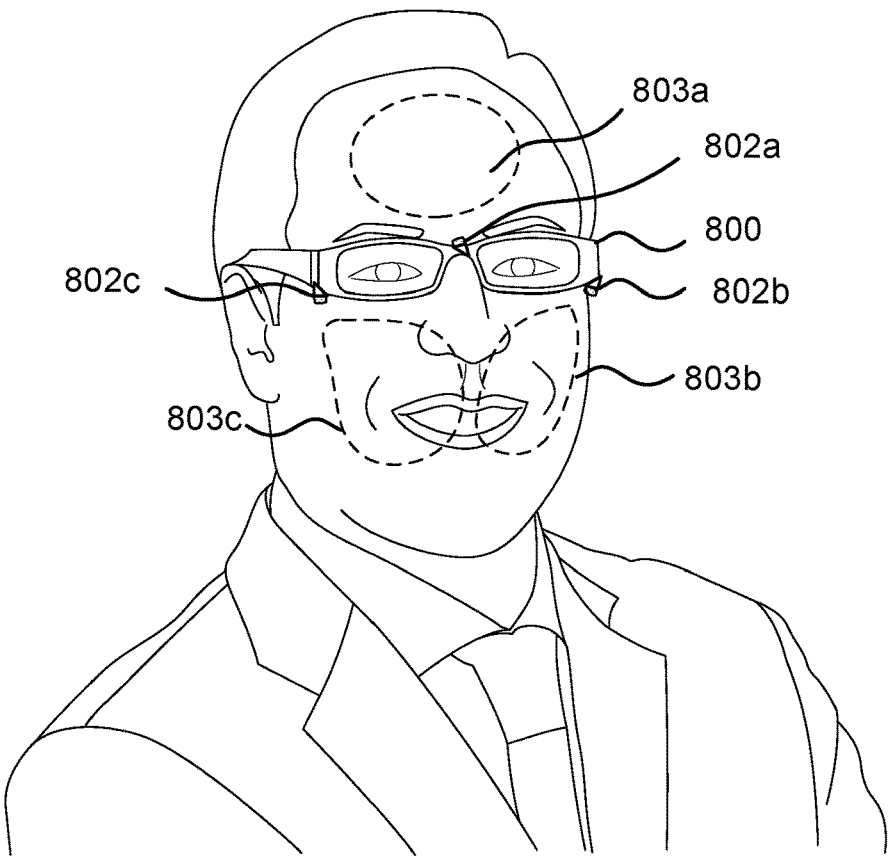
FIG. 2b illustrates various possibilities for positioning one or more inward-facing cameras on smartglasses.
Figure 2C:
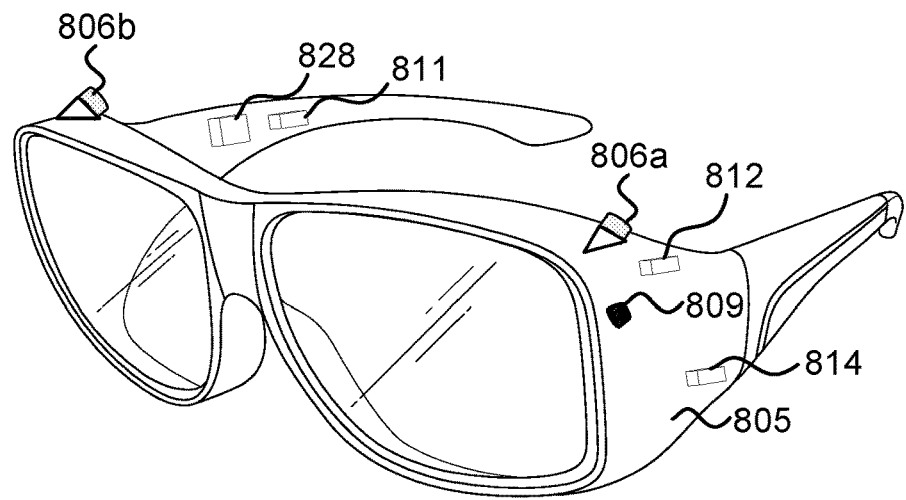
FIG. 2c illustrates an embodiment of smartglasses that are part of a system for calculating an extent of CHF that a user is suffering from, and/or identify exacerbation of CHF.
Figure 2D:
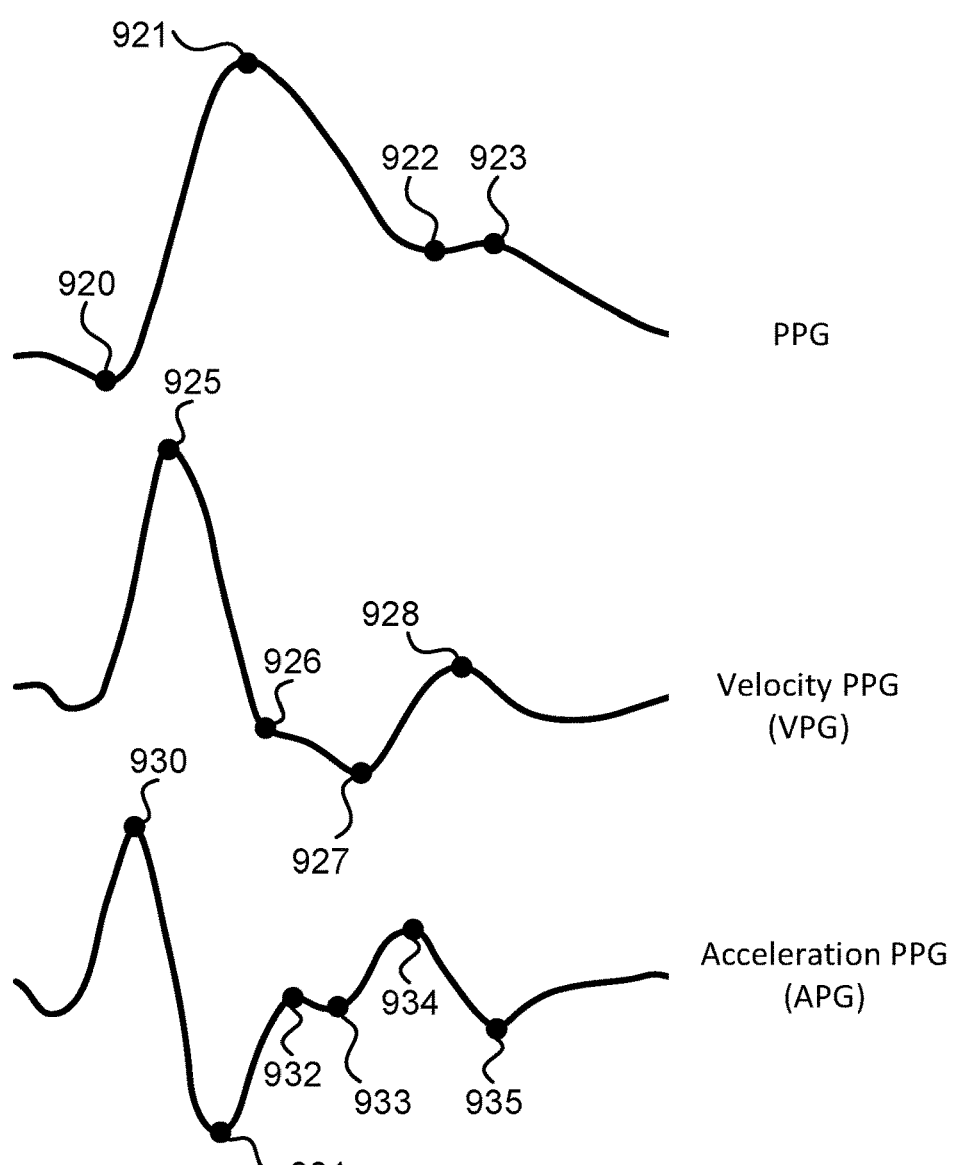
FIG. 2d is a schematic illustration of some of the various fiducial points for PPG signals often used in the art.

FIG. 2d is a schematic illustration some of the various fiducial points often used in the art (and described below). These examples of fiducial points include fiducial points of the PPG signal, fiducial points in the first derivative of the PPG signal (velocity photoplethysmogram, WG), and fiducial points in the second derivative of the PPG signal (acceleration photoplethysmogram, APG).

Fiducial points in the PPG signal may include: the systolic notch 920, which is the minimum at the PPG signal onset; the systolic peak 921, which is the maximum of the PPG signal; the dicrotic notch 922, coincident with e 934 below at the second derivative of the PPG signal); and the diastolic peak 923, which is the first local maximum of the PPG signal after the dicrotic notch and before 0.8 of the duration of the cardiac cycle, or if there is no such local maximum, then the first local maximum of the second derivative after e and before 0.8 of the duration of the cardiac cycle.

Fiducial points in the first derivative of the PPG signal (velocity photoplethysmogram, VPG) may include: the maximum slope peak in systolic of VPG 925; the local minima slope in systolic of VPG 926; the global minima slope in systolic of VPG 927: and the maximum slope peak in diastolic of VPG 928.

Fiducial points in the second derivative of the PPG signal (acceleration photoplethysmogram, APG) may include: a 930, which is the maximum of APG prior to the maximum of VPG; b 931, which is the first local minimum of APG following a; c 932, which is the greatest maximum of APG between b and e, or if no maxima then the first of (i) the first maximum of VPG after e, and (ii) the first minimum of APG after e; d 933, is the lowest minimum of APG after c and before e, or if no minima then coincident with c; e 934, which is the second maximum of APG after maximum of VPG and before 0.6 of the duration of the cardiac cycle, unless the c wave is an inflection point, in which case take the first maximum; and f 935, which is the first local minimum of APG after e and before 0.8 of the duration of the cardiac cycle.

Fiducial points in the third derivative of the PPG signal (PPG''') may include: the first local maximum of PPG''' after b; and the last local minimum of PPG''' before d, unless c=d, in which case take the first local minimum of PPG''' after d, and if there is a local maximum of the PPG signal between this point and the dicrotic notch then use it instead.

Feature values of the PPG signal may also be extracted from relationships in the PPG signal and/or its derivatives. The following are some non-limiting examples such possible feature values: pulse width, peak to peak time, ratio of areas before and after dicrotic notch in a complete cycle, baseline wander (BW), which is the mean of the amplitudes of a beat's peak and trough; amplitude modulation (AM), which is the difference between the amplitudes of each beat's peak and trough; and frequency modulation (FM), which is the time interval between consecutive peaks.

Examples of additional features that can be extracted from the PPG signal, together with schematic illustrations of the feature locations on the PPG signal, can be found in the following three publications: (i) Peltokangas, Mikko, et at "Parameters extracted from arterial pulse waves as markers of atherosclerotic changes: performance and repeatability." IEEE journal of biomedical and health informatics 22.3 (2017): 750-757; Ahn, Jae Mok. "New aging index using signal features of both photoplethysmograms and acceleration plethysmograms." Healthcare informatics research 23.1 (2017): 53-59; (iii) Charlton, Peter H., et al. "Assessing mental stress from the photoplethysmogram: a numerical study." Physiological measurement 39.5 (2018): 054001, and (iv) Peralta, Elena, et at "Optimal fiducial points for pulse rate variability analysis from forehead and finger photoplethysmographic signals." Physiological measurement 40.2 (2019): 025007.

Although the above mentioned references describe manual feature selection, the features may be selected using any appropriate feature engineering technique, including using automated feature engineering tools that help data scientists to reduce data exploration time, and enable non-experts, who may not be familiar with data science and/or PPG characteristics, to quickly extract value from their data with little effort.

Unless there is a specific reference to a specific derivative of the PPG signal, phrases of the form of "based on the PPG signal" refer to the PPG signal and any derivative thereof, including the first derivative of the PPG signal, the second derivative of the PPG signal, and the third derivative of the PPG signal. For example, a sentence in the form of "a computer configured to detect a physiological signal based on the PPG signal" is to be interpreted as "a computer configured to detect a physiological signal based on at least one of: the PPG signal, a first derivative of the PPG signal, a second derivative of the PPG signal, a the third derivative of the PPG signal, and/or any other derivative of the PPG signal".

Algorithms for filtration of the PPG signal (and/or the images in the case of iPPG), extraction of feature values from fiducial points in the PPG signal, and analysis of the feature values extracted from the PPG signal are well known in the art, and can be found for example in the following references: (i) Allen, John. "Photoplethysmography and its application in clinical physiological measurement." Physiological measurement 28.3 (2007): R1, and also in the thousands of references citing this reference; (ii) Elgendi, Mohamed "On the analysis of fingertip photoplethysmogram signals." Current cardiology reviews 8.1 (2012): 14-25, and also in the hundreds of references citing this reference; (iii) Holton, Benjamin D., et at "Signal recovery in imaging photoplethysmography." Physiological measurement 34.11 (2013): 1499, and also in the dozens of references citing this reference, (iv) Sun, Yu, and Nitish Thakor. "Photoplethysmography revisited: from contact to noncontact, from point to imaging" IEEE Transactions on Biomedical Engineering 63.3 (2015): 463-477, and also in the dozens of references citing this reference, (v) Kumar, Mayank, Ashok Veeraraghavan, and Ashutosh Sabhanval. "DistancePPG: Robust non-contact vital signs monitoring using a camera." Biomedical optics express 6.5 (2015): 1565-1588, and also in the dozens of references citing this reference, (vi) Wang, Wenjin, et at "Algorithmic principles of remote PPG." IEEE Transactions on Biomedical Engineering 64.7 (2016): 1479-1491, and also in the dozens of references citing this reference, and (vii) Rouast, Philipp V., et al. "Remote heart rate measurement using low-cost RGB face video: a technical literature review." Frontiers of Computer Science 12.5 (2018): 858-872, and also in the dozens of references citing this reference.

In the case of iPPG, the input comprises images having multiple pixels. The images from which the iPPG signal and/or the hemoglobin concentration patterns are extracted may undergo various preprocessing to improve the signal, such as color space transformation, blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting iPPG signals from images are discussed in Zaunseder et al. (2018), "Cardiovascular assessment by imaging photoplethysmography—a review", Biomedical Engineering 63(5), 617-634.

Various embodiments described herein involve calculations based on machine learning approaches. Herein, the terms "machine learning approach" and/or "machine learning based approaches" refer to learning from examples using one or more approaches. Examples of machine learning approaches include: decision tree learning, association rule learning, regression models, nearest neighbors classifiers, artificial neural networks, deep learning, inductive logic programming, support vector machines, clustering, Bayesian networks, reinforcement learning, representation learning, similarity and metric learning, sparse dictionary learning, genetic algorithms, rule-based machine learning, and/or learning classifier systems.

Herein, a "machine learning-based model" is a model trained using one or more machine learning approaches. For brevity's sake, at times, a "machine learning based model" may simply be called a "model". Referring to a model as being "machine learning-based" is intended to indicate that the model is trained using one or more machine learning approaches (otherwise, "model" may also refer to a model generated by methods other than machine learning).

Herein, "feature values" (also known as feature vector, feature data, and numerical features) may be considered input to a computer that utilizes a model to perform the calculation of a value, such as a value indicative of one or more vital signs of a user. It is to be noted that the terms "feature" and "feature value" may be used interchangeably when the context of their use is clear. However, a "feature" typically refers to a certain type of value, and represents a property, while "feature value" is the value of the property with a certain instance (i.e., the value of the feature in a certain sample).

It is to be noted that when it is stated that feature values are generated based on data comprising multiple sources, it means that for each source, there is at least one feature value that is generated based on that source (and possibly other data). For example, stating that feature values are generated from an image capturing first and second regions ($IM_{ROI1}$ and $IM_{ROI2}$, respectively) means that the feature values include at least a first feature value generated based on $IM_{ROI1}$ and a second feature value generated based on $IM_{ROI2}$.

In addition to feature values generated based on measurements taken by sensors mentioned in a specific embodiment, at least some feature values utilized by a computer of the specific embodiment may be generated based on additional sources of data that were not specifically mentioned in the specific embodiment. Some examples of such additional sources of data include: (i) contextual information such as the time of day (e.g., to account for effects of the circadian rhythm), day of month (e.g., to account for effects of the lunar rhythm), day in the year (e.g., to account for seasonal effects), and/or stage in a menstrual cycle; (ii) information about the user being measured such as sex, age, weight, height, body build, genetics, medical records, and/or intake of substances; (iii) measurements of the environment, such as temperature, humidity level, noise level, elevation, air quality, a wind speed, precipitation, and infrared radiation; and/or (iv) values of physiological signals of the user obtained by sensors that are not mentioned in the specific embodiment, such as an electrocardiogram (ECG) sensor, an electroencephalography (EEG) sensor, a galvanic skin response (GSR) sensor, a movement sensor, an acoustic sensor, and/or a temperature sensor.

A machine learning-based model of a specific embodiment may be trained, in some embodiments, based on data collected in day-to-day, real world scenarios. As such, the data may be collected at different times of the day, while users perform various activities, and in various environmental conditions. Utilizing such diverse training data may enable a trained model to be more resilient to the various effects that different conditions can have on the measurements, and consequently, be able to achieve better detection of a required parameter in real world day-to-day scenarios.

The machine learning-based model may be personalized for a specific user. For example, after receiving a verified diagnosis of an extent of a physiological condition (such as blood pressure level, extent of a cardiovascular disease, extent of a pulmonary disease, extent of a migraine attack, etc.), the computed can use the verified diagnosis as labels and generate from a physiological measurement (such as the PPG signal, the temperature signal, the movement signal, and/or the audio signal) feature values to train a personalized machine learning-based model for the user. Then the computer can utilize the personalized machine learning based model for future calculations of the extent of the physiological condition based on feature values.

Sentences in the form of "inward-facing head-mounted camera" refer to a camera configured to be worn on a user's head and to remain pointed at its ROI, which is on the user's face, also when the user's head makes angular and lateral movements (such as movements with an angular velocity above 0.1 rad/sec, above 0.5 rad/sec, and/or above 1 rad/sec). A head-mounted camera (which may be inward-facing and/or outward-facing) may be physically coupled to a frame worn on the user's head, may be physically coupled to eyeglasses using a clip-on mechanism (configured to be attached to and detached from the eyeglasses), may be physically coupled to a hat or a helmet, or may be mounted to the user's head using any other known device that keeps the camera in a fixed position relative to the user's head also when the head moves. Sentences in the form of "sensor physically coupled to the frame" mean that the sensor moves with the frame, such as when the sensor is fixed to (or integrated into) the frame, and/or when the sensor is fixed to (or integrated into) an element that is physically coupled to the frame, and/or when the sensor is connected to the frame with a clip-on mechanism.

Sentences in the form of "a frame configured to be worn on a user's head" or "a frame worn on a user's head" refer to a mechanical structure that loads more than 50% of its weight on the user's head. For example, an eyeglasses frame may include two temples connected to two rims connected by abridge; the frame in Oculus Rift™ includes the foam placed on the user's face and the straps; and the frame in Google Glass™ is similar to an eyeglasses frame. Additionally or alternatively, the frame may connect to, be affixed within, and/or be integrated with, a helmet (e.g., a safety helmet, a motorcycle helmet, a combat helmet, a sports helmet, a bicycle helmet, etc.), goggles, and/or a brainwave-measuring headset.

Sentences in the form of "a frame configured to be worn on a user's head in a consistent manner" refer to a frame that is located in the same position relative to the head when worn repeatedly, and thus sensors attached to that frame are most likely to be positioned each time at the same location relative to the head. For example, eyeglasses frames, goggles, and helmets are all included under the definition of a frame that is worn in a consistent manner. However, a flexible headband, or adhesive sensors that are placed manually one by one, are not worn in a consistent manner, because these sensors are most likely to be positioned each time in a different location relative to the head.

The term "smartglasses" refers to any type of a device that resembles eyeglasses, and includes a frame configured to be worn on a user's head in a consistent manner, and includes electronics to operate one or more sensors. The frame may be an integral part of the smartglasses, and/or an element that is connected to the smartglasses. Examples of smartglasses include: any type of eyeglasses with electronics (whether prescription or plano), sunglasses with electronics, safety goggles with electronics, sports goggle with electronics, augmented reality devices, virtual reality devices, and mixed reality devices. In addition, the term "eyeglasses frame" refers to one or more of the following devices, whether with or without electronics: smartglasses, prescription eyeglasses, plano eyeglasses, prescription sunglasses, plano sunglasses, safety goggles, sports goggle, an augmented reality device, virtual reality devices, and a mixed reality device.

The term "smart-helmet" refers to a helmet that includes a frame configured to be worn on a user's head in a consistent manner, and includes electronics to operate one or more sensors. The frame may be an integral part of the smart-helmet, and/or an element that is connected to the smart-helmet. Examples of smart-helmets include: a safety helmet with electronics, a motorcycle helmet with electronics, a combat helmet with electronics, a sports helmet with electronics, and a bicycle helmet with electronics.

Examples of electronics that may be included in smartglasses and/or a smart-helmet include one or more of the following electronic components: a computer, a microcontroller, a processor, a memory, and a communication interface. The electronics of the smartglasses and/or smart-helmets may be integrated in various ways. For example, the electronics may be integrated into the package of one of the sensors, such as a camera housing that is physically coupled to a helmet, where the housing includes the imaging sensor and its processor, memory, power supply and wireless communication unit. In another example, the electronics may be integrated into the frame, such as a microcontroller, power supply and wireless communication unit that are integrated into an eyeglasses frame, and configured to operate a PPG device and a microphone that are physically coupled to the frame.

The term "Visible-light camera" refers to a non-contact device designed to detect at least some of the visible spectrum, such as a video camera with optical lenses and CMOS or CCD sensor. The term "thermal camera" refers to a non-contact device that measures electromagnetic radiation having wavelengths longer than 2500 nanometer (nm) and does not touch its region of interest (ROI). A thermal camera may include one sensing element (pixel), or multiple sensing elements that are also referred to herein as "sensing pixels", "pixels", and/or focal-plane array (FPA). A thermal camera may be based on an uncooled thermal sensor, such as a thermopile sensor, a microbolometer sensor (where microbolometer refers to any type of a bolometer sensor and its equivalents), a pyroelectric sensor, or a ferroelectric sensor.

A reference to a "camera" herein may relate to various types of devices. In one example, a camera may be a visible-light camera. In another example, a camera may capture light in the ultra-violet range. In another example, a camera may capture near infrared radiation (e.g., wavelengths between 750 and 2000 nm). And in still another example, a camera may be a thermal camera.

When a camera is inward-facing and head-mounted, challenges faced by systems known in the art that are used to acquire images, which include non-head-mounted cameras, may be simplified and even eliminated with some of the embodiments described herein. Some of these challenges may involve dealing with complications caused by movements of the user, image registration, region of interest (ROI) alignment, tracking based on hot spots or markers, and motion compensation.

The term "temperature sensor" refers to a device that measures temperature and/or temperature change. The temperature sensor may be a contact thermometer (such as a thermistor, a thermocouple), and/or a non-contact thermal cameras (such as a thermopile sensor, a microbolometer sensor, a pyroelectric sensor, or a ferroelectric sensor). Some examples of temperature sensors useful to measure skin temperature include: thermistors, thermocouples, thermoelectric effect, thermopiles, microbolometers, and pyroelectric sensors. Some examples of temperature sensors useful to measure environment temperature include: thermistors, resistance temperature detectors, thermocouples; thermopiles, and semiconductor-based sensors.

The term "movement sensor" refers to a sensor comprising one or more of the following components: a 3-axis gyroscope, a 3-axis accelerometer, and a 3-axis magnetometer. The movement sensor may also include a sensor that measures barometric pressure.

The term "acoustic sensor" refers to a device that converts sound waves into an electrical signal. An acoustic sensor can be a microphone, such as a dynamic microphone that works via electromagnetic induction, a piezoelectric microphone that uses the phenomenon of piezoelectricity, a fiber-optic microphone that converts acoustic waves into electrical signals by sensing changes in light intensity, a Micro-Electrical-Mechanical System (MIMS) microphone (such as silicon MIMS and piezoelectric MIMS), and/or other sensors that measure sound waves, such as described in the following examples: (i) Han, Jae Hyun, et at "Basilar membrane-inspired self-powered acoustic sensor enabled by highly sensitive multi tunable frequency band." Nano Energy 53 (2018): 198-205, describes a self-powered flexible piezoelectric acoustic sensor having high sensitivity, (ii) Rao, Jihong, et al. "Recent Progress in Self-Powered Skin Sensors." Sensors 19.12 (2019): 2763. describes various self-powered acoustic skin sensors, such as an integrated triboelectric nanogenerator (TEND) with a polymer tube that can pick up and recover human throat voice even in an extremely noisy or windy environment, and (iii) Scanlon, Michael V. Acoustic sensor for voice with embedded physiology. Army Research Lab Adelphi Md., 1999, describes a gel-coupled acoustic sensor able to collect information related to the function of the heart, lungs, and changes in voice patterns.

Herein, the term "blood pressure" is indicative of one or more of the following: the systolic blood pressure of the user, the diastolic blood pressure of the user, and the mean arterial pressure (MAP) of the user. It is specifically noted that the term "blood pressure" is not limited to the systolic and diastolic blood pressure pair.

The terms "substance intake" or "intake of substances" refer to any type of food, beverage, medications, drugs, smoking/inhaling, and any combination thereof.

Blood flow in the face can cause certain facial coloration due to concentration of hemoglobin in various vessels such as arterioles, capillaries, and venules. In some embodiments described herein, coloration at a certain facial region, and/or changes thereto (possibly due to varying volume of blood in the certain region at different stages of cardiac pulses), can represent a hemoglobin concentration pattern at the certain region. This pattern can change because of various factors that can affect blood flow and/or vascular dilation, such as the external temperature, core body temperature, the emotional state, consumption of vascular dilating substances, and more. Embodiments described herein utilize analysis of images of the user's face, in which a hemoglobin concentration pattern can be detected, in order to detect various phenomena that may influence facial temperature, such as having a fever, being intoxicated, and/or in order to estimate physiological parameters such as the core body temperature.

In some embodiments, a hemoglobin concentration pattern calculated from images refers to a color mapping of various portions of the area captured in the images (e.g., the mapping provides the colors of different pixels in the images). In one example, the color mapping provides values that are average intensities of one or more colors of the pixels over a period of time during which the images were taken (e.g., values from one or more channels in the images). In another example, the color mapping provides values that are average intensities of one or more colors of the pixels over a period of time during which the images were taken (e.g., values of the maximum of one or more channels in the images). In yet another example, a hemoglobin concentration pattern may be a function of one or more colors (channels) of the pixels over a period of time during which the images were taken.

In other embodiments, a hemoglobin concentration pattern may refer to time series data, such as a sequence of images representing a progression of a pulse wave in the area. Different physiological conditions, such as different skin or core body temperatures or emotional responses, may produce different sequences of representative images, which depend on the structure of the facial blood vessels of the user and their dilation.

In still other embodiments, a hemoglobin concentration pattern may refer to a contour map, representing the extent to which pixels at a certain wavelength (e.g., corresponding to the color red) have at least a certain value. Since the extent of hemoglobin concentration is correlated with an increase in intensity of certain colors (e.g., red), a hemoglobin concentration pattern for more dilated blood vessels will have different contour map than the contour map observed in a hemoglobin concentration pattern for that blood vessels when it is more contracted.

A hemoglobin concentration pattern, such as one of the examples described above, may be calculated, in some embodiments, from images by a computer, such as computer 340 (described below). Optionally, the hemoglobin concentration pattern may be utilized to generate one or more feature values that are used in a machine learning based approach by the computer for various applications, such as detecting fever, calculating core body temperature, detecting intoxication, and/or other applications described below. In other embodiments, the hemoglobin concentration pattern may be utilized to calculate additional values used to represent the extent of facial blood flow and/or extent of vascular dilation, which may be evaluated, e.g., by comparing the extent of blood flow and/or vascular dilation to thresholds in order to detect whether the user has a fever, estimate core body temperature, detect alcohol intoxication, and/or for other applications described herein.

In one embodiment, a hemoglobin concentration pattern may be converted to a value representing the proportion of the area in which the intensities of pixels reach a threshold. In one example, the intensities being evaluated may be average intensities (e.g., average pixel intensities in the images). In another example, the intensities being evaluated may be maximum intensities corresponding to times of systolic peaks (e.g., as determined by detecting the spread of a pulse wave in the area captured in the images, and/or using a reference signal from a different source such as a PPG sensor that is not the camera that captured the images).

In another embodiment, a hemoglobin concentration pattern may be compared with one or more reference hemoglobin concentration patterns that may correspond to specific physiological conditions (e.g., having a fever, not having a fever, or a specific core body temperature). Optionally, the reference patterns may be based on previously taken images of the user, which were taken at times for which the user's core body temperature was known (e.g., based on a measurement using a thermometer). Optionally, similarity of a hemoglobin concentration pattern to a reference pattern may be utilized to generate one or more feature values utilized in a machine learning approach, as described below. Optionally, the extent of similarity of a hemoglobin concentration pattern to a reference pattern may be utilized to determine whether the user has a certain condition (e.g., fever), as described below.

Various embodiments described herein involve a computer that calculates a hemoglobin concentration pattern. Optionally, values in a hemoglobin concentration pattern may be mapped to specific regions on the face, such that the hemoglobin concentration pattern may be considered a layer or grid that can be mapped onto the face in a predetermined manner.

There are various ways in which a hemoglobin concentration pattern may be calculated in embodiments described herein. Optionally, calculating a hemoglobin concentration pattern involves processing the images, for example, in order to accentuate the color of one or more channels in the images, and/or accentuate the changes to colors of one or more channels in the images (e.g., accentuating color changes caused by blood flow from cardiac pulses). Additionally or alternatively, calculating a hemoglobin concentration pattern may involve calculating a representation of the pattern by assigning values to regions in the images and/or to a representation of regions on the face. Optionally, the values may represent extents of one or more color channels at the different regions. Optionally, the values may represent changes to extents of one or more color channels at the different regions. Optionally, the values may include time series data representing temporal changes to extents of one or more color channels at each of at least some of the different regions.

The following are some examples of processing methods that may be applied to images in order to calculate a hemoglobin concentration pattern based on images. In some embodiments, one or more of the processing methods may be applied by the computer before hemoglobin concentration patterns are used for calculations and/or detections (e.g., prior to detecting fever, intoxication, and/or estimating core body temperature). For example, the images may be processed using one or more of the methods described below, prior to their utilization by the computer to calculate hemoglobin concentration patterns used for the calculations and/or detections. In some embodiments, one or more of the processing methods may be applied by the computer as part of the calculations and/or detections. For example, some layers and/or portions of a deep learning network used by the computer for the calculations and/or detections may implement processing operations of the images (which are involved in calculating the hemoglobin concentration patterns), while other portions of the deep learning network are used to perform the calculations and/or detections on values representing the hemoglobin concentration patterns.

Various preprocessing approaches may be utilized in order to assist in calculating hemoglobin concentration patterns based on images. Some non-limiting examples of the preprocessing approaches that may be used include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081, titled "Estimating cardiac pulse recovery from multi-channel source data via constrained source separation". Additionally or alternatively, images may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an iPPG signal from the images are discussed in Zaunseder et at (2018), "Cardiovascular assessment by imaging photoplethysmography a review", Biomedical Engineering 63(5), 617-634. An example of preprocessing that may be used in some embodiments is given in U.S. Pat. No. 9,020,185, titled "Systems and methods for non-contact heart rate sensing", which describes how times-series signals obtained from video of a user can be filtered and processed to separate an underlying pulsing signal by, for example, using an ICA algorithm.

Another approach that may be utilized as part of preprocessing and/or calculation of hemoglobin concentration patterns involves Eulerian video magnification, as described in Wu, Hao-Yu, et at "Eulerian video magnification for revealing subtle changes in the world." ACM transactions on graphics (TOG) 31.4 (2012): 1-8, and also in the hundreds of references citing this reference. The goal of Eulerian video magnification is to reveal temporal variations in videos that are difficult or impossible to see with the naked eye and display them in an indicative manner. This method takes a standard video sequence as input, and applies spatial decomposition, followed by temporal filtering to the frames. The resulting signal is then amplified to reveal hidden information. This method is successfully applied in many applications in order to visualize the flow of blood as it fills the face and also to amplify and reveal small motions.

Yet another approach that may be utilized as part of preprocessing and/or calculation of hemoglobin concentration patterns, in some embodiments, involves accentuating the color of facial flushing in the images. Thus, values representing extents of facial flushing can be used to represent hemoglobin concentration patterns. In one example, facial flushing values are calculated based on applying decorrelation stretching to the images (such as using a three color space), then applying K-means clustering (such as three clusters corresponding to the three color space), and optionally repeating the decorrelation stretching using a different color space. In another example, facial flushing values are calculated based on applying decorrelation stretching to the images (such as using a three color space), and then applying a linear contrast stretch to further expand the color range.

In one embodiment, calculating a hemoglobin concentration pattern may involve assigning values to regions on the face and/or in the images that are binary values. FIG. 1a illustrates an example of a hemoglobin concentration pattern of a sober person where certain regions have a value "0" because the color of the red channel in the certain regions is below a certain threshold, and other regions have a value "1" because the color of the red channel in the other regions is above the threshold. FIG. 1b illustrates an example of the hemoglobin concentration pattern of the same person when intoxicated, and as a result the face is redder in certain locations.

In another embodiment, calculating a hemoglobin concentration pattern may involve assigning values to regions on the face and/or in the images, which are continuous. In one example, in a first hemoglobin concentration pattern, the pattern may include values in a two-dimensional grid corresponding to average intensities and/or maximum intensities of colors from one or more channels. In another example, in a second hemoglobin concentration pattern, the pattern may include values obtained after processing the images using techniques described herein for extracting iPPG signals. Thus, the pattern, in this example, may include values representing statistics of PPG signals at different regions on the face (e.g., the pattern may include values that are the average or maximum of the PPG signals at the different regions). In another example, the pattern may include averages of values of certain fiducial points (e.g., systolic peaks and/or dicrotic notches) extracted from PPG signals at different regions using iPPG techniques known in the art.

In yet another embodiment, calculating a hemoglobin concentration pattern may involve assigning values to regions on the face and/or in the images, which are a time series. In one example, in a hemoglobin concentration pattern, the pattern may include values in a two-dimensional grid, where each position in the gird is a time series that represents a shape of a PPG pulse wave at the location on the face corresponding to the position. Optionally, the time series for the position may be extracted from images corresponding to multiple pulse waves (and thus represent a typical PPG shape of a pulse wave at location on the face).

FIG. 1c is a schematic illustration of components of a system configured to detect fever and/or intoxication (e.g., due to alcohol consumption). In one embodiment, the system includes at least first and second head-mounted inward-facing cameras 332 that take images 333 of respective first and second regions on a user's face. Henceforth, for the sake of brevity, "the first and second head-mounted inward-facing cameras 332" will be referred to as "the cameras 332". Optionally, the cameras 332 are physically coupled to a frame of smartglasses 330. The system also includes a computer 340, which may or may not be physically coupled to the frame of the smartglasses 330. The system may include additional elements such as a movement sensor, an inertial measurement unit (IMU) 342, a skin temperature sensor 343, an environment sensor 344 that is configured to measure temperature and/or humidity of the environment, and/or a user interface 348.

In one embodiment, the computer 340 calculates, based on baseline images captured with the cameras 332 while the user did not have a fever, a baseline pattern comprising values indicative of first and second baseline hemoglobin concentrations at the first and second regions on the user's face, respectively. Additionally, the computer 340 calculates, based on a current set of images captured with the cameras 332, a current pattern comprising values indicative of first and second current hemoglobin concentrations at the first and second regions, respectively. In this embodiment, the computer 340 detects whether the user has a fever based on a deviation of the current pattern from the baseline pattern.

In some embodiments, the user is considered to have a fever if the user's body temperature rises above a predetermined extent beyond the baseline ("normal") body temperature for the user. For example, if the user's body temperature rises by 1.5° C. or more above normal, the user is considered to have a fever. In other embodiments, the user is considered to have a fever if the user's body temperature rises above a predetermined threshold (which may or may not be specific to the user, and may or may not depend on the hour of the day because the normal temperature may be a function of the hour of the day). For example, if the user's body temperature rises above 38° C., the user is considered to have a fever.

In another embodiment, the computer 340 calculates, based on baseline images captured with the cameras 332 while the user was sober, a baseline pattern comprising values indicative of first and second baseline hemoglobin concentrations at the first and second regions on the user's face, respectively. Additionally, the computer 340 calculates, based on a current set of images captured with the cameras 332, a current pattern comprising values indicative of first and second current hemoglobin concentrations at the first and second legions, respectively. In this embodiment, the computer 340 detects whether the user is intoxicated based on a deviation of the current pattern from the baseline pattern.

In some embodiments, the user is considered to be intoxicated (from alcohol) if the user's Blood Alcohol Level (BAC) is above a predetermined threshold. For example, the user may be considered intoxicated if the BAC is above 0.05%, 0.08%, or 0.1%. In other embodiments, the user may be considered intoxicated if the user consumed at least a certain amount of alcohol during a preceding window of time. For example, the user may be considered intoxicated if the user consumed at least two standard drinks (e.g., two bottles of beer with 5% alcohol content) during a period of two hours or less. In still other embodiments, the user may be considered intoxicated if the user is assessed to exhibit behavior consistent with intoxication and/or is considered unable to care for the safety of oneself or others.

The smartglasses 330 are configured to be worn on a user's head. Optionally, various sensors and/or cameras that are physically coupled to the smartglasses 330, e.g., by being attached to and/or embedded in the frame of the smartglasses 330, are used to measure the user while the user wears the smartglasses 330. Optionally, at least some of the sensors and/or cameras that are physically coupled to the smartglasses 330 may be utilized to measure the environment in which the user is in. In one example, the smartglasses 330 are eyeglasses with sensors and electronics attached thereto and/or embedded therein. In another example, the smartglasses 330 may be an extended reality device (i.e., an augmented realty device, a virtual reality device, and/or mixed reality device). In some embodiments, the cameras 332 are physically coupled to the frame of the smartglasses 330.

Each camera from among the cameras 332 is located less than 10 cm from the face of the user (to whose head the cameras are mounted). Additionally, the first and second head-mounted inward-facing cameras 332 are configured to capture images of respective first and second regions on the user's face (i.e., the first camera captures images of the first region and the second camera captures images of the second region). The first and second regions do not completely overlap.

Having multiple inward-facing head-mounted cameras close to the face can confer the advantage of covering many regions on the face, while still having an aesthetic head-mounted system (due to the close distances of the cameras from the face) and stable and sharp images (due to the cameras capturing the same regions even when the user makes angular motions). In some embodiments, the cameras 332 may be at closers distances to the face. In one example, each of the cameras 332 is less than 5 cm from the user's face. In another example, each of the cameras 332 is less than 2 cm from the user's face.

The locations, orientations, and/or optical properties of the first and second head-mounted inward-facing cameras 332 can cause them to capture images of different respective first and second regions. Optionally, each of the first and second regions contains an area of at least 1 cm$^2$ of skin on the user's face. Optionally, each of the first and second regions contains an area of at least 4 cm$^2$ of skin on the user's face.

In some embodiments, the middle of the first region is not at the same location as the middle of the second region. In one example, the middles of the first and second regions are at least 1 cm apart. In another example, the middles of the first and second regions are at least 4 cm apart. In yet another example, the middles of the first and second regions are at least 8 cm apart.

Herein, the middle of a region is the average co-ordinate of points in the region (e.g., when points in the region can be described as residing in a two- or three-dimensional space).

In one example, the first region is located above the user's eyes, and the second region is located below the user's eyes. Optionally, in this example, the first and second regions do not overlap. In another example, the middle of the first region is located less than 4 cm from the vertical symmetric axis of the user's face, and the middle of the second region is located more than 4 cm from the vertical symmetric axis. Optionally, in this example, the first and second regions do overlap.

The first and second head-mounted inward-facing cameras 332 are small and lightweight. In some embodiments, each of the cameras 332 weighs below 10 g and even below 2 g. In one example, each of these cameras is a multi-pixel video camera having a CMOS or a CCD sensor. The video camera may capture images at various rates. In one example, the images 333 include images captured at a frame rate of at least 3 frames per second (fps). In another example, the images 333 include images captured at a frame rate of at least 30 fps. In still another example, the images 333 include images captured at a frame rate of at least 256 fps. Images taken by the cameras 332 may have various resolutions. In one example, the images 333 include images that have a resolution of at least 8×8 pixels. In another example, the images 333 include images that have a resolution of at least 32×32 pixels. In yet another example, the images 333 include images that have a resolution of at least 640×480 pixels.

In some embodiments, at least one of the cameras 332 may capture light in the near infrared spectrum (NIR). Optionally, such a camera may include optics and sensors that capture light rays in at least one of the following NIR spectrum intervals: 700-800 nm, 700-900 nm, 700-1,050 nm. Optionally, the sensors may be CCD sensors designed to be sensitive in the NIR spectrum and/or CMOS sensors designed to be sensitive in the NIR spectrum.

In one example, the cameras 332 are mounted between 5 mm and 50 mm away from the user's head. Examples of camera sensors that are sensitive to wavelengths below 1050 nm include CCD and CMOS sensors, which are sensitive to wavelengths in at least a portion of the range of 350 nm to 1050 nm.

In some embodiments, the system may include an optical emitter configured to direct electromagnetic radiation at the first and/or second regions. Optionally, the optical emitter comprises one or more of the following: a laser diode (LD), a light-emitting diodes (LED), and an organic light-emitting diode (OT FD). It is to be noted that when embodiments described in this disclosure utilize optical emitters directed at a region of interest (ROI), such as an area appearing in images 333, the optical emitter may be positioned in various locations relative to the ROI. In some embodiments, the optical emitter may be positioned essentially directly above the ROI, such that electromagnetic radiation is emitted at an angle that is perpendicular (or within 10 degrees from being perpendicular) relative to the ROI. Optionally, a camera may be positioned near the optical emitter in order to capture the reflection of electromagnetic radiation from the ROI. In other embodiments, the optical emitter may be positioned such that it is not perpendicular to the ROI. Optionally, the optical emitter does not occlude the ROI. In one example, the optical emitter may be located at the top of a frame of a pair of eyeglasses, and the ROI may include a portion of the forehead. In another example, optical emitter may be located on an arm of a frame of a pair of eyeglasses and the ROI may be located above the arm or below it.

Due to the position of the cameras 332 relative to the face, in some embodiments, there may be an acute angle between the optical axis of a camera from among these cameras and the area captured by images taken by said camera (e.g., when the camera is fixed to an eyeglasses frame and the area is on, and/or includes a portion of, the forehead or a cheek). In order to improve the sharpness of images captured by said camera, the camera may be configured to operate in a way that takes advantage of the Scheimpflug principle. In one embodiment, a camera from among the cameras 332 includes a sensor and a lens; the sensor plane is tilted by a fixed angle greater than 2° relative to the lens plane according to the Scheimpflug principle in order to capture a sharper image when the smartglasses are worn by the user (where the lens plane refers to a plane that is perpendicular to the optical axis of the lens, which may include one or more lenses). In another embodiment, the camera includes a sensor, a lens, and a motor, the motor tilts the lens relative to the sensor according to the Scheimpflug principle. The tilt improves the sharpness of images when the smartglasses are worn by the user. Additional details regarding the application of the Scheimpflug principle are discussed further below.

In some embodiments, the system may include a shortwave infrared (SWIR 334) inward-facing head-mounted camera that is configured to detect wavelengths in at least a portion of the range of 700 nm to 2500 nm. One example of a SWIR sensor suitable for this embodiment is Indium Gallium Arsenide (inGaAs) sensor. Optionally, the computer 340 is configured to detect whether the user has the fever also based on a deviation of a current SWIR pattern from a baseline SWIR pattern taken while the user did not have a fever. Optionally, the current SWIR pattern is generated based on images taken with the SWIR 334 at a current time, while the baseline SWIR pattern is generated based on SWIR-images 335 taken with the SWIR 334 during one or more previous periods, while the user did not have a fever. In some embodiments, at least some of the feature values, described further below, which are generated based on images from among the images 333 may be generated for the SWIR-images 335. Thus, SWIR-images 335 may be utilized, in some embodiments, as inputs for a detection of whether the user has a fever and/or is intoxicated.

Variations in the reflected ambient light may introduce artifacts into images collected with inward facing cameras that can add noise to these images and make detections and/or calculations based on these images less accurate. In some embodiments, the system includes an outward-facing camera, which is coupled to the smartglasses, and takes images of the environment. Optionally, this outward facing camera is located less than 10 cm from the user's face and weighs below 5 g. Optionally, the outward-facing camera may include optics that provide it with a wide field of view.

The computer 340 is configured, in some embodiments, to detect a certain condition (e.g., whether the user has a fever or whether the user is intoxicated) based on a deviation of a current pattern from a baseline pattern.

In different embodiments, a reference to "the computer 340" may refer to different components and/or a combination of components. In some embodiments, the computer 340 may include a processor located on a head-mounted device, such as the smartglasses 330. In other embodiments, at least some of the calculations attributed to the computer 340 may be performed on a remote processor, such as the user's smartphone and/or a cloud-based server. Thus, references to calculations being performed by the "computer 340" should be interpreted as calculations being performed utilizing one or more computers, with some of these one or more computers possibly being of a head-mounted device to which the cameras 332 are coupled.

The current pattern is calculated, by the computer 340, based on current images, from among the images 333, captured by the cameras 332. The current images are taken during some times that fall during a window leading up to a current time. Optionally, the window is at most five second long. Optionally, the window is at most 30 seconds long. Optionally, the window is at most 5 minutes long. Optionally, the window is at most one hour long. The current images taken during the window are utilized by the computer 340 to calculate the current pattern, which is indicative of at least first and second current hemoglobin concentrations at the first and second legions, respectively. It is to be noted that images taken during the window need not be taken continuously throughout the window, rather they may be taken intermittently or sporadically during the window.

As discussed below, extents of reflection and absorption of light through the skin may depend on the wavelength of the light. Thus, in some embodiments, patterns of hemoglobin concentration may include values calculated based on different channels of the same images. Thus, in the detection of fever and/or intoxication, the baseline pattern and/or current pattern may include multiple sets of values derived from multiple different channels.

The baseline pattern is calculated, by the computer 340, based on baseline images from among the images 333, captured by the cameras 332. Optionally, the baseline images were taken previously (prior to when the current images were taken) while the user was not in a state being detected. In one embodiment, in which the computer 340 detects whether the user has a fever, the baseline images were taken while the user did not have a fever. In another embodiment, in which the computer 340 detects whether the user is intoxicated, the baseline images were taken while the user was sober (or assumed to be sober).

Windows during which baseline images were taken may have different lengths, and end prior to the current time. Optionally, windows during which baseline images are taken end before the current window begins. In one example, the baseline images may have been taken at different times during a window spanning several hours. In another example, the baseline images include images taken at different times during a window spanning several days/weeks/months, such that the baseline images include images taken on different days/weeks/months, respectively.

In some embodiments, the computer 340 may receive indications indicative of times in which the user is in a baseline state (e.g., without a fever or not intoxicated). Optionally, at least some of the baseline images are selected based on the indications. For example, images taken by the cameras 332 are included in the baseline images if there is an indication indicating the user was in a baseline state within temporal proximity to when they were taken. In one example, images taken within a window spanning from an hour before to an hour after a time for which there is an indication that the user was in a baseline state, are included in the baseline images. In another example, images taken within a window spanning from five minutes before to five minutes after a time for which there is an indication that the user was in a baseline state, are included in the baseline images. In yet another example, images taken within a window spanning from 30 seconds before to 30 seconds after a time for which there is an indication that the user was in a baseline state, are included in the baseline images.

The indications indicative of the times in which the user is in a baseline state may come from one or more sources. In some embodiments, indications may be self-reported. For example, the user may provide indications indicating when he/she were sober and/or without a fever. In other embodiments, some other person such as a caregiver, physician, supervisor, and/or guardian may provide such indications. In still other embodiments, indications may be received from sensors that measure the user, which are not the cameras 332. In one example, temperature measurements taken by an oral thermometer and/or a non-head-mounted thermal camera are used to determine whether the user has a fever. In another example, analysis of the user's movements (e.g., as measured by the IMU 342) and/or voice patterns (as recorded with microphones) are used to determine whether the user is intoxicated or not (e.g., using machine learning methods known in the art).

In some embodiments, images taken in a certain context are assumed to be taken in a baseline state. In one example, images taken in the daytime at school/work, while the user behaved as expected from a sober/healthy person, are assumed to be taken while the user was not intoxicated and/or without a fever. In another example, all images taken while there is no indication that the user was not in a baseline state, are assumed to be taken in the baseline state. In this example, it may be assumed (for most normative people) that most of the time the user does not have a fever and/or is not intoxicated.

The baseline images are utilized by the computer 340 to calculate the baseline pattern, which is indicative of at least first and second baseline hemoglobin concentrations at the first and second regions, respectively. In one example, the baseline pattern is indicative of first and second baseline hemoglobin concentrations at the first and second regions characteristic of times at which the user does not have a fever, or is not intoxicated.

In addition to a baseline pattern indicating hemoglobin concentrations characteristic of times in which the user is in a baseline state, in some embodiments, the computer 340 may utilize a detected-state pattern indicating hemoglobin concentrations characteristic of times in which the user is in the detected state (e.g., has a fever and/or is intoxicated). Optionally, detection of whether the user is in the detected state is done by a deviation of the current pattern from the detected-state pattern. Optionally, the detected-state pattern is calculated by the computer 340 based on additional images, from among the images 333, taken at times at which there was an indication that the user was in a certain state (e.g., had a fever and/or was intoxicated). Optionally, the indications may be self-reported, provided by another person, and/or a result of analysis of sensor measurements, as described above.

In one embodiment, the computer 340 calculates, based on additional baseline images captured with the cameras 332 while the user had a fever, a fever-baseline pattern comprising values indicative of first and second fever hemoglobin concentrations at the first and second regions, respectively. The computer 340 then bases the detection of whether the user has the fever also on a deviation of the current pattern from the fever-baseline pattern (in addition to the deviation from the baseline pattern).

In one embodiment, the computer 340 calculates, based on additional baseline images captured with the cameras 332 while the user was intoxicated, an intoxication baseline pattern comprising values indicative of first and second intoxication hemoglobin concentrations at the first and second regions, respectively. The computer 340 then bases the detection of whether the user is intoxicated also based on a deviation of the current pattern from the intoxication-baseline pattern in addition to the deviation from the baseline pattern).

Detection of reflections of light at different wavelengths can be used to account for thermal interference by the environment. In some embodiments, accounting for thermal inference relies on the following three observations:
(i) blue and green wavelengths penetrate the skin less deeply compared to red and near-infrared wavelengths, (ii) the capillaries are closer to the skin surface compared to the arterioles, and (iii) the PPG amplitude is proportional to the skin temperature, probably because both blood viscosity and vasoconstriction increase with the increase in skin temperature. Additionally, we will examine the ratio $R_{depth}$, which is defined as follows $$R_{depth} = \frac{\text{reflected light from the capillaries}}{\text{reflected light from the arterioles}}$$

Based on the aforementioned observations, it is to be expected that $R_{depth}$ will be greater for the blue and green wavelengths compared to the red and near-infrared wavelengths. This means that temperature interference from the environment is expected to influence the hemoglobin concentration pattern derived from the blue and green wavelengths more than it influences the hemoglobin concentration pattern derived from the red and near-infrared wavelengths.

In one embodiment, because environment heating increases vasodilation whilst environment cooling decreases blood flow to the skin, and because temperature interference from the environment is expected to influence a hemoglobin concentration pattern derived from the blue and/or green wavelengths more than it influences a hemoglobin concentration pattern derived from the red and/or near-infrared wavelengths, the system can improve its accuracy when estimating temperatures, such as the core body temperature and/or detecting fever based on the level of discrepancy between (i) a hemoglobin concentration pattern derived from a first channel corresponding to wavelengths mostly below 580 nanometers, such as the blue and/or green reflections, and (ii) the hemoglobin concentration pattern derived from a second channel corresponding to wavelengths mostly above 580 nanometers, such as the red and/or near-infrared reflections.

It is noted that most optical filters are not perfect, and the meaning of the sentence "channel corresponding to wavelengths mostly below 580 nanometers" is that the filter suppresses red and near-infrared at least twice as much, compared to blue and/or green. Similarly, the meaning of the sentence "channel corresponding to wavelengths mostly above 580 nanometers" is that the filter suppresses blue and green at least twice as much, compared to red and/or near-infrared.

For example, when a temperature corresponding to hemoglobin concentration pattern derived from the blue and/or green wavelengths is higher than a predetermined threshold compared to a temperature corresponding to the hemoglobin concentration pattern derived from the red and/or near-infrared wavelengths, this may indicate that the user is in a hot environment (such as being close to a heater or in direct sunlight), and/or that the user has just arrived from a hot environment (such as entering a cold building from a hot sunnier street). In another example, when a temperature corresponding to hemoglobin concentration pattern derived from the blue and/or green wavelengths is lower than a predetermined threshold from the temperature corresponding to the hemoglobin concentration pattern derived from the red and/or near-infrared wavelengths, this may indicate that the user is in a cold environment, and/or that the user is being exposed to a wind that cools the skin.

In one embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. Optionally, the current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Having separate values for different wavelengths enables to account for interference from the environment when detecting whether the user has the fever because temperature interference from the environment is expected to affect the third values more than it affects the fourth values.

In another embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. The current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Optionally, the computer 340 calculates a confidence in a detection of the fever based on the deviation of the current pattern from the baseline pattern, such that the confidence decreases as the difference between the third values and the fourth values increases. For example, the confidence is a value proportional to said deviation. Having separate values for different wavelengths enables to account for interference from the environment when calculating said confidence because temperature interference from the environment is expected to affect the third values more than it affects the fourth values.

There are various computational approaches that may be utilized by the computer 340 in order to detect whether the user has a fever, and/or is intoxicated, based on a deviation of a current pattern from a baseline pattern.

In one embodiment, the computer 340 calculates a value indicative of a magnitude of the deviation of the current pattern from the baseline pattern. For example, when both patterns include numerical values, the values in corresponding regions in both patterns may be subtracted from each other. In FIG. 1a and FIG. 1b, this may be interpreted as calculating the difference in the number of "1"s in both patterns. Optionally, if the subtraction of the baseline pattern from the current pattern reaches a certain threshold, the user is assumed to be in a certain state (e.g., has a fever and/or is intoxicated).

In another embodiment, the computer 340 calculates a value indicative of the deviation between the current pattern and the baseline pattern based on vector representations of the patterns. For example, if each of the patterns may be represented as a vector in a multi-dimensional space, the deviation may be calculated using one or more techniques known in the art for calculating distances between vectors, such as a dot product, Euclidean distance, or a distance according to some other norm. Optionally, if the distance has at least a certain value, the user is assumed to be in a certain state (e.g., has a fever and/or is intoxicated).

In yet another embodiment, if the difference between a vector representation of the current pattern and a vector representation of the baseline pattern is in a certain direction, the computer 340 detects the user is in a certain state corresponding to the certain direction. For example, there may be a predetermined direction of change for patterns when the user becomes intoxicated.

In still another embodiment, in which the current pattern and the baseline pattern include time series data, the computer 340 utilizes methods known in the art for comparison of time series, such as dynamic time warping, in order to calculate an extent of deviation of the current pattern from the baseline pattern.

In some embodiments, the computer 340 may utilize the fever-baseline pattern and/or the intoxication-baseline pattern, which are discussed above, in order to detect whether the user has a fever and/or is intoxicated. In one example, if the current pattern is more similar to the fever-baseline pattern than it is to the baseline pattern, the computer 340 detect the user has a fever. In another example, if a first difference between the current pattern and the intoxication-baseline pattern is below a first threshold, while a second difference between the current pattern and the baseline pattern is above a second threshold, the computer 340 detects the user is intoxicated.

Detection of whether the user has a fever and/or is intoxicated may involve utilization of machine learning approaches. In some embodiments, baseline images and/or current images may be utilized by the computer 340 to generate feature values that are used in a machine learning based approach by the computer 340 to detect whether the user has a fever and/or is intoxicated. In some embodiments, the computer 340 calculates the feature values based on data that includes at least some of the images 333 (and possibly other data) and utilizes a model 346 to calculate, based on the feature values, a value indicative of whether the user has a fever and/or a value indicative of whether the user is intoxicated.

In one embodiment, the value calculated by the computer 340 based on the feature values is a binary value. For example, the value is "1" if the user has a fever and "0" if the user does not have a fever. In some embodiments, the value calculated by the computer 340 based on the feature values is a scalar. For example, the calculated value may be an estimation of the user's core body temperature and/or an estimation of the increase of the user's core body temperature. In such embodiments, if the calculated value reaches a threshold, the user is considered to have a fever. In a similar fashion, a binary value may be calculated in the case of intoxication, and detecting intoxication may be done if a calculated value indicative of an intoxication level of the user reaches a predetermined threshold.

Generally, machine learning-based approaches utilized by embodiments described herein involve training a model on samples, with each sample including: feature values generated based on images taken by the cameras 332, and optionally other data, which were taken during a certain period, and a label indicative of an extent of fever and/or intoxication (during the certain period). Optionally, a label may be provided manually by the user and/or other sources described above as providing indications about the state of the user (e.g., indications of a fever level and/or intoxication level, described above). Optionally, a label may be extracted based on analysis of electronic health records of the user, generated while being monitored at a medical facility.

In some embodiments, the model 346 may be personalized for a user by training the model on samples that include: feature values generated based on measurements of the user, and corresponding labels indicative of the extent of fever and/or intoxication of the user while the measurements were taken. In some embodiments, the model 346 may be generated based on measurements of multiple users, in which case, the model 346 may be considered a general model. Optionally, a model generated based on measurements of multiple users may be personalized for a certain user by being retrained on samples generated based on measurements of the certain user.

There are various types of feature values that may be generated by the computer 340 based on input data, which may be utilized to calculate a value indicative of whether the user has a fever and/or is intoxicated. Some examples of feature values include "raw" or minimally processed values based on the input data (i.e., the features are the data itself or applying generic preprocessing functions to the data). Other examples of feature values include feature values that are based on higher-level processing, such a feature values determined based on domain-knowledge. In one example, feature values may include values of the patterns themselves, such as values included in the current pattern, the baseline pattern, the fever-baseline pattern, and/or the intoxication-baseline pattern. In another example, feature values may include values that are functions of patterns, such as values that represent a deviation of the current pattern from the baseline pattern.

In one non-limiting example, feature values generated by the computer 340 include pixel values from the images 333. In another non-limiting example, feature values generated by the computer 340 include timings and intensities corresponding to fiducial points identified in iPPG signals extracted from the images 333. In yet another non-limiting example, feature values generated by the computer 340 include binary values representing the baseline pattern and the current pattern.

The following are some examples of the various types of feature values that may be generated based on images from among the images 333 by the computer 340. In one embodiment, one or more of the feature values may be various low-level features derived from images, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may derived from multiple images taken at different times, such as volume local binary patterns (VLBP), cuboids, and/or optical strain-based features. In one example, one or more of the feature values may represent a difference between values of pixels at one time t at a certain location on the face and values of pixels at a different location at some other time t+x (which can help detect different arrival times of a pulse wave).

In some embodiments, at least some feature values utilized by the computer 340 describe properties of the cardiac waveform in an iPPG signal derived from images from among the images 333. To this end, the computer 340 may employ various approaches known in the art to identify landmarks in a cardiac waveform (e.g., systolic peaks, diastolic peaks), and/or extract various types of known values that may be derived from the cardiac waveform, as described in the following examples.

In one embodiment, at least some of the feature values generated based on the iPPG signal may be indicative of waveform properties that include: systolic-upstroke time, diastolic time, and the time delay between the systolic and diastolic peaks, as described in Samna, Rohan, et al. "Non-invasive cuffless estimation of blood pressure using Photoplethysmography without electrocardiograph measurement." 2014 IEEE REGION 10 SYMPOSIUM. IEEE, 2014.

In another embodiment, at least some of the feature values generated based on the iPPG signal may be derived from another analysis approach to PPG waveforms, as described in US Patent Application US20180206733, entitled "Device, method and system for monitoring and management of changes in hemodynamic parameters". This approach assumes the cardiac waveform has the following structure: a minimum/starting point (A), which increases to a systolic peak (B), which decreases to a dicrotic notch (C), which increases to a dicrotic wave (D), which decreases to the starting point of the next pulse wave (E). Various features that may be calculated by the computer 340, which are suggested in the aforementioned publication, include: value of A, value of B, value of C, value of D, value of E, systol area that is the area under ABCE, diastol area that is the area under CDE, and the ratio between BC and DC.

In still another embodiment, the computer 340 may utilize the various approaches described in Elgendi, M. (2012), "On the analysis of fingertip photoplethysmogram signals", Current cardiology reviews, 8(1), 14-25, in order to generate at least some of the feature values bases on the iPPG signal. This reference surveys several preprocessing approaches for PPG signals as well as a variety of feature values that may be utilized. Some of the techniques described therein, which may be utilized by the computer 340, include calculating feature values based on first and second derivatives of PPG signals.

In some embodiments, at least some of the feature values may represent calibration values of a user, which are values of certain parameters such as waveform properties described above when the user had a known state (e.g., while it was known that the user was without a fever and/or sober).

In some embodiments, the computer 340 may utilize one or more feature values indicative of the user's heart rate. Optionally, these feature values may be derived from images from among the images 333, e.g., by performing calculations on iPPG signals extracted from the images. In one example, a time series signal is generated from video images of a subject's exposed skin, and a reference signal is used to perform a constrained source separation (which is a variant of ICA) on the time series signals to obtain the PPG signal; peak-to-peak pulse points are detected in the PPG signal, which may be analyzed to determine parameters such as heart rate, heart rate variability, and/or to obtain peak-to-peak pulse dynamics.

In some embodiments, one or more of the feature values utilized by the computer 340 to calculate a value indicative of whether the user has a fever and/or is intoxicated may be generated based on additional inputs from sources other than the cameras 332.

Stress is a factor that can influence the diameter of the arteries, and thus influence the blood flow and resulting hemoglobin concentration patterns. In one embodiment, the computer 340 is further configured to: receive a value indicative of a stress level of the user, and generate at least one of the feature values based on the received value. Optionally, the value indicative of the stress level is obtained using a thermal camera. In one example, the system may include an inward-facing head-mounted thermal camera configured to take measurements of a periorbital region of the user, where the measurements of a periorbital region of the user are indicative of the stress level of the user. In another example, the system includes an inward facing head-mounted thermal camera configured to take measurements of a region on the forehead of the user, where the measurements of the region on the forehead of the user are indicative of the stress level of the user. In still another example, the system includes an inward facing head-mounted thermal camera configured to take measurements of a region on the nose of the user, where the measurements of the region on the nose of the user are indicative of the stress level of the user.

Hydration is a factor that affects blood viscosity, which can affect the speed at which blood flows in the body, and consequently may affect blood flow and hemoglobin concentration patterns. In one embodiment, the computer 340 is further configured to: receive a value indicative of a hydration level of the user, and generate at least one of the feature values based on the received value. Optionally, the system includes an additional camera configured to detect intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer 340 as values indicative of the hydration level of the user.

Momentary physical activity can affect the blood flow of the user (e.g., due to the increase in the heart rate that it involves). In order to account for this factor, in some embodiments, the computer 340 may generate one or more feature values representing the extent of the user's movement from measurements of the IMU 342.

The user's skin temperature may affect blood viscosity, thus it may influence facial hemoglobin concentration patterns. Some embodiments may include the skin temperature sensor 343, which may be a head-mounted sensor. The skin temperature sensor 343 measures temperature of a region comprising skin on the user's head ($T_{skin}$). Optionally, the computer 340 generates one or more feature values based on $T_{skin}$, such as feature values indicating average skin temperature or a difference from baseline skin temperature.

The temperature and/or humidity in the environment may also be a factor that is considered in some embodiments. The temperature and/or humidity level in the environment can both impact the user's skin temperature and cause a physiologic response involved in regulating the user's body temperature, which may affect observed hemoglobin concentration patterns. Some embodiments may include the environment sensor 344, which may optionally, be head-mounted (e.g., physically coupled to smartglasses). The environment sensor 344 measures an environmental temperature and/or humidity. In one embodiment, the computer 340 may generate one or more feature values based on the temperature and/or humidity in the environment, such as feature values indicating average environment temperature and/or humidity, maximal environment temperature and/or humidity, or a difference from baseline environment temperature and/or humidity.

Training the model 346 may involve utilization of various training algorithms known in the art (e.g., algorithms for training neural networks, and/or other approaches described herein). After the model 346 is trained, feature values may be generated for certain measurements of the user (e.g., current images and baseline images), for which the value of the corresponding label (e.g., whether the user has a fever and/or whether the user is intoxicated) is unknown. The computer 340 can utilize the model 346 to calculate a value indicative of whether the user has a fever and/or whether the user is intoxicated, based on these feature values.

In some embodiments, the model 346 may be generated based on data that includes measurements of the user (i.e., data that includes images taken by the cameras 332). Additionally or alternatively, in some embodiments, the model 346 may be generated based on data that includes measurements of one or more other users (such as users of different ages, weights, sexes, body masses, and health states). In order to achieve a robust model, which may be useful for detecting fever and/or intoxication in various conditions, in some embodiments, the samples used to train the model 346 may include samples based on measurements taken in different conditions. Optionally, the samples are generated based on measurements taken on different days, while in different locations, and/or while different environmental conditions persisted. In a first example, the model 346 is trained on samples generated from a first set of measurements taken while the user was indoors and not in direct sunlight, and is also trained on other samples generated from a second set of measurements taken while the user was outdoors, in direct sunlight. In a second example, the model 346 is trained on samples generated from a first set of measurements taken during daytime, and is also trained on other samples generated from a second set of measurements taken during nighttime. In a third example, the model 346 is trained on samples generated from a first set of measurements taken while the user was moving, and is also trained on other samples generated from a second set of measurements taken while the user was sitting.

Utilizing the model 346 to detect whether the user has a fever and/or whether the user is intoxicated may involve computer 340 performing various operations, depending on the type of model. The following are some examples of various possibilities for the model 346 and the type of calculations that may be accordingly performed by the computer 340, in some embodiments, in order to detect whether the user has a fever and/or whether the user is intoxicated: (a) the model 346 comprises parameters of a decision tree. Optionally, the computer 340 simulates a traversal along a path in the decision tree, determining which branches to take based on the feature values. A value indicative of whether the user has a fever and/or whether the user is intoxicated may be obtained at the leaf node and/or based on calculations involving values on nodes and/or edges along the path; (b) the model 346 comprises parameters of a regression model (e.g., regression coefficients in a linear regression model or a logistic regression model). Optionally, the computer 340 multiplies the feature values (which may be considered a regressor) with the parameters of the regression model in order to obtain the value indicative of whether the user has a fever and/or whether the user is intoxicated; and/or (c) the model 346 comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 340 provides the feature values as inputs to the neural network, computes the values of the various activation functions and propagates values between layers, and obtains an output from the network, which is the value indicative of whether the user has a fever and/or whether the user is intoxicated.

In some embodiments, a machine learning approach that may be applied to calculating a value indicative of whether the user has a fever and/or whether the user is intoxicated based on images may be characterized as "deep learning" In one embodiment, the model 346 may include parameters describing multiple hidden layers of a neural network. Optionally, the model may include a convolution neural network (CNN). In one example, the CNN may be utilized to identify certain patterns in the video images, such as hemoglobin concentration patterns. Due to the fact that calculations are performed on sequences images display a certain pattern of change over time (i.e., across multiple frames), these calculations may involve retaining state information that is based on previous images in the sequence. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In addition to detecting whether the user has a fever and/or whether the user is intoxicated, in some embodiments, the computer 340 may utilize the images 333 to detect additional physiological signals and/or conditions.

In one embodiment, the computer 340 calculates, based on the current set of images, a current heart rate and/or a current respiration rate of the user. For example, the computer 340 may utilize one or more techniques described herein or known in the art for calculating heart rate and/or respiration from iPPG signals. The computer 340 can then utilize the current heart rate and/or the current respiration rate of the user, to detect whether the user has a fever, and other conditions such as hyperthermia or hypothermia, also based on deviations of the current heart rate and/or the current respiration rate from a baseline heart rate and/or baseline respiration rate of the user, respectively. In one example, the computer 340 may utilize a machine learning approach similar to the one described above, but instead of using the model 346, the computer 340 uses a different model trained with labels corresponding to extents of hyperthermia or hypothermia (using feature values similar to the ones described above with respect to the model 346).

In another embodiment, the computer 340 may utilize one or more calibration measurements of the user's core body temperature, taken by a different device (e.g., a thermometer), prior to a certain time, to calculate the user's core body temperature based on a certain set of images that were taken by the cameras 332 after the certain time. For example, the computer 340 may utilize a model trained similarly to the model 346, but also includes feature values describing patterns observed for known core body temperatures. In another example, the calibration measurements can be used to adjust values predicted by the computer 340 when making estimations of the extent of fever using the model 346.

In one embodiment, the computer 340 calculates the user's core body temperature based on the deviation of the current pattern from the baseline pattern. For example, in this embodiment, the model 346 is trained with labels that are indicative of the user's core body temperature.

In yet another embodiment, the computer 340 may detect blushing based on the deviation of the current pattern from the baseline pattern. In one example, the computer 340 may utilize a machine learning approach similar to the one described above, but instead of using the model 346, the computer 340 uses a different model trained with labels corresponding to extents of blushing by the user. In this example, blushing may be identified using image analysis techniques known in the art.

The user interface 348 may be utilized to present values calculated by the computer 340, such as indications whether the user has a fever or whether the user is intoxicated. Optionally, the user interface 348 is a component of a device of the user, such as a smartphone's screen or an augmented reality display.

In one embodiment, the computer 340 detects blushing based on the deviation of the current pattern from the baseline pattern, and presents an alert to the user about the blushing via the user interface 348. In one example, the computer 340 provides a biofeedback for the user to enable the user to learn to control the blushing. Optionally, the biofeedback updates the user about the level of blushing in real time, and by that increases the awareness of the user to the blushing and gradually enables the user to learn to control his/her blushing.

In another embodiment, the computer 340 enables the user to share an intoxication history of the user, upon receiving a permission from the user. For example, the user may be able to decide to share his/her intoxication history with a certain person in order to increase the trust, or not share his/her intoxication history with the certain person if the certain persons does not share in return his/her intoxication history with the user.

The following is an additional embodiment of a system configured to detect alcohol intoxication. This embodiment includes memory, a communication interface, and a processor. The processor is configured to: receive baseline images of a user's face, captured by a video camera while the user was sober; calculate, based on the baseline images, a baseline hemoglobin concentration pattern comprising at least 3 points indicative of hemoglobin concentrations on the user's face; receive current images of the user, calculate, based on the current images, a current hemoglobin concentration pattern comprising the at least 3 points indicative of hemoglobin concentrations on the user's face; and detect whether the user is intoxicated based on a deviation of the current hemoglobin concentration pattern from the baseline hemoglobin concentration pattern. Optionally, the video camera is an inward-facing head-mounted camera (HCAM) that is mounted more than 5 mil away from the user's head and is sensitive to wavelengths below 1050 nanometer.

The following method for detecting fever may be used by systems modeled according to FIG. 1c. The steps described below may be performed by conning a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, receiving, from first and second inward-facing head-mounted cameras (Cam$_{1\&2}$) sensitive to wavelengths below 1050 nanometer, images of respective first and second regions on a user's face. Optionally, the middles of the first and second regions are at least 4 cm apart. In Step 2, calculating, based on baseline images captured with Gamma while the user did not have a fever, a baseline pattern comprising values indicative of first and second baseline hemoglobin concentrations at the first and second regions, respectively. In Step 3, calculating, based on a current set of images captured with Cam$_{1\&2}$, a current pattern comprising values indicative of first and second current hemoglobin concentrations at the first and second regions, respectively. And in Step 4, detecting whether the user has a fever based on a deviation of the current pattern from the baseline pattern.

In one embodiment, the method for detecting fever optionally includes the following steps: calculating, based on additional baseline images captured with Cam$_{1\&2}$ while the user had a fever, a fever-baseline pattern comprising values indicative of first and second fever hemoglobin concentrations at the first and second regions, respectively; and basing the detecting of whether the user has the fever also on a deviation of the current pattern from the fever-baseline pattern.

In one embodiment, the baseline images and the current set of images comprise a first channel corresponding to wavelengths that are mostly below 580 nanometers and a second channel corresponding to wavelengths mostly above 580 nanometers; the baseline pattern comprises: (i) first values, derived based on the first channel in the baseline images, which are indicative of the first and second baseline hemoglobin concentrations at the first and second regions, respectively, and (ii) second values, derived based on the second channel in the baseline images, which are indicative of third and fourth baseline hemoglobin concentrations at the first and second regions, respectively. The current pattern comprises: (i) third values, derived based on the first channel in the current set of images, which are indicative of the first and second current hemoglobin concentrations at the first and second regions, respectively, and (ii) fourth values, derived based on the second channel in the current set of images, which are indicative of third and fourth current hemoglobin concentrations at the first and second regions, respectively. Optionally, method for detecting fever includes a step of calculating a confidence in a detection of the fever based on the deviation of the current pattern from the baseline pattern, such that the confidence decreases as the difference between the third values and the fourth values increases.

Figure 1D:
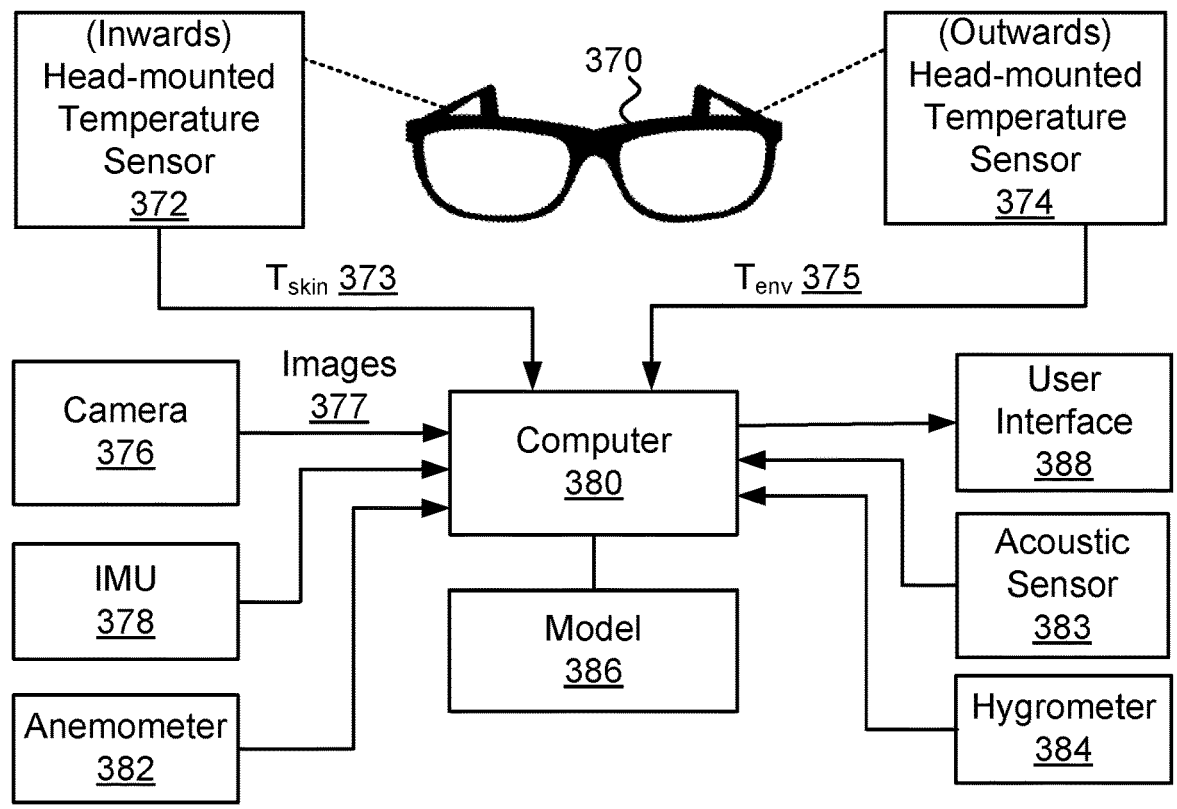
FIG. 1d is a schematic illustration of components of additional embodiments of a system to detect fever and/or intoxication.

FIG. 1d is a schematic illustration of components of additional embodiments of a system configured to detect fever and/or intoxication (e.g., due to alcohol consumption). In one embodiment, a system that detects fever includes at least a first head-mounted temperature sensor 372 that is configured to measure skin temperature (T$_{skin}$ 373) at a first region on a user's head, and a second head-mounted temperature sensor 374 that is configured to measure a temperature of the environment (T$_{env}$ 375). Optionally, the first region covers a portion of skin that is not located above a portion of a branch of the external carotid artery. Optionally, these temperature sensors are physically coupled to a frame of smartglasses 370. The system also includes a computer 380, which may or may not be physically coupled to the frame of the smartglasses 370. The system may include additional elements such as a movement sensor (e.g., inertial measurement unit (IMU) 378), a camera 376 that is sensitive to wavelengths below 1050 nanometer, an anemometer 382, an acoustic sensor 383, a hygrometer 384, and/or a user interface 388.

In one embodiment, the computer 380, receives images 377 of a second region on the user's face, captured by the camera 376, and calculates, based on the images 377, values indicative of hemoglobin concentrations at three or more regions on the user's face. The computer 380 then detects whether the user has a fever based on T$_{skin}$ 373, T$_{env}$ 375, and the values. Additionally or alternatively, the computer 380 may detect whether the user was sober, based on T$_{skin}$ 373, T$_{env}$ 375, and the values.

Various configurations of sensors may be utilized in embodiments described herein to measure various regions on the user's face. In one embodiment, the first region at which T$_{skin}$ 373 are measured, covers a portion of skin that is not located above a portion of a branch of the external carotid artery. In another embodiment, the second head-mounted temperature sensor 374 is an outward facing thermal camera configured to measure levels of radiation directed at the user's head.

In still another embodiment, the first head-mounted temperature sensor 372 is a contact temperature sensor (e.g., a thermistor), the second region is larger than 3 cm$^2$, and the camera 376 is not head-mounted. Optionally, in this embodiment, the camera 376 captures images 377 from a distance that is farther than 5 cm from the user's head. Some examples of cameras that are not head-mounted that may be used in this embodiment include a smartphone camera, a laptop camera, a webcam, and a security camera.

In yet another embodiment, the first head-mounted temperature sensor 372 may include an inward-facing thermal camera located more than 2 mm away from the user's head, the second region is larger than 2 cm$^2$, and the camera 376 is an inward-facing head-mounted camera that captures the images 377 from a distance between 5 mm and 5 cm from the user's head.

In one example, the first head-mounted temperature sensor 372 is physically coupled to the frame of the smartglasses 370, and the first region is located on the user's nose or temple. In another example, the first head-mounted temperature sensor 372 is physically coupled to a helmet or goggles, and the first region is located on the user's forehead, cheekbone, and/or temple.

The temperature of the environment may be measured by a head-mounted sensor and/or by a sensor that is not head-mounted. In some cases, the region that includes skin on the user's head may have a different temperature from another region that includes skin below the user's head. For example, when sitting nearby a window where the head is exposed to direct sunlight while the hands are not exposed to the direct sunlight, or when sitting nearby a heater where the head and certain lower parts of the body absorb different amounts of directed infrared radiation. In such cases, utilizing a head-mounted temperature sensor to measure the temperature of the environment is preferred over a non-head mounted temperature sensor to measure the temperature of the environment.

Examples of possible embodiments for a sensor that measures the temperature of the environment include: (i) a head-mounted non-contact temperature sensor, such as a thermopile or a microbolometer sensor, (ii) a head-mounted contact temperature sensor, such as a thermistor or a thermocouple, (iii) a wearable sensor that is not head-mounted, which may utilize a contact and/or a non-contact sensor, and/or (iv) a non-wearable sensor which may utilize a contact and/or a non-contact sensor.

In some embodiments, in which the camera 376 is an inward-facing head-mounted camera, the camera 376 may have the same properties as other inward-facing head-mounted cameras described herein, such as the cameras 332. In some embodiments, the images 377 may have various properties that are attributed herein to images taken with visible-light cameras, such as the properties attributed to the images 333. Optionally, the images 377 may be processed in various ways described herein for image processing. For example, the computer 380 may utilize one or more of the techniques described with regards to processing the images 333, in order to assist in calculating hemoglobin concentration patterns.

In some embodiments, various processing procedures known in the art, such as face tracking, image recognition, and/or facial landmark discovery may be utilized to process the images 377. Optionally, these procedures are applied when the camera 376 is not a head-mounted camera.

The computer 380 is configured, in some embodiments, to detect a certain condition (e.g., whether the user has a fever or whether the user is intoxicated) based on a $T_{skin}$ 373, $T_{env}$ 375, and the values indicative of hemoglobin concentrations at three or more regions on the user's face, which are calculated based on the images 377.

In different embodiments, a reference to "the computer 380" may refer to different components and/or a combination of components. In some embodiments, the computer 380 may include a processor located on a head-mounted device, such as the smartglasses 370. In other embodiments, at least some of the calculations attributed to the computer 380 may be performed on a remote processor, such as the user's smartphone and/or a cloud-based server. Thus, references to calculations being performed by the "computer 380" should be interpreted as calculations being performed utilizing one or more computers, with some of these one or more computers possibly being attached to a head-mounted device to which the first head-mounted temperature sensor 372 is coupled.

Calculating the values indicative of hemoglobin concentrations at three or more regions on the user's face may be done utilizing the various teachings described herein regarding calculating patterns indicative of hemoglobin concentrations at different regions (e.g., calculations described herein as being performed by the computer 340 on at least some of the images 333 in order to calculate a baseline and/or current pattern). In one example, the middles of the three or more regions are at least 3 mm apart from each other. In another example, the middles of the three or more regions are at least 1 cm apart from each other. In yet another example, the middles of the three or more regions are at least 3 cm apart from each other. Optionally, the values indicative of the hemoglobin concentrations at three or more regions on the user's face may include values calculated based on different channels of the images 377. Optionally, the images 377 used to calculate the values are taken during a window in time, such as a window that is at most five second long. Optionally, the window is at most 30 seconds long. Optionally, the window is at most 5 minutes long. Optionally, the window is at most one hour long.

In one embodiment, the computer 380 may optionally calculate the values indicative of hemoglobin concentrations based on detecting facial flushing patterns in the images. Optionally, the camera 376 in this embodiment may be an inward-facing head-mounted camera that captures the images 377 from a distance between 5 mm and 5 cm from the user's head, and the second region is larger than 2 cm².

In another embodiment, the computer 380 may optionally calculate the values indicative of hemoglobin concentrations based on detecting imaging photoplethysmogram signals in the images. Optionally, the camera 376 in this embodiment may also be an inward-facing head-mounted camera that captures the images 377 from a distance between 5 mm and 5 cm from the user's head.

As discussed in more detail above in this disclosure, detection of reflections of light at different wavelengths can be used to account for thermal interference by the environment. To this end, in some embodiments, the computer 380 may calculate separate values indicative of hemoglobin concentrations from the images 377, which correspond to different channels in the images 377. In one embodiment, the images 377 include a first channel corresponding to wavelengths that are mostly below 580 nanometers and a second channel corresponding to wavelengths mostly above 580 nanometers. In this embodiment, the computer 380 calculates the values indicative of hemoglobin concentrations, which include the following: (i) first values derived based on the first channel in the images, and (ii) second values derived based on the second channel in the images. Having separate values for different wavelengths enables to account for interference from the environment when detecting whether the user has the fever because temperature interference from the environment is expected to affect the first values more than the second values. Optionally, the computer 380 also calculates a confidence in a detection of the fever, such that the confidence decreases as the difference between the first values and the second values increases.

Detection of whether the user has a fever and/or is intoxicated may involve utilization of machine learning approaches. In some embodiments, the computer 380 generates feature values based on $T_{skin}$ 373, $T_{env}$ 375, and the values indicative of hemoglobin concentrations at three or more regions on the user's face (which are calculated based on the images 377). These feature values are utilized by the computer 380 in a machine learning-based approach to detect whether the user has a fever and/or whether the user is intoxicated. Optionally, the computer 380 utilizes a model 386 to calculate, based on the feature values, a value indicative of whether the user has a fever and/or a value indicative of whether the user is intoxicated.

As discussed above with reference to similar calculations performed by the computer 340, the value calculated by the computer 380 based on the feature values may be a binary value, or some other value, such as a scalar. Additionally, in some embodiments, the model 386 may be trained utilizing training data collected under different conditions (similar to the different conditions under which the data used training for model 346 were collected). Furthermore, in some embodiments, the model 386 may be personalized for a user by training the model on samples that include: feature values generated based on measurements of the user, and corresponding labels indicative of the extent of fever and/or intoxication of the user while the measurements were taken. In some embodiments, the model 386 may be generated based on measurements of multiple users, in which case, the model 386 may be considered a general model.

There are various types of feature values that may be generated by the computer 380 based on input data, which may be utilized to calculate a value indicative of whether the user has a fever and/or whether the user is intoxicated. Some examples of feature values include "raw" or minimally processed values based on the input data (i.e., the features are the data itself or applying generic preprocessing functions to the data). Other examples of feature values include feature values that are based on higher-level processing, such a feature values determined based on domain-knowledge. In one example, feature values may include values of patterns of hemoglobin concentration at the three or more regions on the user's face, which are generated based on the images 377.

As mentioned in more detail above in the discussion about detecting fever and/or intoxication by the computer 340 based on a deviation of a current pattern from a baseline pattern of hemoglobin concentration, generating a baseline pattern of hemoglobin concentration can be done based on images previously taken by the camera 376 (referred to as "baseline images"). Optionally, the baseline images were taken previously (prior to when the images 377 were taken) while the user was not in a state being detected. Optionally, windows during which the baseline images were taken may have different lengths, and end prior to a current time (when the images 377 were taken). Optionally, windows during which baseline images are taken end before the current time. In one example, the baseline images may have been taken at different times during a window spanning several hours. In another example, the baseline images include images taken at different times during a window spanning several days/weeks/months, such that the baseline images include images taken on different days/weeks/months, respectively. Optionally, the computer 380 may receive indications indicative of times in which the user is in a baseline state (e.g., without a fever or not intoxicated), and at least some of the baseline images are selected based on the indications.

In one embodiment, the baseline images are utilized by the computer 380 to calculate the baseline pattern, which is indicative of baseline hemoglobin concentrations at the three or more regions on the user's face. Optionally, the baseline hemoglobin concentrations at three or more regions on the user's face are values characteristic of times in which the user did not have a fever and/or was sober. Additionally or alternatively, the computer 380 may utilize a detected-state pattern indicating hemoglobin concentrations characteristic of times in which the user is in the detected state (e.g., while the user has a fever and/or is intoxicated). Optionally, the detected-state baseline may be utilized by the computer when detecting whether the user has a fever and/or whether the user is intoxicated.

In one embodiment, the computer 380 calculates, based on additional baseline images captured with the cameras 376 while the user had a fever, a fever-baseline pattern comprising additional values indicative of hemoglobin concentrations at the three or more regions on the user's face. The computer 380 then bases the detection of whether the user has the fever also on a deviation of the values indicative of hemoglobin concentration at the three or more regions on the user's face, which are generated based on the images 377 (i.e., the "current pattern") from the aforementioned additional values (the fever-baseline pattern).

In another embodiment, the computer 380 calculates, based on additional baseline images captured with the cameras 376 while the user was intoxicated, an intoxication-baseline pattern comprising additional values indicative of hemoglobin concentrations at the three or more regions on the user's face. The computer 380 then bases the detection of whether the user is intoxicated also based on a deviation on a deviation of the values indicative of hemoglobin concentration at the three or more regions on the user's face, which are generated based on the images 377 (i.e., the "current pattern") from the aforementioned additional value (the intoxication baseline pattern).

Various types of feature values may be generated based on temperature measurements of a region on the user's face, such as $T_{skin}$ 373, or temperature of the environment, as is the case with $T_{env}$ 375. In one embodiment, the feature values include a temperature value itself (e.g., the value reported in $T_{skin}$ 373). Additionally or alternatively, the feature values may include a difference between the temperature and a previously taken temperature (e.g., a temperature taken 10 minutes prior or one hour prior). Additionally or alternatively, the feature values may include a difference between the temperature and a baseline temperature. In one example, the feature values include a value indicative of the difference between $T_{skin}$ 373, and the average temperature measured at the first region on multiple previous days. In another example, the feature values include a value indicative of the difference between $T_{env}$ 375, and the average temperature measured in the environment on multiple previous days.

The values indicative of hemoglobin concentrations at three or more regions on the user's face may be utilized to generate various types of feature values, in embodiments described herein. In one example, the hemoglobin concentrations at each of the three or more regions are provided as feature values. In another example, a change to the value corresponding to a certain region (e.g., the difference compared to a previous point in time and/or a derivative of the value at the region) is provided as a feature value.

In some embodiments, the values indicative of hemoglobin concentrations at three or more regions on the user's face are treated as a current pattern of hemoglobin concentrations and feature values are generated based on a deviation of the current pattern from one or more reference patterns (e.g., a baseline pattern, a fever-baseline pattern, or an intoxication-baseline pattern). This deviation may be assessed using various methods described above involving calculations by the computer 340 to make a detection based on a deviation of a current pattern from a baseline pattern.

In some embodiments, at least some of the feature values generated by the computer 380 based on the images 377 are feature values described herein as being generated by the computer 340 based on the images 333 (e.g., low-level image features, iPPG signal features, etc.).

In one non-limiting example, feature values generated by the computer 380 include pixel values from the images 377 during a certain window, as well as a value of $T_{skin}$ 373 and a value of $T_{env}$ 375 during the certain window. In another non-limiting example, feature values generated by the computer 380 include timings and intensities corresponding to fiducial points identified in iPPG signals extracted from the images 377 as well as a value of $T_{skin}$ 373 and a value of $T_{env}$ 375. In yet another non-limiting example, feature values generated by the computer 380 include a value of $T_{skin}$ 373, a value of $T_{env}$, and the values indicative of hemoglobin concentrations at three or more regions on the user's face generated based on the images 377.

In some embodiments, one or more of the feature values utilized by the computer 380 to calculate a value indicative of whether the user has a fever and/or is intoxicated may be generated based on additional inputs from sources other than the first head-mounted temperature sensor 372, the second head-mounted temperature sensor 374, and the camera 376. Some examples of such additional inputs include: values indicative of a stress level of the user (e.g., based on measurements of a thermal camera), values indicative of a hydration level of the user (e.g., based on measurements of a thermal camera), values representing the extent of the user's movement (e.g., measurements with IMU 378). Additional details about these inputs are provided above in the discussion of how the computer 340 may utilize these additional inputs to generate feature values.

Training the model 386 may involve utilization of various training algorithms known in the art (e.g., algorithms for training neural networks, and/or other approaches described herein). After the model 386 is trained, feature values may be generated for certain measurements of the user (e.g., $T_{skin}$ 373, $T_{env}$ 375, and images 377), for which the value of the corresponding label (e.g., whether the user has a fever and/or whether the user is intoxicated) is unknown. The computer 380 can utilize the model 386 to calculate a value indicative of whether the user has a fever and/or whether the user is intoxicated based on these feature values.

In some embodiments, the model 386 may be generated based on data that includes measurements of the user. Additionally or alternatively, in some embodiments, the model 386 may be generated based on data that includes measurements of one or more other users (such as users of different ages, weights, sexes, body masses, and health states) Similar to the case with the model 346, in order to achieve a robust model that is useful for detecting fever and/or intoxication in various conditions, in some embodiments, the samples used to train the model 386 may also include samples based on measurements taken in different conditions.

In one embodiment, in which the computer 380 detects whether the user is intoxicated, the model 386 was trained based on previous data sets that include: (i) previously measured $T_{skin}$ and $T_{env}$, and previous values indicative of hemoglobin concentrations captured by the camera 376 while the user was sober, and (ii) additional previously measured $T_{skin}$ and $T_{env}$, and additional previous values indicative of hemoglobin concentrations captured by the camera 376 while the user was intoxicated.

Utilizing the model 386 to detect whether the user has a fever and/or whether the user is intoxicated may involve computer 380 performing various operations, depending on the type of model. Examples of the types of calculations that may be performed by the computer 380 when performing such detections are given in the discussion above about some of the examples of various possibilities for the model 346 and the type of calculations that may be accordingly performed by the computer 340.

Figure 1E:
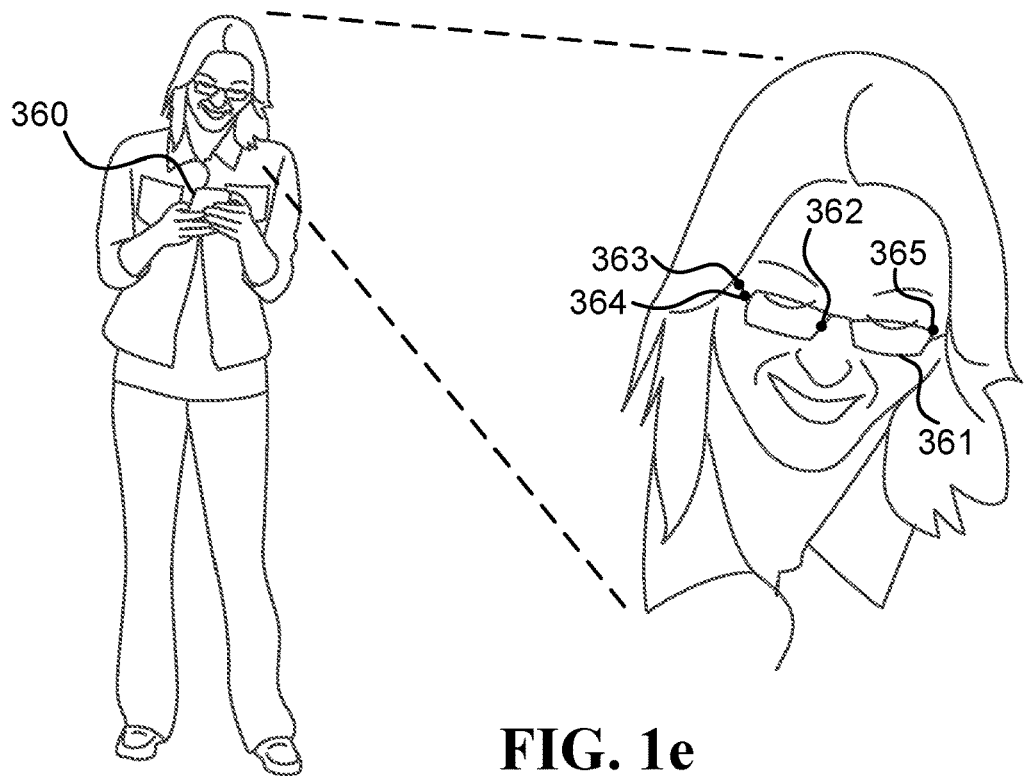
FIG. 1e illustrates one example of a system to detect fever and/or intoxication.

FIG. 1e illustrates one example of a system configured to detect fever and/or intoxication, comprising: (i) a smartphone 360 comprising a camera sensitive to wavelengths below 1050 nanometer, which captures the images, and a computer to detect state of the user (such as whether the user has a fever or is intoxicated), (ii) smartglasses frame 361, (iii) a contact head-mounted temperature sensor 362 (such as a thermistor) to measure skin temperature ($T_{skin}$) of a region on the user's nose, (iv) a non-contact head-mounted thermal camera (such as a thermopile) 363 to measure skin temperature of a region on the user's temple, (v) a head-mounted temperature sensor 364 configured to measure temperature of the environment ($T_{env}$), and (vi) an inward-facing head-mounted camera 365 to capture additional or alternative feed of images of a region on the user's face, from which the values indicative of hemoglobin concentrations can be calculated.

The closer the region, measured by the skin temperature sensor ($S_1$), is to a branch of the external carotid artery (such as the temporal artery), the higher the correlation between $T_{skin}$ and the core body temperature. $S_1$ may be a contact temperature sensor 362 (such as a thermistor or a thermocouple), or a non-contact temperature sensor 363 (such as a thermopile or a microbolometer). When $S_1$ is a contact sensor, the frame to which $S_1$ is coupled to is designed to keep $S_1$ in contact with the first region of skin while wearing the frame. When $S_1$ is a non-contact sensor, the frame is designed to keep $S_1$ in an essentially fixed position relative to the first region of skin while wearing the frame. Optionally, the frame may be an eyeglasses frame, a goggles frame, or a frame embedded in or coupled to a helmet. Additionally or alternatively, the frame may be designed specifically for holding $S_1$ to the user's head.

In one example, the skin region measured by $S_1$ is not located above a portion of a branch of the external carotid artery, which means that the correlation between $T_{skin}$ and the user's core body temperature is expected to be lower compared to the case where the first region is located above a portion of a branch of the external carotid artery. The correlation between $T_{skin}$ and the user's core body temperature is expected to get worse as the thermal interference from the environment becomes more severe. Because the thermal interference affects also the hemoglobin concentrations, the computer can improve the accuracy of estimating the user's core body temperature based on detecting these changes in the hemoglobin concentrations.

In one example, the first region covers a portion of skin located above a portion of a branch of the external carotid artery, and the computer improve the accuracy of estimating the user's core body temperature, when being under thermal interference from the environment, based on detecting the changes in the current hemoglobin concentrations relative to baseline hemoglobin concentrations of the user.

In addition to detecting whether the user has a fever and/or whether the user is intoxicated, in some embodiments, the computer 380 may utilize $T_{skin}$ 373, $T_{env}$ 375, and the values indicative of hemoglobin concentrations calculated based on the images 377 to detect additional physiological signals and/or conditions.

In some embodiments, the computer 380 calculates a value indicative of a level of dehydration of the user based on $T_{skin}$ 373, $T_{env}$ 375, the values indicative of hemoglobin concentrations, and additional measurements of the user. Various types of additional measurements of the user may be used. In one embodiment, the computer 380 receives audio recordings of the user recorded using a head-mounted acoustic sensor 383. In another embodiment, the computer 380 receives a head-movement signal (i.e., values indicative of movements of the user's head) measured with a head-mounted movement sensor (e.g., the IMU 378). Optionally, the head-mounted acoustic sensor 383 and/or the head-mounted movement sensor are coupled to a device to which the head-mounted temperature sensors 372 and 374 are coupled, such as the frame of the smartglasses 370.

In one embodiment, the computer 380 utilizes $T_{skin}$ 373, $T_{env}$ 375, the values indicative of hemoglobin concentrations, the audio recordings, and the head-movement signal, to generate certain feature values and utilizes a certain machine learning-based model to calculate, based on the certain feature values, the value indicative of the level of dehydration of the user. Optionally, at least some of the certain feature values are generated in a similar fashion to the generation of feature values discussed above, which are utilized to detect fever and/or intoxication. Optionally, to generate at least some of the certain feature values that are based on the audio recordings, the computer 380 utilizes some of the various techniques known in the art and/or described in this disclosure for extracting features from audio recordings (e.g., feature values used for detection of coughing and/or respiration, which are described herein). In one example, to generate some of the certain feature values based on the audio recordings, the computer 380 extracts features indicative of the user's respiratory rate and vocal changes. Such features can be beneficial because dehydration is associated with an increase in the respiratory rate and a decrease in the speed quotient at low-pitch phonation. Optionally, to generate at least some of the certain feature values based on the head-movement signal, the computer 380 may utilize various approaches known in the art for extracting values indicative of the extent of movement and smoothness of movement. Such features can be beneficial because dehydration may be associated with both changes to extent of movement and reduction in movement smoothness.

The certain machine learning based model utilized to calculate the value indicative of the level of dehydration of the user may be trained on data collected from one or more users. Optionally, this data is converted to training samples, each training sample comprising measurements $T_{skin}$, $T_{env}$, the values indicative of hemoglobin concentrations, audio recordings, and a head-movement signal of a certain user taken during a creation period, and a label indicative of the dehydration level of the certain user during the certain period.

In one embodiment, the computer 380 calculates the user's core body temperature based on $T_{skin}$ 373, $T_{env}$ 375, the values indicative of hemoglobin concentrations, and optional additional measurements of the user obtained with one or more sensors. To this end, the computer 380 generates certain feature values based on $T_{skin}$ 373, $T_{env}$ 375, the values indicative of hemoglobin concentrations, and the optional additional measurements and utilizes a certain machine learning machine learning based model to calculate, based on the certain feature values, the user's core body temperature. Generating at least some of the certain feature values based $T_{skin}$ 373, $T_{env}$ 375, and the values indicative of hemoglobin concentrations may involve one or more of the various procedures mentioned above with respect to generating feature values from such data. Generation of one or more of the certain feature values based on the optional additional measurements is discussed below with respect to different types of optional additional measurements that may be utilized in different embodiments.

The certain machine learning-based model utilized to calculate the core body temperature may be trained on data collected from one or more users. Optionally, the data is converted to training samples, each training sample comprising measurements $T_{skin}$, $T_{env}$, the values indicative of hemoglobin concentrations, and values of the additional measurements of the user taken during a creation period, and a label indicative of the core body temperature of the user during the certain period. Training the machine learning-based model may involve utilizing one or more training algorithms known in the art, such as training procedures for neural networks, linear regression, support vector machines, decision trees, and the like.

The following are examples of embodiments in which different types of sensors may be used in order to measure at least some of the optional additional measurements mentioned above. Optionally, one or more of the different types of sensors described below may be coupled to a device to which the head-mounted temperature sensors 372 and 374 are coupled, such as the frame of the smartglasses 370.

In one embodiment, the computer 380 receives audio recordings of the user taken with the head-mounted acoustic sensor 383. Optionally, the computer 380 generates one or more of the certain feature values, which are used to calculate the core body temperature, based on the audio recordings. Optionally, the computer 380 generates the one or more of the certain feature values utilizing one or more of the computational approaches described herein for analyzing acoustic data in order to obtain parameters related to respiratory activity. In one example, at least one of the one or more of the certain feature values is indicative of the respiration rate of the user.

In another embodiment, the computer 380 receives a signal indicative of movements of the user's head measured using a head-mounted movement sensor, such as the IMU 378. Optionally, to generate at least one or more of the certain feature values based on the signal indicative of movements of the user's head, the computer 380 may utilize various approaches known in the art for extracting values indicative of the extent of movement of the user. In one example, at least one of the one or more of the certain feature values is indicative of the physical activity level of the user.

In still another embodiment, the computer 380 receives a signal indicative of wind speed hitting the user's head (wind signal) and a signal indicative of humidity (humidity signal) and generates one or more of the certain feature values based on the wind signal and/or the humidity signal. Optionally, the wind signal is measured using the head-mounted anemometer 382 and the humidity signal is measured using the head-mounted hygrometer 384.

In yet another embodiment, the computer 380 receives images of an eye of the user, and generates one or more of the certain feature values based on the images of the eye. Optionally, the one or more of the certain feature values is indicative of a level of reflectiveness of the eye, which often increases with the temperature. Optionally, the images of the eye are taken using a head-mounted inward-facing camera.

In some embodiments, the computer 380 may utilize calibration measurements of the user's core body temperature in order to more accurately calculate the user's core body temperature based on $T_{skin}$ 373, $T_{env}$ 375, the values indicative of hemoglobin concentrations, and optionally some of the additional measurements of the user mentioned above. Optionally, the calibration measurements of the user's core body temperature include measurements of the user's core body temperature taken at a certain time with a different device that is not one of the head-mounted temperature sensors 372 and 374 or the camera 376. Additionally, the calibration measurements of the user's core body temperature may have corresponding measurements taken at the certain time with the head-mounted temperature sensors 372 and 374 or the camera 376.

In one embodiment, one or more of the certain feature values described above, which are used to calculate the core body temperature, may reflect values of the calibration measurements and/or a difference between the values of the calibration measurements and values obtained with the head-mounted temperature sensors 372 and 374 and/or the camera 376 at the time the calibration measurements were taken.

In another embodiment, the computer 380 may utilize a model, which may be a formula, for calculating the core body temperature based on $T_{skin}$ 373, $T_{env}$ 375, the values indicative of hemoglobin concentrations. Optionally, the computer 380 may utilize the calibration measurements to calibrate parameters of the model. In one example, the calibration measurements are utilized to set an offset between the calculated core body temperature (based on corresponding measurements taken with the head-mounted temperature sensors 372 and 374 or the camera 376) and the measurements taken with the different device. Thus, the offset may be applied to make calculated values of core body temperature more accurate. In another example, three or more calibration measurements are used to perform linear regression that is used to obtain a regression formula that is used by the computer 380 to calculate the core body temperature.

In one embodiment, the computer 380 calculates, based on the images 377, a heart rate and/or a respiration rate of the user. For example, the computer 380 may utilize one or more techniques described herein or known in the art for calculating heart rate and/or respiration from iPPG signals (extracted from the images 377). The computer 380 can then utilize the heart rate and/or the respiration rate of the user, to detect whether the user has a fever, and other conditions such as hyperthermia or hypothermia, based on deviations of the current heart rate and/or the current respiration rate from a baseline heart rate and/or baseline respiration rate of the user, respectively. In one example, the computer 380 may utilize a machine learning approach similar to the one described above (for detecting fever and/or intoxication), but instead of using the model 386, the computer 380 uses a different model trained with labels corresponding to extents of hyperthermia or hypothermia (using feature values similar to the ones described above with respect to the model 386).

The user interface 388 may be utilized to present values calculated by the computer 380, such as indications whether the user has a fever or whether the user is intoxicated. Optionally, the user interface 388 is a component of a device of the user, such as a smartphone's screen or an augmented reality display.

In one embodiment, the computer 380 enables the user to share a fever history of the user, upon receiving a permission from the user. For example, the fever history may include indications of times, durations, and/or extent of fever spells the user had. The user may be able to decide to share his/her fever history with a certain person in order to increase the trust and/or receive help, or not share his/her fever history with the certain person if he/she is not interested in increasing the trust and/or receiving help.

In another embodiment, the computer 380 enables the user to share an intoxication history of the user, upon receiving a permission from the user. For example, the intoxication history may include indications of times and/or durations during which the user was intoxicated. The user may be able to decide to share his/her intoxication history with a certain person in order to increase the trust, or not share his/her intoxication history with the certain person if the certain persons does not share in return his/her intoxication history with the user.

The following method for detecting fever may be used by systems modeled according to FIG. 1d. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps: In Step 1, receiving, from a first head-mounted temperature sensor, measurements of skin temperature ($T_{skin}$) at a first region on a user's head. In Step 2, receiving, from a second head-mounted temperature sensor, measurements of temperature of the environment ($T_{env}$). In Step 3, receiving, from a camera sensitive to wavelengths below 1050 nanometer, images of a second region on the user's face. In Step 4, calculating, based on the images, values indicative of hemoglobin concentrations at three or more regions on the user's face. And in Step 5, detecting whether the user has a fever based on $T_{skin}$, $T_{env}$, and the values indicative of hemoglobin concentrations.

In one embodiment, the first region covers a portion of skin that is not located above a portion of a branch of the external carotid artery, and detecting of whether the user has the fever in Step 5 involves (i) generating feature values based on: $T_{skin}$, $T_{env}$, and the values indicative of hemoglobin concentrations, and (ii) utilizing a machine learning based model to calculate, based on the feature values, a values indicative of whether the user has the fever.

In one embodiment, a system configured to detect alcohol intoxication, comprises: a first head-mounted temperature sensor configured to measure skin temperature ($T_{skin}$) at a first region on a user's head; a second head-mounted temperature sensor configured to measure temperature of the environment ($T_{env}$); and a computer configured to: (i) receive images of a second region on the user's face, captured by a camera sensitive to wavelengths below 1050 nanometer, (ii) calculate, based on the images, values indicative of hemoglobin concentrations at three or more regions on the user's face, and (iii) detect whether the user is intoxicated based on $T_{skin}$, $T_{env}$, and the values.

Optionally, the computer detects whether the user is intoxicated by (i) generating feature values based on: $T_{skin}$, $T_{env}$, and the values indicative of hemoglobin concentrations; and (ii) utilizing a machine learning-based model to calculate, based on the feature values, a values indicative of whether the user is intoxicated. Wherein the machine learning-based model was trained based on previous data sets comprising: (i) $T_{skin}$, $T_{env}$, and previous values indicative of hemoglobin concentrations captured by the camera while the user was sober, and (ii) $T_{skin}$, $T_{env}$, and previous values indicative of hemoglobin concentrations captured by the camera while the user was intoxicated.

Optionally, the second region is larger than 2 cm², the camera is an inward-facing head-mounted camera configured to capture the images from a distance between 5 mm and 5 cm from the user's head, and the computer calculates the values indicative of hemoglobin concentrations based on detecting facial flushing patterns in the images.

Optionally, the camera is an inward-facing head-mounted camera configured to capture the images from a distance between 5 mm and 5 cm from the user's head, and the computer calculates the values indicative of hemoglobin concentrations based on detecting imaging photoplethysmogram signals in the images.

The following are additional embodiments of system configured to detect fever and/or calculate core body temperature.

In one embodiment, a system configured to detect fever includes at least a first head-mounted temperature sensor configured to measure skin temperature ($T_{skin}$) at a first region on a user's head, a second head-mounted temperature sensor configured to measure temperature of the environment ($T_{env}$), and a computer. The computer is configured to perform the following: receive images of a second region larger than 2 cm² on the user's face, captured by a camera sensitive to wavelengths below 1050 nanometer; calculate, based on the images, values indicative of hemoglobin concentrations at three or more regions on the face; generate feature values based on: $T_{skin}$, $T_{env}$, and the values indicative of hemoglobin concentrations; and utilize a machine learning based model to detect whether the user has a fever based on the feature values.

In another embodiment, a system configured to detect fever includes at least a first head-mounted temperature sensor configured to measure skin temperature ($T_{skin}$) at a first region on a user's head, a second head-mounted temperature sensor configured to measure temperature of the environment ($T_{env}$), and a computer. The first and second inward-facing head-mounted cameras (Gamma), which located less than 5 cm from the face, sensitive to wavelengths below 1050 nanometer, are configured to capture images of respective first and second regions on the face. Optionally, the middles of the first and second regions are at least 4 cm apart. The computer is configured to perform the following: generate feature values based on: $T_{skin}$, $T_{env}$, and values indicative of hemoglobin concentrations at the first and second regions which are recognizable in the images; and utilize a machine learning-based model to detect whether the user has a fever based on the feature values.

In yet another embodiment, a system configured to detect fever includes at least a first head-mounted temperature sensor configured to measure skin temperature ($T_{skin}$) at a first region on a user's head, a second head-mounted temperature sensor configured to measure temperature of the environment ($T_{env}$), and a computer. The computer is configured to generate baseline values based on: (i) $T_{skin}$ and $T_{env}$, measured during a certain period during which the user's core body temperature was in a normal range, and (ii) images of a second region larger than 1 cm$^2$ on the user's face, captured by a camera sensitive to wavelengths below 1050 nanometer during the certain period, which are indicative of a baseline facial flushing pattern comprising at least 3 points recognizable in the images. Additionally, the computer generates current values based on: (i) $T_{skin}$, and $T_{env}$, measured during a later period, and (ii) current images of the second region, taken during the later period, which are indicative of a current facial flushing pattern comprising the at least 3 points recognizable in the current images. Optionally, the measurements used to calculate the current values are taken at least four hours after the certain period. The computer then detects the fever based on a difference between the baseline values and the current values reaching a threshold.

In still another embodiment, a system configured to calculate core body temperature includes at least a first head-mounted temperature sensor configured to measure skin temperature ($T_{skin}$) at a first region on a user's head, a second head-mounted temperature sensor configured to measure temperature of the environment ($T_{env}$), and a computer. The computer is configured to perform the following: receive images of a second region larger than 2 cm$^2$ on the user's face, captured by a camera sensitive to wavelengths below 1050 nanometer; generate feature values based on: $T_{skin}$, $T_{env}$, and hemoglobin concentration pattern comprising at least 3 points indicative of hemoglobin concentrations recognizable in the images; and utilize a machine learning-based model to calculate the core body temperature based on the feature values.

In yet another embodiment, a system configured to detect fever includes at least a first head-mounted temperature sensor configured to measure skin temperature ($T_{skin}$) at a first region on a user's head, a second head-mounted temperature sensor configured to measure temperature of the environment ($T_{env}$), and a computer. The computer is configured to: receive images of a second region larger than 1 cm$^2$ on the user's face, captured by a camera sensitive to wavelengths below 1050 nanometer; generate feature values based on: $T_{skin}$, $T_{env}$, and facial flushing pattern recognizable in the images; and utilize a machine learning-based model to detect the fever based on the feature values.

Some embodiments of systems for calculating an extent of congestive heart failure (CHF) that a user is suffering from, and/or identify exacerbation of CHF, are described below. These systems rely on measuring signs of CHF that include changes to facial blood flow, respiration, and/or level of activity. Embodiments of these systems include: smartglasses with various sensors and/or cameras coupled thereto, and a computer that is used to calculate the extent of CHF and/or to detect the exacerbation of CHF.

FIG. 2a is a schematic illustration of components of a system configured to calculate an extent of CHF and/or identify exacerbation of CHF. In one embodiment, the system includes at least a pair of smartglasses (e.g., smartglasses 800 or smartglasses 805, illustrated in FIG. 2b and FIG. 2c, respectively), and an inward-facing camera 820, such a camera from among cameras 802a, 802b, and 802c illustrated in FIG. 2b, or a camera from among cameras 806a and 806b illustrated in FIG. 2c. The system also includes computer 828. The system may include additional elements such as a sensor 822, which is configured to measure a signal indicative of respiration, a movement sensor, such as inertial measurement unit (IMU) 830, a skin temperature sensor 824, an environment temperature sensor 826, and/or a user interface 832.

The smartglasses are configured to be worn on a user's head. Optionally, various sensors and/or cameras that are physically coupled to the smartglasses, e.g., by being attached to and/or embedded in the frame of the smartglasses, are used to measure the user while the user wears the smartglasses. Optionally, at least some of the sensors and/or cameras that are physically coupled to the smartglasses may be utilized to measure the environment in which the user is in. In one example, the smartglasses are eyeglasses with sensors and electronics attached thereto and/or embedded therein. In another example, the smartglasses may be an extended reality device (i.e., an augmented realty device, a virtual reality device, and/or mixed reality device).

FIG. 2c illustrates an embodiment of smartglasses that are part of a system for calculating an extent of congestive heart failure (CHF) that a user is suffering from, and/or identify exacerbation of CHF. The system includes smartglasses 805, which have various components coupled thereto. These components include the inward—facing cameras 806a and 806b, which capture images that include portions of the left and right sides of the forehead, respectively. Additionally, the smartglasses 805 may include a microphone 809, which can be used to measure a signal indicative of respiration, a temperature sensor 811 that measures temperature on the user's face, a temperature sensor 812 that measures temperature of the environment, and IMU 814. The smartglasses 805 also include computer 828, which in this embodiment is physically coupled to the frame of the smartglasses 805.

One or more inward-facing cameras, such as the inward-facing camera 820, are physically coupled to the smartglasses. Each of these cameras is configured to capture images of an area comprising skin on the user's head. For example, the inward-facing camera 820 captures images 821 of an area on the user's head. Optionally, the area comprises a portion of the lips of the user. Additional examples of the area are illustrated in FIG. 2b, which describes various possibilities for positioning one or more inward-facing cameras on smartglasses 800. Inward-facing camera 802a is located above the nose bridge and captures images of an area 803a on the user's forehead. Inward-facing cameras 802b and 802c are located on the left and right sides of the smartglasses 800, respectively; they capture images that include areas 803b and 803c on the left and right sides of the user's face, respectively.

Inward-facing cameras, such as the inward-facing camera 820, are optionally mounted more than 5 mm away from the head and/or at least 5 mm away from the area appearing in the images they capture. Optionally, the inward facing camera 820 is mounted less than 10 cm away from the head (i.e., the frame of the smartglasses holds the camera at a distance that is smaller than 10 cm from the head). Optionally, each area appearing in images captured by an inward-facing camera, such as the inward-facing camera 820, is larger than 4 cm^2. In some embodiments, the area on the user's head appearing in images 821 is not occluded by the inward facing camera 820.

Cameras utilized in embodiments described herein (including the inward-facing camera 820) are typically small and lightweight. In some embodiments, each camera weighs below 10 g and even below 2 g. In one example, the inward-facing camera 820 camera is a multi-pixel video camera having a CMOS or a CCD sensor. The video camera may capture images at various rates. In one example, the images 821 are captured at a frame rate of at least 30 frames per second (fps). In another example, the images 821 are captured at a frame rate of at least 100 fps. In still another example, the images 821 are captured at a frame rate of at least 256 fps. Images taken by inward-facing cameras may have various resolutions. In one example, the images 821 have a resolution of at least 8×8 pixels. In another example, the images 821 have a resolution of at least 32×32 pixels. In yet another example, the images 821 have a resolution of at least 640×480 pixels.

In some embodiments, at least one of the inward-facing cameras may capture light in the near infrared spectrum (NIR). Optionally, each of the at least one of the inward-facing cameras may include optics and sensors that capture light rays in at least one of the following NIR spectrum intervals: 700-800 nm, 700-900 nm, 700-1,000 nm. Optionally, the sensors may be CCD sensors designed to be sensitive in the NIR spectrum and/or CMOS sensors designed to be sensitive in the NIR spectrum.

In some embodiments, the system may include an optical emitter configured to direct electromagnetic radiation at an area on the user's head that appears in images captured by an inward-facing camera. Optionally, the optical emitter comprises one or more of the following: a laser diode (LD), a light-emitting diodes (LED), and an organic light-emitting diode (OT FD).

It is to be noted that when embodiments described in this disclosure utilize optical emitters directed at a region of interest (ROI), such as an area appearing in images captured by an inward-facing camera, the optical emitter may be positioned in various locations relative to the ROI. In some embodiments, the optical emitter may be positioned essentially directly above the ROI, such that electromagnetic radiation is emitted at an angle that is perpendicular (or within 10 degrees from being perpendicular) relative to the ROI. Optionally, an inward-facing camera may be positioned near the optical emitter in order to capture the reflection of electromagnetic radiation from the ROI. In other embodiments, the optical emitter may be positioned such that it is not perpendicular to the ROI. Optionally, the optical emitter does not occlude the ROI. In one example, the optical emitter may be located at the top of a frame of a pair of eyeglasses, and the ROI may include a portion of the forehead. In another example, optical emitter may be located on an arm of a frame of a pair of eyeglasses and the ROI may be located above the arm or below it.

The computer 828 may utilize various preprocessing approaches in order to assist in calculations and/or in extraction of an iPPG signal from the images 821. Optionally, the images 821 may undergo various preprocessing steps prior to being used by the computer 828. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081. Additionally or alternatively, images may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an iPPG signal from the images 821 are discussed in Zaunseder et at (2018), "Cardiovascular assessment by imaging photoplethysmography a review", Biomedical Engineering 63(5), 617-634. An example of preprocessing that may be used in some embodiments is given in U.S. Pat. No. 9,020,185, titled "Systems and methods for non-contact heart rate sensing", which describes how times-series signals obtained from video of a user can be filtered and processed to separate an underlying pulsing signal by, for example, using an ICA algorithm.

Due to the proximity of the one or more inward-facing cameras to the face, in some embodiments, there may be an acute angle between the optical axis of an inward-facing camera and the area captured by images taken by said camera (e.g., when the area is on, and/or includes a portion of, the forehead or a cheek). In order to improve the sharpness of images captured by said camera, camera may be configured to operate in a way that takes advantage of the Scheimpflug principle. In one embodiment, camera includes a sensor and a lens; the sensor plane is tilted by a fixed angle greater than 2° relative to the lens plane according to the Scheimpflug principle in order to capture a sharper image when the smartglasses are worn by the user (where the lens plane refers to a plane that is perpendicular to the optical axis of the lens, which may include one or more lenses). In another embodiment, the camera includes a sensor, a lens, and a motor, the motor tilts the lens relative to the sensor according to the Scheimpflug principle. The tilt improves the sharpness of images when the smartglasses are worn by the user. Additional details regarding the application of the Scheimpflug principle are discussed further below.

Variations in the reflected ambient light may introduce artifacts into images collected with inward-facing cameras that can add noise to these images and make detections and/or calculations based on these images less accurate. In some embodiments, the system includes an outward-facing camera, which is coupled to the smartglasses, and takes images of the environment. Optionally, this outward facing camera is located less than 10 cm from the user's face and weighs below 10 g. Optionally, the outward-facing camera may include optics that provide it with a wide field of view.

Changes in respiration pattern (in particular an increased respiration rate) are often associated with CHF and its exacerbation. In order to incorporate information about respiration into detection of CHF, some embodiments include the sensor 822, which is physically coupled to the smartglasses, and configured to measure a respiration signal 823, which is a signal indicative of the user's respiration rate. Various types of sensors may be utilized for this purpose.

In one embodiment, the sensor 822 may be a microphone from among one or more microphones coupled to the smartglasses. The computer 828 may utilize the microphone to measure audio signal comprising sounds in the user's vicinity, and the respiration signal 823 is derived from the sounds. From this respiration signal, values of respiration parameters may be extracted (such as the respiration rate). Various algorithmic approaches may be utilized to extract parameters related to respiration from an acoustic signal. Some examples of possible approaches are provided in Avalur, D. S. "*Human breath detection using a microphone*", Diss. Faculty of Science and Engineering, 2013. Additional algorithmic approaches that may be utilized, in some embodiments, are described in U.S. Pat. No. 7,850,619, titled "Apparatus and method for breathing pattern determination using a non-contact microphone", and in US patent application No. 2019/0029563, titled "Methods and apparatus for detecting breathing patterns".

In another embodiment, the sensor 822 may be an inward-facing head-mounted thermal camera and the respiration signal 823 may include, and/or be derived from, thermal measurements of a region below the nostrils ($TH_{ROI}$) of a user, where $TH_{ROI}$ are indicative of the exhale stream. Optionally, the computer 828 generates certain feature values based on $TH_{ROI}$, and utilizes a certain model to calculate a respiratory parameter, such as the respiration rate, based on the certain feature values. Optionally, the certain model is trained based on previous $TH_{ROI}$ of the user. Additional details regarding utilization of head-mounted thermal cameras to measure signals indicative of respiratory activity are provided in U.S. Pat. No. 10,130,308, titled "Calculating respiratory parameters from thermal measurements", and U.S. Pat. No. 10,136,856, titled "Wearable respiration measurements system".

The computer 828 is configured, in some embodiments, to calculate the extent of CHF based on facial blood flow patterns recognizable the images 821 taken by the inward-facing camera 820 and optionally additional inward facing cameras. Optionally, the computer 828 may utilize additional information such as a respiration rate recognizable in the respiration signal 823. Examples of computers that may be utilized to perform this calculation are computer 400 or computer 410 illustrated in FIG. 23a and FIG. 23b, respectively.

In different embodiments, the computer 828 may refer to different components and/or a combination of components. In some embodiments, the computer 828 may include a processor located on the smartglasses (as illustrated in FIG. 2c). In other embodiments, at least some of the calculations attributed to the computer 828 may be performed on a remote processor, such as a cloud based server. Thus, references to calculations being performed by the "computer 828" should be interpreted as calculations being performed utilizing one or more computers, with some of these one or more computers possibly being remote of the smartglasses. For example, some of the operations attributed to the computer 828 may be performed, in some embodiment's, by a processor in another device of the user (e.g., a processor on a smartphone) or by a cloud-based server.

The images 821 may provide values of coloration intensities (i.e., intensities detected at one or more light wavelengths) at different portions of the area on the user's head, which correspond to the different pixels in the images. In some embodiments, the computer 828 may utilize various computational techniques described herein to extract a photoplethysmogram signal (iPPG signal) from the images 821. In some embodiments, the computer 828 may extract from the images 821 coloration values that do not exhibit a temporal variation that corresponds to the user's cardiac pulses (e.g., average color values for various pixels during a period spanning a duration of several seconds, or longer).

The coloration intensities may represent a facial blood flow pattern that is recognizable in the images 821. A facial blood flow pattern represents characteristics of blood flow in the area captured in the images 821, while the images 821 were taken. A "facial blood flow pattern" may refer to various types of patterns, in embodiments described herein. The following are some examples of types of patterns that may be recognizable in the images 821.

In some embodiments, a facial blood flow pattern refers to a color mapping of various portions of the area captured in the images 821 (e.g., the mapping provides the colors of different pixels in the images 821). Optionally, the mapping provides average intensities of one or more colors of the pixels over a period of time during which the images 821 were taken. Since the extent of cutaneous blood flow affects the skin coloration, the colors observed in the images 821 can indicate the extent of blood flow in different portions of the area. For example, increased blood flow can be detected as higher pixel intensities for the color red (due to the flushness accompanying the increase blood flow). In another example, CHF may lead to decreased blood flow, which may cause colors in the area to change towards pallor (an extremely pale or grayish coloring of the face) or change due to cyanosis (having a bluish coloring of the nails, lips and possibly the skin). The occurrence of CHF can lead to slight changes in the colors, which may not be detected by the naked eye. However, the head-mounted system can detect these slight (or distinct) color changes, and track their trend that is indicative of the extent of CHF.

In other embodiments, a facial blood flow pattern may refer to time series data, such as a sequence of images representing a progression of a pulse wave in the area. Different extents of blood flow may produce different sequences of representative images, which depend on the structure of the facial blood vessels of the user. For example, for the same user and area, a stronger blood flow can be represented by a sequence of images with larger color variations than the color variation in a sequence of images representing a weaker blood flow in the area.

In still other embodiments, a facial blood flow pattern may refer to a contour map, representing the extent to which pixels at a certain wavelength (e.g., corresponding to the color red) have at least a certain value. Since the extent of blood flow is correlated with an increase in intensity of certain colors (e.g., red), a facial blood flow pattern for a stronger blood flow will have different contour map than the contour map observed in a facial blood flow pattern that corresponds to a weaker blood flow in the same area. The contour map depends on the structure of the facial blood vessels of the user, and a machine learning model used to determine extent of blood flow can be trained on sets of images corresponding to different levels of blood flows captured from different users.

Herein, sentences of the form "a facial blood flow pattern recognizable in the images (of an area comprising skin on the user's head)" refer to effects of blood volume changes due to pulse waves that may be extracted from one or more images of the area. These changes may be identified and/or utilized by a computer, but need not necessarily be recognizable to the naked eye (e.g., because of their subtlety, the short duration in which they occur, or involvement of light outside of the visible spectrum).

Additionally, sentences of the form "a respiration rate recognizable in the respiration signal" refer to values that may be extracted from the respiration signal, when algorithms known in the art are utilized to calculate the respiration rate from the respiration signal.

It is to be noted that stating that a computer performs a calculation based on a certain value that is recognizable in certain data (e.g., the respiration rate recognizable in the respiration signal) does not necessarily imply that the computer explicitly extracts the value from the data. For example, the computer may perform its calculation without explicitly calculating the respiration rate. Rather, data that reflects the respiration rate (the respiration signal) may be provided as input utilized by a machine learning algorithm. Many machine learning algorithms (e.g., neural networks) can utilize such an input without the need to explicitly calculate the value that is "recognizable".

A facial blood flow pattern, such as one of the examples described above, may be calculated, in some embodiments, from the images 821 by the computer 828. Optionally, the facial blood flow pattern may be utilized to generate one or more feature values that are used in a machine learning-based approach by the computer 828 to calculate the extent of CHF and/or identify an exacerbation of CHF, as described below. In other embodiments, the calculated blood flow pattern may be utilized to calculate additional values used to represent the extent of facial blood flow, which may be evaluated, e.g., by comparing the extent of blood flow to thresholds in order to calculate the extent of CHF and/or identify an exacerbation of CHF.

In one embodiment, a facial blood flow pattern may be converted to a value representing the proportion of the area in which the intensities of pixels reach a threshold. In one example, the intensities being evaluated may be average intensities (e.g., average pixel intensities in the images 821). In another example, the intensities being evaluated may be intensities of systolic peaks (determined by detecting the spread of a pulse wave in the area captured in the images 821).

In another embodiment, a facial blood flow pattern may be compared with one or more reference facial blood flow patterns that may correspond to specific blood flow levels and/or specific levels of CHF. Optionally, the reference patterns may be based on previously taken images of the user, which were taken at times for which the extent of CHF and/or blood flow was determined manually, e.g., by a physician. Optionally, the similarity of the facial blood flow pattern to the reference patterns may be utilized to generate one or more feature values utilized in a machine learning approach, as described below.

The computer 828 may produce different types of results, in embodiments described herein, based on input data that includes the images 821 and optionally other data, such as the respiration signal 823, $T_{skin}$ 825, $T_{env}$ 827, measurements of an IMU 830, and/or additional optional data described herein. Optionally, the results, which may include, for example, an indication of extent of CHF and/or an indication of the exacerbation, are reported via the user interface 832. Optionally, the results may be reported to a caregiver (e.g., a physician).

In some embodiments, the computer 828 is configured to calculate the extent of CHF based on: a facial blood flow patterns recognizable in the images 821, and respiration rate recognizable in the respiration signal 823.

In order to calculate the extent of CHF, in one embodiment, the computer 828 may compare a value calculated based on the facial blood flow pattern (e.g., a similarity to a reference facial blood flow patter) to a first threshold, and compare the respiration rate to a second threshold. Responsive to the value reaching the first threshold, and the respiration rate reaching the second threshold, the computer 828 may determine that the user is experiencing CHF to at least a specified extent.

In another embodiment, calculating the extent of CHF involves generating feature values based on data that includes the facial blood flow pattern and the respiration rate. The computer 828 then utilizes a machine learning model to calculate, based on the feature values, a value indicative of the extent of CHF the user is experiencing. Additional details regarding the machine learning-based approach are provided further below.

Calculating the extent of CHF may involve, in some embodiments, utilization of previous measurements for which a corresponding baseline extent of CHF the user experienced is known. Optionally, the baseline extent of CHF is determined by a physician examining the user. Optionally, one or more feature values utilized to calculate the extent of CHF may be indicative of the baseline value and/or indicative of a difference between the value and a baseline value.

In one embodiment, the computer 828 calculates, based on the images 821, a value indicative of an extent to which skin in the area is blue and/or gray. The computer 828 then utilizes a difference between the value and a baseline value for the extent to which skin in the area is blue and/or gray to calculate the extent of CHF. Optionally, the baseline value was determined while the user experienced a certain baseline extent of CHF.

In another embodiment, the computer 828 calculates, based on the images 821, a value indicative of an extent of color changes to skin in the area due to cardiac pulses. The computer 828 then utilizes a difference between the value and a baseline value for the extent of the color changes to calculate the extent of CHF. Optionally, the baseline value for the extent of the color changes was determined while the user experienced a certain baseline extent of CHF.

The computer 828 may identify, in some embodiments, an exacerbation of the CHF by comparing current measurements of the user, with previous measurements of the user. To this end, in one embodiment, the computer 828 receives: (i) previous images of the area, which are indicative of a previous facial blood flow pattern while the user had a certain extent of CHF, and (ii) a previous respiration rate taken while the user had the certain extent of CHF. Optionally, the certain extent of CHF is provided from manual examination of the user, e.g., by a physician who examined the user at the time. Additionally or alternatively, the certain extent of CHF was calculated by the computer 828 based on data that includes the previous images and the previous respiration signal.

In one embodiment, the computer 828 may identify exacerbation of the CHF based on: a difference above a first predetermined threshold between the first facial blood flow pattern and the previous facial blood flow pattern, and an increase above a second predetermined threshold in the respiration rate compared to the previous respiration rate. Optionally, the first and second thresholds are determined based on previously observed differences in facial blood flow patterns and respiration signals of the user when the user experienced an exacerbation of CHF. Additionally or alternatively, the first and second thresholds may be determined based on differences in facial blood flow patterns and respiration signals of observed when other users experienced an exacerbation of CHF.

In one embodiment, the computer 828 may identify exacerbation of the CHF utilizing a machine learning based approach, in which feature values used to detect an exacerbation of CHF include a feature value is indicative a difference between the first facial blood flow pattern and the previous facial blood flow patter, and another feature value is indicative of an extent of increase in the respiration rate compared to the previous respiration rate.

Identifying an exacerbation of CHF may involve, in some embodiments, monitoring the user over a period of multiple days, weeks, and even months or more. Thus, the images 821 and the images and the respiration signal 823 may be measured over a period spanning multiple days. In these embodiments, the computer 828 may identify the exacerbation of the CHF based on a reduction in average facial blood flow recognizable in the images 821 taken during the period and an increase in the average respiration rate recognizable in measurements of the respiration signal 823 measured during the period.

One sign of CHF is a difficulty in performing physical activity. This leads people who have CHF to be less active. Additionally, when they are physically active, such as walking a certain distance, the physical activity takes a greater than usual toll on their body. This is often manifested as a change in cardio-respiratory activity (such as a smaller increase in blood flow), which takes longer to return to baseline levels from before conducting the physical activity. Thus, in some embodiments, the computer 828 may utilize measurements taken before and after physical activity to calculate an extent of CHF and/or detect exacerbation of CHF.

In order to detect a period in which the user conducted in physical activity, and/or what type of physical activity the user conducted, in some embodiments, the computer 828 may utilize measurements of movements of the user. Optionally, the measurements of movements are obtained utilizing a movement sensor, such as the IMU 830, which is physically coupled to the smartglasses, and configured to measure movements of the user. In one example, the computer 828 may detect when a period of physical activity involves walking for at 20 steps, and compare measurements of the user taken before and after the period to determine the extent of CHF and/or identify exacerbation of CHF, as described below.

In one embodiment, the computer 828 receives a first set of images taken while the user was at rest and prior to a period during which the user performed physical activity. The computer 828 also receives a second set of the images taken within ten minutes after the period. The computer 828 calculates the extent of CHF based on differences in facial blood flow patterns recognizable in the first and second sets of the images. For example, the computer 828 may detect the extent of CHF and/or the exacerbation of CHF based on a determination of whether a difference in parameters of the extent of blood flow which are determined based on the first and second sets of images, reaches a threshold. In another example, the computer 828 may generate one or more feature values utilized by a machine learning approach described herein, which are indicative of differences between extents of blood flow which are determined based on the first and second sets of images.

In one embodiment, the computer 828 calculates a value indicative of skin color at different times based on the second set of images, and calculates the extent of CHF based on a length of a duration following the period, in which the difference between the skin color and a baseline skin color, calculated based on the first set of images, was above a threshold. Optionally, a feature value indicative of the length of the duration may be utilized to calculate the extent of CHF.

In another embodiment, the computer 828 calculates a value indicative of skin color at different times based on the second set of images, and calculates the extent of CHF based on a rate of return of the user's skin color to a baseline skin color calculated based on the first set of images. Optionally, a feature value indicative of the rate of return may be utilized to calculate the extent of CHF.

Dynamics of the user's heart rate following physical activity may also be used to calculate the extent of CHF. In one embodiment, the computer 828 calculates first and second series of heart rate values from portions of iPPG signals extracted from the first and second sets of images, respectively. The computer 828 may calculate the extent of the CHF also based on the extent to which heart rate values in the second series were above heart rate values in the first series. For example, the computer 828 may generate one or more feature values indicative of these differences, and utilize them in the calculation of the extent of the CHF.

In one embodiment, the computer 828 calculates the user's heart rate at different times based on the second sets of images, and calculates the extent of CHF based on a length of a duration following the period, in which the difference between the user's heart rate and a baseline heart rate, calculated based on the first set of images, was above a threshold. Optionally, a feature value indicative of the length of the duration may be utilized to calculate the extent of CHF.

Characteristics of respiration before and after physical activity may also be indicators of the extent of CHF. In one embodiment, the computer 828 receives respiration signal measured while the user was at rest and prior to a period during which the user performed physical activity. The computer 828 also receives a second respiration signal measured within ten minutes after the period. The computer 828 calculates the extent of CHF based on differences respiration rates recognizable in the first and second respiration signals. For example, the computer 828 may detect the extent of CHF, and/or the exacerbation of CHF, based on a determination of whether a difference in respiration rates determined based on the first and second respiration signals, reaches a threshold. In another example, the computer 828 may generate one or more feature values utilized by a machine learning approach described herein, which are indicative of differences between the aforementioned respiration rates.

In one embodiment, the computer 828 calculate the user's respiration rate at different times based on the second respiration signal, and calculate the extent of CHF based on a length of a duration following the period, in which the difference between the user's respiration rate and a baseline respiration rate, calculated based on the first respiration signal, was above a threshold. Optionally, a feature value indicative of the length of the duration may be utilized to calculate the extent of CHF.

The computer 828 may utilize machine learning approaches, in some embodiments, to calculate the extent of CHF and/or identify exacerbation of CHF. In some embodiments, the computer 828 calculates feature values based on data that includes the images 821 (and possibly other data) and utilizes a model to calculate, based on the feature values, a value indicative of the extent of CHF and/or a value indicative of exacerbation of CHF (compared to a previous state of the user). Various examples of feature values that may be generated based on the images 821, the respiration signal 823, and/or measurements of the IMU 830 are provided above in this disclosure.

Generally, machine learning based approaches utilized by embodiments described herein involve training a model on samples, with each sample including: feature values generated based on images taken by the inward-facing camera 820, and optionally respiration signals measured with the sensor 822, and/or other data, which were taken during a certain period, and a label indicative of the extent of CHF (during the certain period). Optionally, a label may be provided manually by the user and/or by a medical professional who examined the user. Optionally, a label may be extracted based on analysis of electronic health records of the user, generated while being monitored at a medical facility.

In some embodiments, the model may be personalized for a user by training the model on samples that include: feature values generated based on measurements of the user, and corresponding labels indicative of the extent of CHF experienced by the user at the time. In some embodiments, the model may be generated based on measurements of multiple users, in which case, the model may be considered a general model Optionally, a model generated based on measurements of multiple users may be personalized for a certain user by being retrained on samples generated based on measurements of the certain user.

There are various types of feature values that may be generated by the computer 828 based on input data, which may be utilized to calculate the extent of CHF and/or identify an exacerbation. Some examples of feature values include "raw" or minimally processed values based on the input data (i.e., the features are the data itself or applying generic preprocessing functions to the data). Other examples of feature values include feature values that are based on higher-level processing, such a feature values determined based on domain-knowledge (e.g., feature values describing properties of pulse waveforms) and/or feature values that are based on high-level image-analysis.

The following are some examples of the various types of feature values that may be generated based on the images 821 by the computer 828. In one embodiment, at least some of the feature values may be derived directly from values of pixels in the images 821. Optionally, at least some of the feature values are values of pixels from the images 821. Optionally, one or more of the feature values may be the values of the pixels themselves or some simple function of the pixels, such as the average of pixels at certain regions in each of the images. Optionally, one or more of the feature values may be various low-level features derived from images, such as features generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may derived from multiple images taken at different times, such as volume local binary patterns (VLBP), cuboids, and/or optical strain-based features. In one example, one or more of the feature values may represent a difference between values of pixels at one time t at a certain location on the face and values of pixels at a different location at some other time t+x (which can help detect different arrival times of a pulse wave).

In some embodiments, at least some feature values utilized by the computer 828 to calculate the extent of CHF and/or identify exacerbation of CHF describe properties of the cardiac waveform in an iPPG signal derived from the images 821. To this end, the computer 828 may employ various approaches known in the art to identify landmarks in a cardiac waveform (e.g., systolic peaks, diastolic peaks), and/or extract various types of known values that may be derived from the cardiac waveform, as described in the following examples.

In one embodiment, at least some of the feature values generated based on the iPPG signal may be indicative of waveform properties that include: systolic-upstroke time, diastolic time, and the time delay between the systolic and diastolic peaks, as described in Samna, Rohan, et al. "Non-invasive cuffless estimation of blood pressure using Photoplethysmography without electrocardiograph measurement." 2014 IEEE REGION 10 SYMPOSIUM. IEEE, 2014.

In another embodiment, at least some of the feature values generated based on the iPPG signal may be derived from another analysis approach to PPG waveforms, as described in US Patent Application US20180206733, entitled "Device, method and system for monitoring and management of changes in hemodynamic parameters", which was published on 26 Jul. 2018. This approach assumes the cardiac waveform has the following structure: a minimum/starting point (A), which increases to a systolic peak (B), which decreases to a dicrotic notch (C), which increases to a dicrotic wave (D), which decreases to the starting point of the next pulse wave (E). Various features that may be calculated by the computer 828, which are suggested in the aforementioned publication, include: value of A, value of B, value of C, value of D, value of E, systol area that is the area under ABLE, diastol area that is the area under CDE, and the ratio between BC and DC.

In still another embodiment, the computer 828 may utilize the various approaches described in Elgendi, M. (2012), "On the analysis of fingertip photoplethysmogram signals", Current cardiology reviews, 8(1), 14-25, in order to generate at least some of the feature values bases on the iPPG signal. This reference surveys several preprocessing approaches for PPG signals as well as a variety of feature values that may be utilized. Some of the techniques described therein, which may be utilized by the computer 828, include calculating feature values based on first and second derivatives of PPG signals.

In some embodiments, at least some of the feature values may represent calibration values of a user, which are values of certain parameters such as waveform properties described above when the user had a known extent of CHF (e.g., as determined based on an evaluation by a physician). Optionally, the computer 828 generates one or more values that are indicative of: (i) a value of the extent of CHF experienced by the user during a certain previous period, and (ii) a value of a property of the pulse waveform (e.g., systolic-upstroke time or diastolic time) during the certain previous period.

One sign of CHF is an increase heart rate. In some embodiments, the computer 828 may utilize one or more feature values indicative of the user's heart rate. Optionally, these feature values may be derived from the images 821, e.g., by performing calculations on iPPG signals extracted from the images 821. In one example, U.S. Pat. No. 8,768, 438, titled "Determining cardiac arrhythmia from a video of a subject being monitored for cardiac function", describes how to obtain a PPG signal from video of a user's face. In this example, a time series signal is generated from video images of a subject's exposed skin, and a reference signal is used to perform a constrained source separation (which is a variant of ICA) on the time series signals to obtain the PPG signal. Peak-to-peak pulse points are detected in the PPG signal, which may be analyzed to determine parameters such as heart rate, heart rate variability, and/or to obtain peak-to-peak pulse dynamics that can be indicative of conditions such as cardiac arrhythmia.

In some embodiments, the computer 828 generates at least some feature values utilized to calculate the extent of CHF, and/or identify exacerbation of CHF, based on the respiration signal 823. In some embodiments, these feature values may be "raw" or minimally processed values. In one example, in which the respiration signal 823 includes thermal measurements, the feature values may be values of the measurements themselves and/or various functions and/or statistics of the thermal measurements such as minimum/maximum measurement values and/or average values during certain windows of time. In another example, in which the respiration signal 823 includes audio, the feature values may include various acoustic features derived from the audio. For example, the audio may be represented as a time series of vectors of acoustic features, where each vector corresponds to a short window of the audio. For example, windows may be between 5 ms and 200 ms long. The signal in a window may be processed in various ways to obtain acoustic features. In one example, fast Fourier transform (FFT) is performed on the audio in each window. From the FFT data for each window, various features may be extracted. For example, some acoustic features may be determined by binning according to filterbank energy coefficients, using a Mel-frequency cepstral component (MFCC) transform, using a perceptual linear prediction (PLP) transform, or using other techniques.

In some embodiments, the computer 828 generates at least some feature values utilized to calculate the extent of CHF and/or identify exacerbation of CHF based on values of respiration parameters calculated based on the respiration signal 823 (e.g., the respiration rate and/or other respiration parameters). Some examples of respiration parameters that may be calculated based on thermal measurements include: breathing rate, respiration volume, whether the user is breathing mainly through the mouth or through the nose, exhale (inhale) duration, post-exhale (post-inhale) breathing pause, a dominant nostril, a shape of the exhale stream, smoothness of the exhale stream, and/or temperature of the exhale stream. Additional details regarding calculation of these parameters is provided in U.S. Pat. No. 10,130,308, titled "Calculating respiratory parameters from thermal measurements".

In one non-limiting example, feature values generated by the computer 828 include pixel values from the images 821 and values obtained by binning according to filterbank energy coefficients, using MFCC transform on results of FFT of the respiration signal 823, which includes audio.

In another non-limiting example, feature values generated by the computer 828 include timings and intensities corresponding to fiducial points identified in iPPG signals extracted from the images 821, and values of respiration parameters calculated based on the respiration signal 823.

In some embodiments, one or more of the feature values utilized by the computer 828 to calculate the extent of CHF and/or identify exacerbation of CHF may be generated based on additional inputs from sources other than the inward-facing camera 820 or the sensor 822.

Stress is a factor that can influence the diameter of the arteries, and thus influence the blood flow. In one embodiment, the computer 828 is further configured to: receive a value indicative of a stress level of the user, and generate at least one of the feature values based on the received value. Optionally, the value indicative of the stress level is obtained using a thermal camera. In one example, the system may include an inward-facing head-mounted thermal camera configured to take measurements of a periorbital region of the user, where the measurements of a periorbital region of the user are indicative of the stress level of the user. In another example, the system includes an inward facing head-mounted thermal camera configured to take measurements of a region on the forehead of the user, where the measurements of the region on the forehead of the user are indicative of the stress level of the user. In still another example, the system includes an inward-facing head-mounted thermal camera configured to take measurements of a region on the nose of the user, where the measurements of the region on the nose of the user are indicative of the stress level of the user.

Hydration is a factor that affects blood viscosity, which can affect the speed at which blood flows in the body, and consequently may affect blood flow patterns recognizable in the images 821. In one embodiment, the computer 828 is further configured to: receive a value indicative of a hydration level of the user, and generate at least one of the feature values based on the received value. Optionally, the system includes an additional camera configured to detect intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer 828 as values indicative of the hydration level of the user.

Momentary physical activity can affect the blood flow of the user (e.g., due to the increase in the heart rate that it involves). In order to account for this factor, in some embodiments, the computer 828 may generate one or more feature values representing the extent of the user's movement from measurements of the IMU 830. In addition, the extent of movement of the user may be indicative of the extent of CHF, since users with advanced CHF tend to be less physically active because physical activity becomes more difficult due to their condition. Thus, the extent of physical activity (e.g., how many steps a user walked in a day), which may also be derived from measurements of the IMU 830, may be utilized to generate one or more feature values, in some embodiments.

The user's skin temperature may affect blood viscosity, thus it may influence facial blood flow patterns that are recognizable in images taken by the inward-facing camera 820. Some embodiments may include the skin temperature sensor 824, which may be a head-mounted sensor physically coupled to the smartglasses. The skin temperature sensor 824 measures temperature of a region comprising skin on the user's head (T skin 825). In one embodiments, the computer 828 is configured to utilize $T_{skin}$ 825 to compensate for effects of skin temperature on the facial blood flow pattern. For example, the computer 828 may generate one or more feature values based on $T_{skin}$ 825, such as feature values indicating average skin temperature or a difference from baseline skin temperature, and utilize these one or more feature values to calculate the extent of CHF and/or identify exacerbation of CHF.

The temperature in the environment may also be a factor that is considered in some embodiments. The temperature in the environment can both impact the user's skin temperature and cause a physiologic response involved in regulating the user's body temperature on the facial blood flow pattern. Some embodiments may include the environment temperature sensor 826, which may optionally, be head-mounted (e.g., physically coupled to the smartglasses). The environment temperature sensor 826 measures an environmental temperature ($T_{env}$ 827). In one embodiment, the computer 828 is configured to utilize $T_{env}$ 827 to compensate for effects of physiologic changes related to regulating the user's body temperature on the facial blood flow pattern. For example, the computer 828 may generate one or more feature values based on $T_{env}$ 827, such as feature values indicating average environment temperature, maximal environment temperature, or a difference from baseline environment temperature, and utilize these one or more feature values to calculate the extent of CHF and/or identify exacerbation of CHF.

Training the model utilized to calculate the extent of CHF and/or identify an exacerbation of CHF may involve utilization of various training algorithms known in the art (e.g., algorithms for training neural networks, and/or other approaches described herein). After the model is trained, feature values may be generated for certain measurements of the user (e.g., the images 821, respiration signal 823, etc.), for which the value of the corresponding label (e.g., the extent of CHF and/or indicator of whether there is an exacerbation) is unknown. The computer 828 can utilize the model to calculate the extent of CHF, and/or whether there is an exacerbation of CHF, based on these feature values.

In some embodiments, the model may be generated based on data that includes measurements of the user (i.e., data that includes images taken by the inward-facing camera 820, the sensor 822, and/or other sensors mentioned herein). Additionally or alternatively, in some embodiments, the model may be generated based on data that includes measurements of one or more other users (such as users of different ages, weights, sexes, body masses, and health states). In order to achieve a robust model, which may be useful for calculating the extent of CHF in various conditions, in some embodiments, the samples used to train the model may include samples based on measurements taken in different conditions. Optionally, the samples are generated based on measurements taken on different days, while in different locations, and/or while different environmental conditions persisted. In a first example, the model is trained on samples generated from a first set of measurements taken while the user was indoors and not in direct sunlight, and is also trained on other samples generated from a second set of measurements taken while the user was outdoors, in direct sunlight. In a second example, the model is trained on samples generated from a first set of measurements taken during daytime, and is also trained on other samples generated from a second set of measurements taken during nighttime. In a third example, the model is trained on samples generated from a first set of measurements taken while the user was moving, and is also trained on other samples generated from a second set of measurements taken while the user was sitting.

Utilizing the model to calculate the extent of CHF and/or identify exacerbation of CHF may involve the computer 828 performing various operations, depending on the type of model. The following are some examples of various possibilities for the model and the type of calculations that may be accordingly performed by the computer 828, in some embodiments, in order to calculate extent of CHF and/or identify exacerbation of CHF: (a) the model comprises parameters of a decision tree. Optionally, the computer 828 simulates a traversal along a path in the decision tree, determining which branches to take based on the feature values. A value indicative of the extent of CHF may be obtained at the leaf node and/or based on calculations involving values on nodes and/or edges along the path; (b) the model comprises parameters of a regression model (e.g., regression coefficients in a linear regression model or a logistic regression model). Optionally, the computer 828 multiplies the feature values (which may be considered a regressor) with the parameters of the regression model in order to obtain the value indicative of the extent of CHF; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer 828 provides the feature values as inputs to the neural network, computes the values of the various activation functions and propagates values between layers, and obtains an output from the network, which is the value indicative of the extent of the CHF and/or an indicator of whether there was an exacerbation of the CHF.

In some embodiments, a machine learning approach that may be applied to calculating extent of CHF and/or identifying exacerbation of CHF based on images may be characterized as "deep learning". In one embodiment, the model may include parameters describing multiple hidden layers of a neural network Optionally, the model may include a convolution neural network (CNN). In one example, the CNN may be utilized to identify certain patterns in the video images, such as the facial blood flow patterns involving blood volume effects and ballistocardiographic effects of the cardiac pulse. Due to the fact that calculations are performed on sequences images display a certain pattern of change over time (i.e., across multiple frames), these calculations may involve retaining state information that is based on previous images in the sequence. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

The following is description of additional aspects of embodiments of systems configured to detect an abnormal medical event, as well as additional embodiments for various systems that may detect physiological responses based on sensor measurements and/or other sources of data.

In some embodiments, a system configured to detect an abnormal medical event includes a computer and several head-mounted devices that are used to measure photoplethysmographic signals (PPG signals) indicative of blood flow at various regions on a user's head. Optionally, the system may include additional components, such as additional sensors that may be used to measure the user and/or the environment. Additionally or alternatively, the system may include a frame configured to be worn on the user's head (e.g., a frame of eyeglasses or smartglasses) and to which at least some of the head-mounted devices and sensors are physically coupled. Having sensors, such as the devices that are used to measure photoplethysmographic signals, physically coupled to the frame may convey certain advantages, such as having the sensors remain at the same positions with respect to the head, even when the user's head makes angular movements. Some examples of abnormal medical events that may be detected by embodiments described herein include an ischemic stroke, a migraine, a headache, cellulitis (soft tissue infection), dermatitis (skin infection), and an ear infection.

In one embodiment, the system includes at least one right-side head-mounted device, configured to measure at least two signals indicative of photoplethysmographic signals ($PPG_{SR1}$ and $PPG_{SR2}$, respectively) at first and second regions of interest ($ROI_{R1}$ and $ROI_{R2}$, respectively) on the right side of a user's head. Optionally, $ROI_{R1}$ and $ROI_{R2}$ are located at least 2 cm apart (where cm denotes centimeters). Optionally, each device, from among the at least one right-side head-mounted device(s), is located to the right of the vertical symmetry axis that divides the user's face.

Additionally, the system includes at least one left-side head-mounted device configured to measure at least two signals indicative of photoplethysmographic signals ($PPG_{SL1}$ and $PPG_{SL2}$, respectively) at first and second regions of interest ($ROI_{L1}$ and $ROI_{L2}$, respectively) on the left side of the user's head. Optionally, each device, from among the at least one right-side head-mounted device(s), is located to the left of the vertical symmetry axis that divides the user's face.

In some embodiments, $ROI_{R1}$ and $ROI_{L1}$ may be symmetrical regions on the right and left sides of the head, respectively (with respect to a symmetry axis that splits the face to right and left sides). Additionally or alternatively, $ROI_{R2}$ and $ROI_{L2}$ may be symmetrical regions on the right and left sides of the head, respectively. In other embodiments, $ROI_{R1}$ and $ROI_{L1}$ may not be symmetrical regions on the right and left side of the head, and/or $ROI_{R2}$ and $ROI_{L2}$ may not be symmetrical regions on the right and left side of the head. Optionally, two regions are considered to be in symmetrical locations if one region is within 1 cm of the symmetrical region on the head.

Various types of devices may be utilized in order to obtain $PPG_{SR1}$, $PPG_{SR2}$, $PPG_{SL1}$, and/or $PPG_{SL2}$. In one embodiment, the at least one right-side head-mounted device includes first and second contact photoplethysmographic devices ($PPG_1$, $PPG_2$, respectively). Additionally or alternatively, the at least one left-side head-mounted device may include third and fourth contact photoplethysmographic devices ($PPG_3$, $PPG_4$, respectively). Herein, a "contact photoplethysmographic device" is a photoplethysmographic device that comes in contact with the user's skin, and typically occludes the area being measured. An example of a contact photoplethysmographic device is the well-known pulse oximeter.

In one example, $PPG_1$, $PPG_2$, $PPG_3$, and $PPG_4$ are physically coupled to an eyeglasses frame, $PPG_1$ and $PPG_3$ are in contact with the nose, and $PPG_2$ and $PPG_4$ are in contact with regions in the vicinities of the ears (e.g., within a distance of less than 5 cm from the center of the concha), respectively.

Figure 3A:
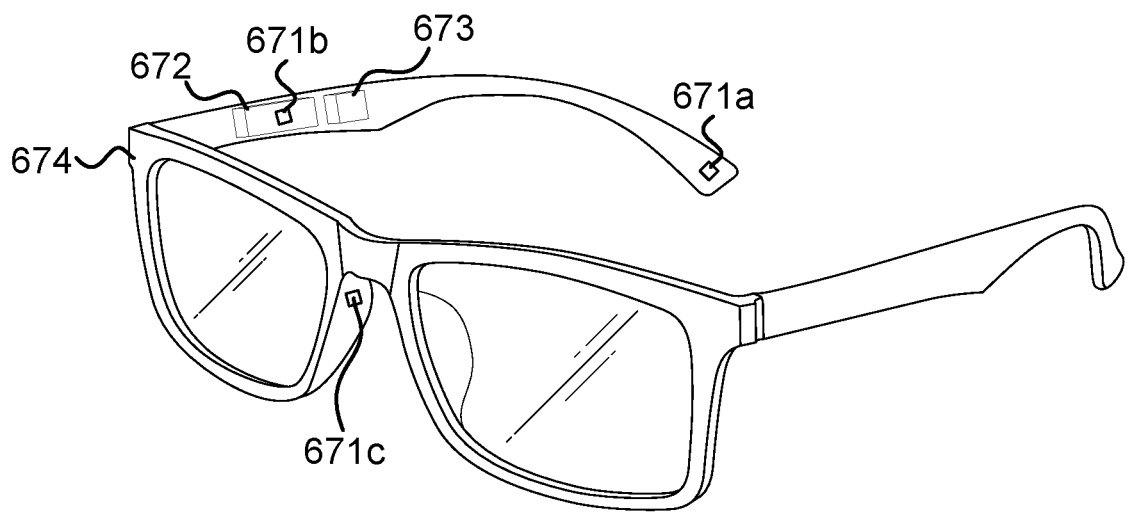
FIG. 3a illustrates smartglasses which include contact photoplethysmographic devices.

FIG. 3a illustrates smartglasses that include contact photoplethysmographic devices that may be used to obtain PPG signals, as described above. The contact PPG devices are coupled to a frame 674. The contact PPG devices may be coupled at various locations on the frame 674 and thus may come in contact with various regions on the user's head. For example, contact PPG device 671a is located on the right temple tip, which brings it to contact with a region behind the user's ear (when the user wears the smartglasses). Contact PPG device 671b is located on the right temple of the frame 674, which puts it in contact with a region on the user's right temple (when wearing the smartglasses). It is to be noted that in some embodiments, in order to bring the contact PPG device close such that it touches the skin, various apparatuses may be utilized, such as spacers (e.g., made from rubber or plastic), and/or adjustable inserts that can help bridge a possible gap between a frame's temple and the user's face. Such an apparatus is spacer 672 which brings contact PPG device 671b in contact with the user's temple when the user wears the smartglasses.

Another possible location for a contact PPG device is the nose bridge, as contact PPG device 671c is illustrated in the figure. It is to be noted the contact PPG device 671c may be embedded in the nose bridge (or one of its components), and/or physically coupled to a part of the nose bridge. The figure also illustrates computer 673, which may be utilized in some embodiments, to perform processing of PPG signals and/or detection of the abnormal medical event, as described further below.

It is to be noted that FIG. 3a illustrates but a few of the possible locations for contact PPG devices on a frame. Any pair of contact PPG devices 671a, 671b, and 671c may be the aforementioned $PPG_1$ and $PPG_2$. Additionally, some embodiments may include additional contact PPG devices on each side of the frames. Furthermore, it is to be noted that while contact PPG devices on the left side were not illustrated in the figure, additional PPG devices may be located in similar locations to the ones of PPG devices 671a to 671c are located, but on the left side of the frame.

In another embodiment, one or more video cameras may be utilized to obtain $PPG_{SR1}$, $PPG_{SR2}$, $PPG_{SL1}$, and/or $PPG_{SL2}$ utilizing imaging photoplethysmography. Using video cameras can be advantageous in some scenarios, such as stroke, where it is unknown in advanced where the physiological response associated with the abnormal medical event will appear on the user's head. Thus, in some embodiments involving these scenarios, using video cameras may provide a great advantage over contact PPG devices, because the video cameras cover larger areas, which increase the chance to capture on time the physiological response associated with the abnormal medical event.

In one embodiment, the at least one right-side head-mounted device includes a first inward facing camera located more than 0.5 cm away from $ROI_{R1}$ and $ROI_{R2}$, and $PPG_{SR1}$ and $PPG_{SR2}$ are recognizable from color changes in regions in images taken by the first camera. Additionally or alternatively, the at least one left-side head-mounted device may include a second inward facing camera located more than 0.5 cm away from $ROI_{L'}$ and $ROI_{L2}$, and $PPG_{SL1}$ and $PPG_{SL2}$ are recognizable from color changes in regions in images taken by the second camera. In one embodiment, the system includes both at least one contact PPG device and at least one video camera.

In one embodiment, each of the first and second inward-facing cameras utilizes a sensor having more than 30 pixels, and each of $ROI_{R1}$ and $ROI_{L1}$ covers a skin area greater than 6 cm^2, which is illuminated by ambient light. In another embodiment, each of the first and second inward-facing cameras utilizes a sensor having more than 20 pixels, and each of $ROI_{R1}$ and $ROI_{L1}$ covers a skin area greater than 2 cm^2, which is illuminated by ambient light. In still another embodiment, each of the first and second inward-facing cameras utilizes a sensor comprising at least 3×3 pixels configured to detect electromagnetic radiation having wavelengths in at least a portion of the range of 200 nm to 1200 nm. Optionally, the system includes first and second active light sources configured to illuminate portions of the right side of the face (which include $ROI_{R1}$ and $ROI_{R2}$) and portions of the left side of the face (which include $ROI_{L1}$ and $ROI_{L2}$), respectively. In one example, the first and second active light sources are head-mounted light sources configured to illuminate their respective portions of the face with electromagnetic radiation having wavelengths in at least a portion of the range of 750 nm to 1200 nm.

In one embodiment, due to the angle between the optical axis of a certain inward-facing camera (from among the first and second inward facing cameras) and its ROI, the Scheimpflug principle may be employed in order to capture sharper images with the certain inward facing camera. For example, when the user wears a frame to which the certain inward facing camera is coupled, the certain inward-facing camera may have a certain tilt greater than 2° between its sensor and lens planes, in order to capture the sharper images.

Figure 3B:
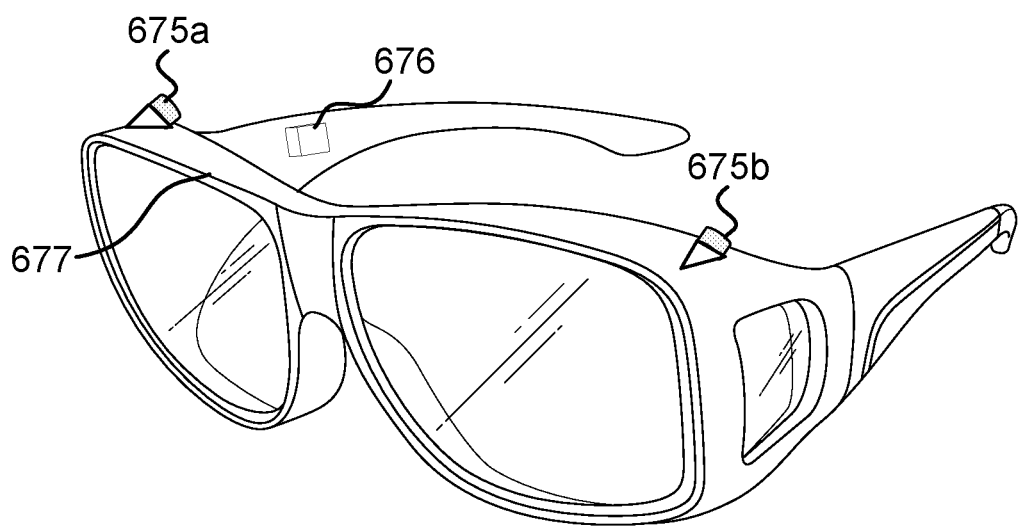
FIG. 3b illustrates smartglasses that include first and second inward-facing cameras.

FIG. 3b illustrates smartglasses that include first and second inward-facing cameras, such as the ones described above. The figure illustrates a frame 677 to which a first inward facing camera 675a is coupled above the lens that is in front of the right eye, and a second inward-facing camera 675b that is coupled to the frame 677 above the lens that is in front of the left eye. The figure also illustrates a computer 676 that is coupled to the frame 677, and may be utilized to process images obtained by the first inward facing camera 675a and/or the second inward facing camera 675b, and/or perform the detection of the abnormal medical event based on PPG signals recognizable in images captured by those cameras.

Various regions on the face may be measured in embodiments that utilize imaging photoplethysmography. In one example, $ROI_{R1}$ and $ROI_{L1}$ are located on the user's right and left cheeks, respectively. In another example, $ROI_{R2}$ and $ROI_{L2}$ are located on the right and left sides of the user's nose, respectively. In yet another example, $ROI_{R1}$ and $ROI_{L1}$ are located on the right and left sides of the user's forehead, respectively. In still another example, $ROI_{R2}$ and $ROI_{L2}$ are located on the user's right and left temples, respectively.

Figure 4:
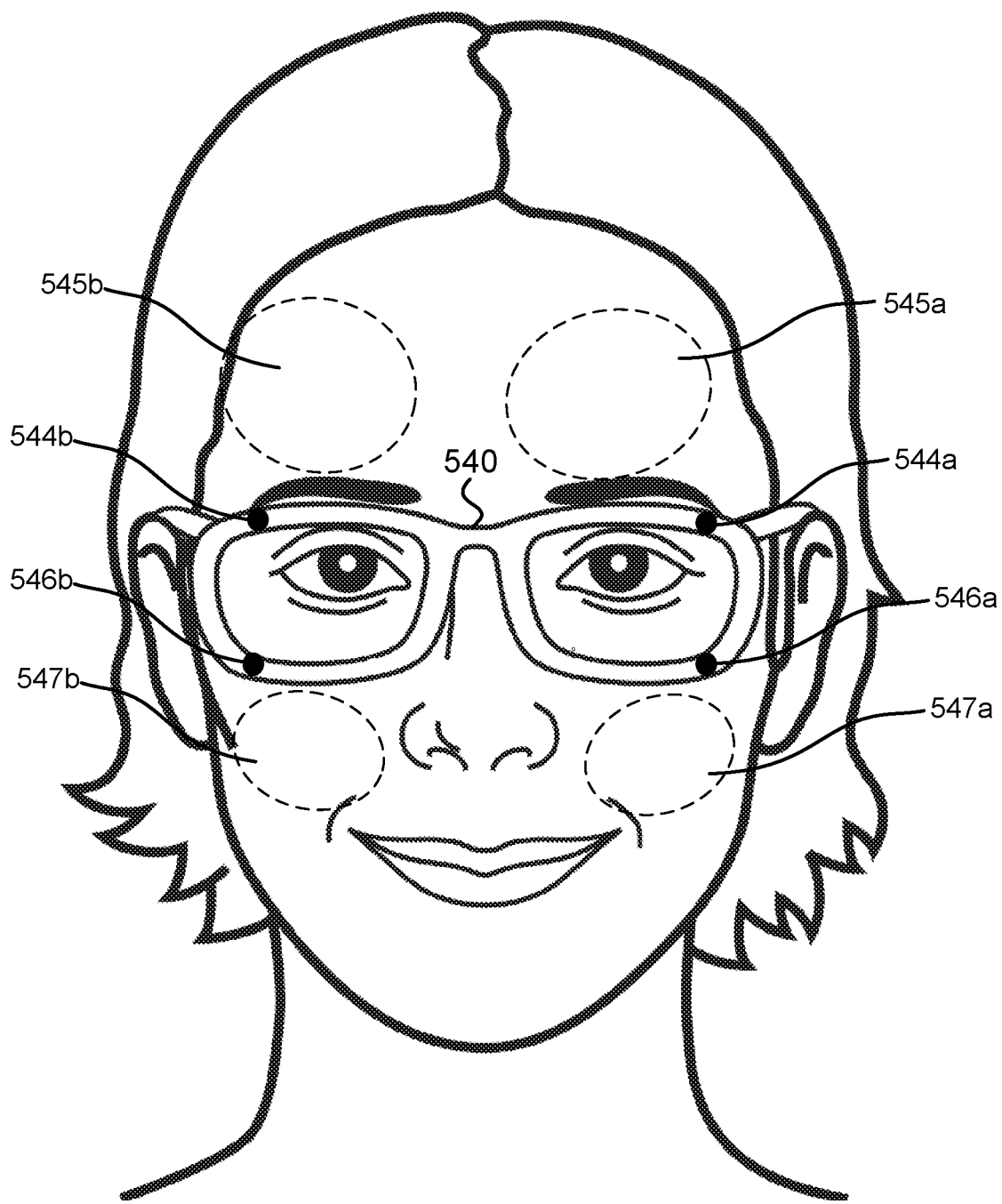
FIG. 4 illustrates smartglasses that include four inward-facing cameras.

A configuration consistent with some of the examples described above is illustrated in FIG. 4. In this figure, four inward-facing cameras are coupled to a frame 540 worn on a user's head: (i) Inward-facing camera 544a is coupled to the top-left side of the frame and captures images of ROI 545a, which is on the left side of the user's forehead; (ii) Inward facing camera 544b is coupled to the top-right side of the frame and captures images of ROI 545b, which is on the right side of the user's forehead; (iii) Inward facing camera 546a is coupled to the bottom-left side of the frame and captures images of ROI 547a, which is on the user's left cheek; And (iv) Inward-facing camera 546b is coupled to the bottom-right side of the frame and captures images of ROI 547b, which is on the user's right cheek.

Herein, sentences of the form "a PPG signal is recognizable from color changes in a region in images" refer to effects of blood volume changes due to pulse waves that may be extracted from a series of images of the region. These changes may be identified and/or utilized by a computer (e.g., in order to generate a signal indicative of the blood volume at the region), but need not necessarily be recognizable to the naked eye (e.g., because of their subtlety, the short duration in which they occur, or involvement of light outside of the visible spectrum). For example, blood flow may cause facial skin color changes (FSCC) that corresponds to different concentrations of oxidized hemoglobin due to varying volume of blood at a certain region due to different stages of a cardiac pulse, and/or the different magnitudes of cardiac output Similar blood flow dependent effects may be viewed with other types of signals (e.g., slight changes in cutaneous temperatures due to the flow of blood).

In some embodiments, the system configured to detect the abnormal medical event may further include first and second outward facing head-mounted cameras for taking images of the environment to the right and to the left of the user's head, respectively. Images taken by these cameras, which are indicative of illumination towards the face, may be utilized to improve the accuracy of detecting the abnormal medical event.

In one example, the first and second outward-facing head-mounted cameras may be thermal cameras that take thermal measurements of the environment. Heat from the environment may affect the surface blood flow, and thus reduce the accuracy of detecting the abnormal medical event. By taking the thermal measurements of the environment into account, the computer is able to detect, and maybe even compensate, for temperature interferences from the environment. Examples of outward-facing head-mounted thermal cameras include thermopile-based and/or microbolometer-based cameras having one or more pixels.

In another example, the first and second outward facing head-mounted cameras may be visible-light cameras (such as CMOS cameras), and/or light intensity sensors (such as photodiodes, photoresistors, and/or phototransistor). Illumination from the environment may affect the surface blood flow (especially when heating the skin), and/or interfere with the photoplethysmographic signals to be measured, and thus reduce the accuracy of detecting the abnormal medical event. By taking the illumination from the environment into account, the computer is able to detect, and maybe even compensate, for the interferences from the environment.

In one embodiment, the at least one right-side head-mounted device and/or the at least one left-side head-mounted device are coupled to a clip-on, and the clip-on comprises a body configured to be attached and detached, multiple times, from a frame configured to be worn on the user's head. Various embodiments described herein include a computer configured to detect the abnormal medical event based on an asymmetrical change to blood flow recognizable in at least $PPG_{SR1}$, $PPG_{SR2}$, $PPG_{SL1}$, and $PPG_{SL2}$. Optionally, the asymmetrical change to the blood flow corresponds to a deviation of $PPG_{SR1}$, $PPG_{SR2}$, $PPG_{SL1}$, and $PPG_{SL2}$ compared to a baseline based on previous measurements of $PPG_{SR1}$, $PPG_{SR2}$, $PPG_{SL1}$, and $PPG_{SL2}$ of the user, taken before the abnormal medical event (e.g., minutes, hours, and even days before the abnormal medical event). In one example, "a baseline based on the previous measurements" is one or more values that are calculated based on the previous measurements (e.g., one or more values representing a normal, baseline blood flow of the user). In another example, "a baseline based on the previous measurements" may be some, or even all, the previous measurements themselves, which may be provided as an input used in calculations involved in the detection of the abnormal medical event (without necessarily calculating an explicit value that is considered a "baseline" value of the user's blood flow).

Figure 23A:
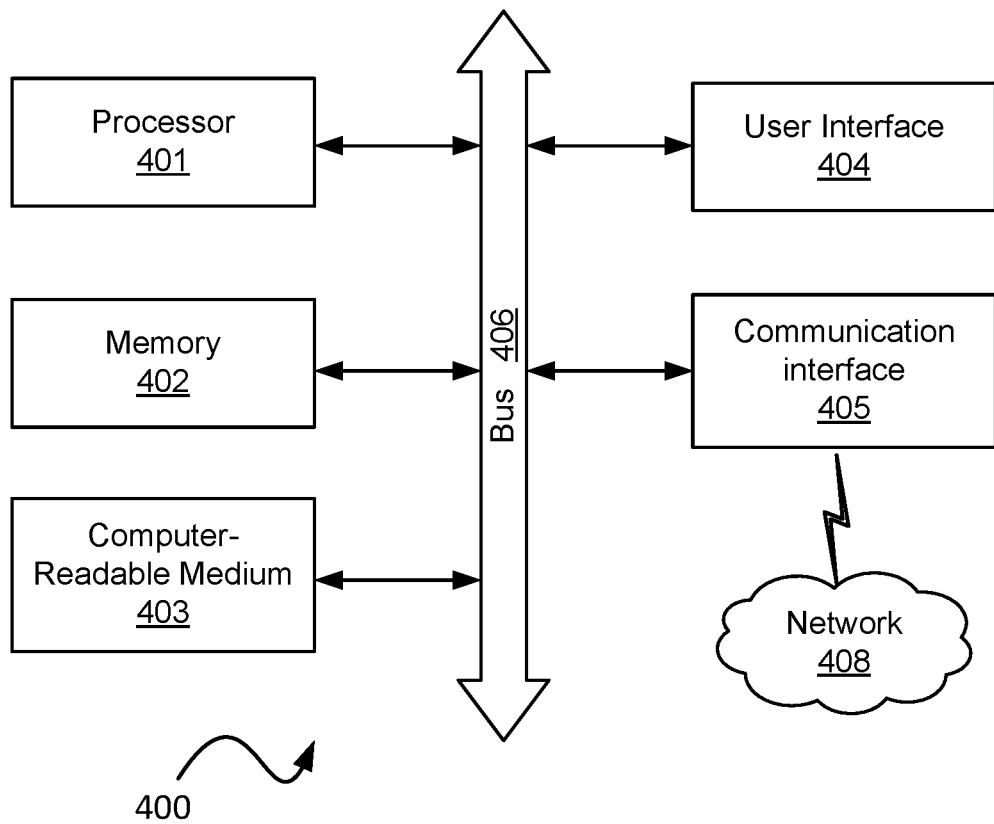
FIG. 23a and FIG. 23b are schematic illustrations of possible embodiments for computers.
Figure 23B:
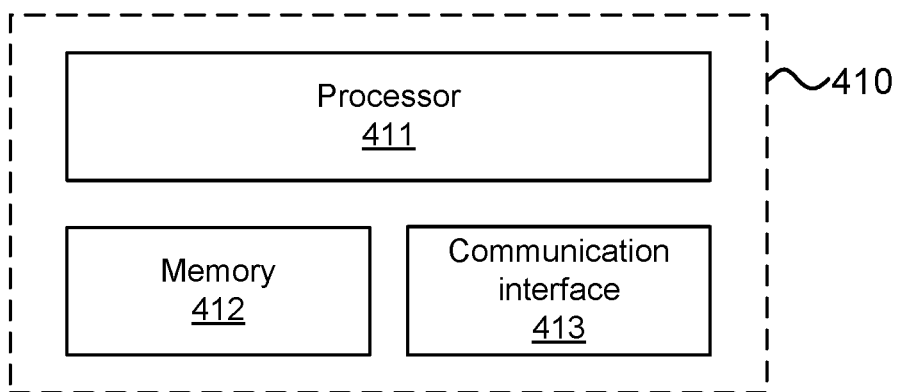

Examples of computers that may be utilized to perform calculations involved in the detection of the abnormal medical event are computers modeled according to computer 400 or computer 410 illustrated in FIG. 23a and FIG. 23b, respectively. Additional examples are the computers 673 and 676 illustrated in FIG. 3a and FIG. 3b, respectively. It is to be noted that the use of the singular term "computer" is intended to imply one or more computers, which jointly perform the functions attributed to "the computer" herein. In particular, in some embodiments, some functions attributed to the computer, such as preprocessing $PPG_{SR1}$, $PPG_{SR2}$, $PPG_{SL1}$, and $PPG_{SL2}$, may be performed by a processor on a wearable device (e.g., smartglasses) and/or a computing device of the user (e.g., smartphone), while other functions, such as the analysis of sensor data and determining whether the user is experiencing the abnormal medical event, may be performed on a remote processor, such as a cloud-based server. In other embodiments, essentially all functions attributed to the computer herein may be performed by a processor on a wearable device (e.g., smartglasses to which the head-mounted devices are coupled) and/or some other device carried by the user, such as a smartwatch or smartphone.

Herein, detecting the abnormal medical event may mean detecting that the user is suffering from the abnormal medical event, and/or that there is an onset of the abnormal medical event. Additionally, an "abnormal" medical event may be a medical event that the user has yet to experience, or does not experience most of the time.

In some embodiments, detecting the abnormal medical event may involve calculating one or more of the following values: an indication of whether or not the user is experiencing the abnormal medical event, a value indicative of an extent to which the user is experiencing the abnormal medical event, a duration since the onset of the abnormal medical event, and a duration until an onset of the abnormal medical event.

When the blood flow on both sides of the head and/or body are monitored, asymmetric changes may be recognized. These changes are typically different from symmetric changes that can be caused by factors such as physical activity (which typically affects the blood flow on both sides in the same way). An asymmetric change to the blood flow can mean that one side has been affected by an event, such as a stroke, which does not influence the other side. In one example, the asymmetric change to blood flow involves a change in blood flow velocity on left side of the head that is at least 10% greater or 10% lower than a change in blood flow velocity on one right side of the head. In another example, the asymmetric change to blood flow involves a change in the volume of blood the flows during a certain period in the left side of the head that is at least 10% greater or 10% lower than the volume of blood that flows during the certain period in the right side of the head. In yet another example, the asymmetric change to blood flow involves a change in the direction of the blood flow on one side of the head (e.g., as a result of a stroke), which is not necessarily observed at the symmetric location on the other side of the head.

Referring to an asymmetrical change to blood flow as being "recognizable in $PPG_{SR1}$, $PPG_{SR2}$, $PPG_{SL1}$, and $PPG_{SL2}$" means that values extracted from $PPG_{SR1}$, $PPG_{SR2}$, $PPG_{SL1}$, and $PPG_{SL2}$ provide an indication that an asymmetric change to the blood flow has occurred. That is, a difference that has emerged in the $PPG_{SR1}$, $PPG_{SR2}$, $PPG_{SL1}$, and $PPG_{SL2}$ may reflect a change in blood flow velocity on one side of the head, a change in blood flow volume, and/or a change in blood flow direction, as described in the examples above. It is to be noted, that the change in blood flow does not need to be directly quantified from the values $PPG_{SR1}$, $PPG_{SR2}$, $PPG_{SL1}$, and $PPG_{SL2}$ in order for it to be "recognizable in $PPG_{SR1}$, $PPG_{SR2}$, $PPG_{SL1}$, and $PPG_{SL2}$". Rather, in some embodiments, feature values generated based on $PPG_{SR1}$, $PPG_{SR2}$, $PPG_{SL1}$, and $PPG_{SL2}$ may be used by a machine learning based predictor to detect a phenomenon, such as the abnormal medical event, which is associated with the asymmetrical change in blood flow.

Having multiple PPG signals, measured at different sides of the head, can assist in detecting an asymmetric change to blood flow in different ways. In one example, an asymmetric change in blood flow may be characterized in an increase in volume at a certain region and/or side of the head, compared to other regions and/or the other side of the head. In this example, the amplitude of the PPG signal at the certain region may show a greater increase compared to increases observed with PPG signals at other regions and/or on the other side of the head. In another example, an asymmetric change in blood flow may be characterized by a decrease in blood velocity at a certain region and/or side of the head, compared to other regions and/or the other side of the head. In this example, a pulse arrival time (PAT) at the certain region may exhibit a larger delay compared to the delay of PATs at other regions and/or at the other side of the head. In still another example, an asymmetric change in blood flow may be characterized by a change in a direction of blood flow at a certain region, compared to other regions and/or the symmetric region on the other side of the head. In this example, an order at which pulse waves arrive at different regions (as evident by PPG signals at the different regions) may be indicative of the direction of blood flow. Thus, a change in the arrival order of pulse waves on one side of the head, which does not occur at regions on the other side of the head, may indicate an asymmetrical change of a direction of blood flow.

In some embodiments, the computer detects the abnormal medical event by utilizing previously taken PPG signals of the user (i.e., previously taken $PPG_{SR1}$, $PPG_{SR2}$, $PPG_{SL1}$, and $PPG_{SL2}$), from a period that precedes the current abnormal medical event being detected at that time. This enables an asymmetrical change to be observed, since it provides a baseline according to which it is possible to compare current $PPG_{SR1}$, $PPG_{SR2}$, $PPG_{SL1}$, and $PPG_{SL2}$, such that it may be determined that a change to blood flow on one side of the head is not the same as a change on the other side of the head. In some embodiments, previously taken $PPG_{SR1}$, $PPG_{SR2}$, $PPG_{SL1}$, and $PPG_{SL2}$ are utilized to calculate a baseline blood flow, such as values representing the extent of blood flow at the different sides of the head, and/or at different regions (e.g., $ROI_{R1}$, $ROI_{R2}$, $ROI_{L1}$ and $ROI_{L2}$). Optionally, calculating the baseline blood flow may be done based on previously taken $PPG_{SR1}$, $PPG_{SR2}$, $PPG_{SL1}$, and $PPG_{SL2}$ that were measured at least an hour before the abnormal medical event is detected. Optionally, the previously taken $PPG_{SR1}$, $PPG_{SR2}$, $PPG_{SL1}$, and $PPG_{SL2}$ include PPG signals measured at least a day before the abnormal medical event is detected. Optionally, the previously taken $PPG_{SR1}$, $PPG_{SR2}$, $PPG_{SL1}$, and $PPG_{SL2}$ include PPG signals measured more than a week before the abnormal medical event is detected.

A baseline for the blood flow may be calculated in various ways. In a first example, the baseline is a function of the average measurements of the user (which include previously taken $PPG_{SR1}$, $PPG_{SR2}$, $PPG_{SL1}$, and $PPG_{SL2}$), which were taken before the occurrence of the abnormal medical event. In a second example, the baseline may be a function of the situation the user is in, such that previous measurements taken during similar situations are weighted higher than previous measurements taken during less similar situations. A PPG signal may show different characteristics in different situations because of the different mental and/or physiological states of the user in the different situations. As a result, a situation-dependent baseline can improve the accuracy of detecting the abnormal medical event. In a third example, the baseline may be a function of an intake of some substance, such that previous measurements taken after consuming similar substances are weighted higher than previous measurements taken after not consuming the similar substances and/or after consuming less similar substances. A PPG signal may show different characteristics after the user consumes different substances because of the different mental and/or physiological states the user may be in after consuming the substances, especially when the substances include things such as medications, drugs, alcohol, and/or certain types of food. As a result, a substance-dependent baseline can improve the accuracy of detecting the abnormal medical event.

There are various types of abnormal medical events that may be detected based on PPG signals that reflect an asymmetrical change to blood flow, which is recognizable in $PPG_{SR1}$, $PPG_{SR2}$, $PPG_{SL1}$, and $PPG_{SL2}$ of the user.

In some embodiments, the abnormal medical event may involve the user having a cerebrovascular accident, which is also known as having a stroke. An occurrence of a stroke often has the following effect on a person. A blood clot (in the case of ischemic stroke) or the ruptured artery (in the case of a hemorrhagic stroke) changes the blood flow to certain regions of the brain. One or more of several mechanisms may be the cause of changes to blood flow that are observed following an onset of a stroke. Blood flow may change due to a stroke because of flaccid muscles (on one side of the face) that use less oxygen and demand less blood. In such an event, local regulation mechanisms may generate signals to the smooth muscles that decrease the diameter of the arteries (which can reduce blood flow). Additionally or alternatively, blood flow may change due to a stroke because of nerve control changes that occur due to reduced blood flow to the brain (a neurogenic mechanism); the same nerves that control the muscles can also be involved in the control of the constriction/dilation of blood vessels. Another possible cause of changes to blood flow involves obstruction-related passive changes. Blood that flows through the major vessels (in the base of the brain it is either the carotid (front) or vertebral (back) arteries, must flow out through one of the branches. When one pathway is blocked or restricted (due to the stroke), more blood has to go through collateral pathways (which may change the blood flow). Thus, changes to the blood flow in the face (and other areas of the head), especially if they are asymmetric, can be early indicators of a stroke. An event of a stroke may be detected in various ways, some which are described in the following examples.

In one embodiment, the abnormal medical event is an ischemic stroke, and the deviation (of $PPG_{SR1}$, $PPG_{SR2}$, $PPG_{SL1}$, and $PPG_{SL2}$ compared to a baseline based on the previous measurements of $PPG_{SR1}$, $PPG_{SR2}$, $PPG_{SL1}$, and $PPG_{SL2}$ of the user) involves an increase in asymmetry between blood flow on the left side of the head and blood flow on the right side of the head, with respect to a baseline asymmetry level between blood flow on the left side of the head and blood flow on the right side of the head (as determined based on the previous measurements). In some embodiments, the term "ischemic stroke" may also include Transient Ischemic Attack (TIA), known as "mini stroke".

In another embodiment, the abnormal medical event is an ischemic stroke, and the deviation (of $PPG_{SR1}$, $PPG_{SR2}$, $PPG_{SL1}$, and $PPG_{SL2}$ compared to a baseline based on the previous measurements of $PPG_{SR1}$, $PPG_{SR2}$, $PPG_{SL1}$, and $PPG_{SL2}$ of the user) involves a monotonic increase in asymmetry between blood flow at $ROI_{R1}$ and $ROI_{R2}$, with respect to a baseline asymmetry of the user (between blood flow at $ROI_{R1}$ and $ROI_{R2}$) during a period longer than 10 minutes. Optionally, $ROI_{R1}$ is located in proximity of the mastoid process behind the right ear, and $ROI_{R2}$ is located before of the right ear.

In yet another embodiment, the abnormal medical event is an ischemic stroke, and the deviation involves an increase in variation between blood flow at $ROI_{R1}$ and $ROI_{R2}$, with respect to a baseline variation of the user between blood flow at $ROI_{R1}$ and $ROI_{R2}$. Optionally, the computer suggests the user to take images of at least one of the retinas, responsive to detecting the increase in variation. The computer may then compare the images of the retinas with previously taken images of the user's retinas, and utilize such a comparison to improve the accuracy of detecting whether the user has suffered the ischemic stroke. Optionally, the comparison of the images of the retinas may take into account parameters such as the diameter of retinal arteries, swelling of the boundaries of the optic disk, and/or blurring of the boundaries of the optic disk. The images of the retinas may be taken by any known and/or to be invented appropriate device.

In some embodiments, the abnormal medical event may involve the user having a migraine or another form of headache. With migraines and other headaches, vasoconstriction of facial or cranial blood vessels may lead to asymmetric changes in blood flow between the left and right sides of the head. Compensatory mechanisms may change smooth muscle constriction around blood vessels, further exacerbating this asymmetry. This vasoconstriction can lead to differential surface blood flow, muscle contraction, and facial temperature changes, leading to asymmetric blood flow. As each individual's particular patterns of vasoconstriction would be unique to the individual, the asymmetric phenomena may be different for different users. Thus, measuring deviation from the user's baseline blood flow patterns may increase the accuracy of detecting these asymmetric phenomena, in some embodiments. Additionally, the time course of migraine or headache usually involves an occurrence over the course of minutes to hours (from the onset of changes to blood flow), and usually occurs with a characteristic pattern, allowing it to be differentiated from signs of other medical, artificial or external causes, which manifest different patterns of blood flow and/or time courses.

In one embodiment, the abnormal medical event is a migraine attack, and the deviation (of $PPG_{SR1}$, $PPG_{SR2}$, $PPG_{SL1}$, and $PPG_{SL2}$ compared to a baseline based on the previous measurements of $PPG_{SR1}$, $PPG_{SR2}$, $PPG_{SL1}$, and $PPG_{SL2}$ of the user) is indicative of a pattern of a certain change to facial blood flow, which is associated with a pattern of a change to facial blood flow of at least one previous migraine attack, determined based on data comprising previous $PPG_{SR1}$, $PPG_{SR2}$, $PPG_{SL1}$, and $PPG_{SL2}$, which were measured starting from at least 5 minutes before the previous migraine attack. In this embodiment, the time of the beginning of the previous migraine attack corresponds to the time at which the user became aware of the migraine attack.

In another embodiment, the abnormal medical event is headache, and the deviation is indicative of at least one of: a change in directionality of facial blood flow, and an asymmetrical reduction in blood flow to one side of the face (for a period lasting more than one minute). For some people, a migraine attack and/or a headache may cause a change in directionality of facial blood flow because the pulse propagation across the face arrives at one side before it arrives to the other side. In one example, the changes in directionality of facial blood flow are calculated from phase variations between $PPG_{SR1}$, $PPG_{SR2}$, $PPG_{SL1}$, and $PPG_{SL2}$ relative to a baseline for the user. For some people, vasoconstriction caused by a migraine attack and/or a headache may affect the amplitude of the PPG signals, such as decreasing of amplitudes of the PPG signals in a certain region. In one example, the reduction in blood flow to one side of the face is calculated from changes between amplitudes of $PPG_{SR1}$, $PPG_{SR2}$, $PPG_{SL1}$, and $PPG_{SL2}$ relative to the baseline.

In some embodiments, the abnormal medical event may involve the user suffering from an infection. Inflammatory conditions, such as cellulitis, dermatitis and ear infection, originate in infection or inflammation in one particular region of the face, causing vasodilation leading to a facial asymmetry originating from phenomena such as increase in swelling, redness and warmth, which are detectable only in the vicinity of the infection. As each individual's baseline facial blood flow and coloration is different, comparing current measurements with the baseline may allow accurate identification of vasodilation resulting from an inflammatory condition. The time course of such inflammatory conditions would usually occur over the course of hours to days, allowing it to be differentiated from other medical or artificial phenomena, which may have similar signs but over a different time course.

Since inflammation often causes temperatures at the infected region to rise, accuracy of detection of some abnormal medical events may increase by measuring the temperature at different regions on the head. In one embodiment, the system configured to detect an abnormal medical event includes right and left head-mounted thermometers, located at least 2 cm to the right and to the left of a vertical symmetry axis that divides the face, respectively. The head-mounted thermometers may be contact thermometers, such as thermistors, and/or non-contact thermal cameras. Optionally, the head-mounted thermometers measure ROIs on one or more of the following regions: the forehead, the temples, behind the ear, the cheeks, the nose, and the mouth. The right and left head-mounted thermometers take right and left temperature measurements, respectively. Optionally, the computer detects the abnormal medical event also based on a deviation of the right and left temperature measurements from a baseline temperature for the user, where the baseline temperature for the user is calculated based on data comprising previous right and left temperature measurements of the user, taken more than a day before the abnormal medical event. Optionally, the abnormal medical event detected in this embodiment is selected from a set comprising cellulitis and dermatitis.

In one embodiments, the system configured to detect an abnormal medical event may optionally include right and left head-mounted thermometers, located less than 4 cm from the right and left earlobes, respectively, which provide right and left temperature measurements, respectively. Optionally, the computer detects the abnormal medical event also based on a deviation of the right and left temperature measurements from a baseline temperature for the user, where the baseline temperature for the user is calculated based on data comprising previous right and left temperature measurements of the user, taken more than a day before the abnormal medical event. In one example, the abnormal medical event is ear infection. In another example, the abnormal medical event is cerebrovascular accident. In still another example, the abnormal medical event is mastoiditis.

Obtaining the PPG signals $PPG_{SR1}$, $PPG_{SR2}$, $PPG_{SL1}$, and $PPG_{SL2}$ from measurements taken by the at least one right-side head-mounted device and the at least one left-side head-mounted device may involve, in some embodiments, performing various preprocessing operations in order to assist in calculations and/or in extraction of the PPG signals. Optionally, the measurements may undergo various preprocessing steps prior to being used by the computer to detect the abnormal medical event, and/or as part of the process of the detection of the abnormal medical event. Some non-limiting examples of the preprocessing include: normalization of pixel intensities (e.g., to obtain a zero-mean unit variance time series signal), and conditioning a time series signal by constructing a square wave, a sine wave, or a user defined shape, such as that obtained from an ECG signal or a PPG signal as described in U.S. Pat. No. 8,617,081.

In some embodiments, in which the at least one right-side head-mounted device and/or at least one left-side head-mounted device are cameras, images taken by the cameras may undergo various preprocessing to improve the signal, such as color space transformation (e.g., transforming RGB images into a monochromatic color or images in a different color space), blind source separation using algorithms such as independent component analysis (ICA) or principal component analysis (PCA), and various filtering techniques, such as detrending, bandpass filtering, and/or continuous wavelet transform (CWT). Various preprocessing techniques known in the art that may assist in extracting an PPG signals from images are discussed in Zaunseder et at (2018), "Cardiovascular assessment by imaging photoplethysmography—a review", Biomedical Engineering 63(5), 617-634. An example of preprocessing that may be used in some embodiments is given in U.S. Pat. No. 9,020,185, titled "Systems and methods for non-contact heart rate sensing", which describes how a times-series signals obtained from video of a user can be filtered and processed to separate an underlying pulsing signal by, for example, using an ICA algorithm.

In some embodiments, detection of the abnormal medical event may involve calculation of pulse arrival times (PATs) at one or more of the regions $ROI_{R1}$, $ROI_{R2}$, $ROI_{L1}$ and $ROI_{L2}$. Optionally, a PAT calculated from an PPG signal represents a time at which the value representing blood volume (in the waveform represented in the PPG) begins to rise (signaling the arrival of the pulse). Alternatively, the PAT may be calculated as a different time, with respect to the pulse waveform, such as the time at which a value representing blood volume reaches a maximum or a certain threshold, or the PAT may be the average of the time the blood volume is above a certain threshold. Another approach that may be utilized to calculate a PAT from an iPPG signal is described in Sola et al. "Parametric estimation of pulse arrival time: a robust approach to pulse wave velocity", Physiological measurement 30.7 (2009): 603, which describe a family of PAT estimators based on the parametric modeling of the anacrotic phase of a pressure pulse.

Detection of the abnormal medical event may involve the computer utilizing an approach that may be characterized as involving machine learning. In some embodiments, such a detection approach may involve the computer generating feature values based on data that includes PPG signals (i.e., $PPG_{SR1}$, $PPG_{SR2}$, $PPG_{SL1}$, and $PPG_{SL2}$ of the user) and optionally other data, and then utilizing a previously trained model to calculate one or more values indicative of whether the user is experiencing the abnormal medical event (which may be any one of the examples of values mentioned further above as being calculated by the computer for this purpose). It is to be noted that when the computer calculates a value that is indicative of the user having the abnormal medical event, at least some of the feature values may reflect the fact that an asymmetrical change to blood flow had occurred. Optionally, the additional data used to generate at least some of the feature values includes previous measurements of $PPG_{SR1}$, $PPG_{SR2}$, $PPG_{SL1}$, and $PPG_{SL2}$ of the user, and/or measurements from additional sensors and/or data sources as discussed below.

Feature values generated based on PPG signals may include various types of values, which may be indicative of dynamics of the blood flow at the respective regions to which the PPG signals correspond. Optionally, these feature values may relate to properties of a pulse waveform, which may be a specific pulse waveform (which corresponds to a certain beat of the heart), or a window of pulse waveforms (e.g., an average property of pulse waveforms in a certain window of time). Some examples of feature values that may be generated based on a pulse waveform include: the area under the pulse waveform, the amplitude of the pulse waveform, a derivative and/or second derivative of the pulse waveform, a pulse waveform shape, pulse waveform energy, and pulse transit time (to the respective ROI). Some additional examples of features may be indicative one or more of the following: a magnitude of a systolic peak, a magnitude of a diastolic peak, duration of the systolic phase, and duration of the diastolic phase. Additional examples of feature values may include properties of the cardiac activity, such as the heart rate and heart rate variability (as determined from the PPG signal). Additionally, some feature values may include values of other physiological signals that may be calculated based on PPG signals, such as blood pressure and cardiac output.

It is to be noted that the aforementioned feature values may be calculated in various ways. In one example, some feature values are calculated for each PPG signal individually. In another example, some feature values are calculated after normalizing a PPG signal with respect to previous measurements from the corresponding PPG device used to measure the PPG signal. In other examples, at least some of the feature values may be calculated based on an aggregation of multiple PPG signals (e.g., different pixels/regions in images captured by an iPPG device), or by aggregating values from multiple contact PPG devices.

In some embodiments, at least some of the feature values may represent comparative values, which provide an indication of the difference in blood flow, and/or in some other property that may be derived from a PPG signal, between various regions on the head. Optionally, such feature values may assist in detecting asymmetrical blood flow (and/or changes thereto). In one example, the feature values include a certain feature value indicative of a difference in maximal amplitudes of one or more of the following pairs of PPG signals: (i) $PPG_{SR1}$ and $PPG_{SR2}$, $PPG_{SR1}$ and $PPG_{SL1}$, and (iii) $PPG_{SR1}$ and $PPG_{SL2}$. In another example, the feature values include a certain feature value indicative of a difference in a pulse arrival time between the following pairs of regions of interest: (i) and $ROI_{R2}$, $ROI_{R1}$ and $ROI_{L1}$, and (iii) $ROI_{R1}$ and $ROI_{L2}$.

In some embodiments, at least some of the feature values describe properties of pulse waveforms (e.g., various types of feature values mentioned above), which are derived from the previous measurements of $PPG_{SR1}$, $PPG_{SR2}$, $PPG_{SL1}$, and $PPG_{SL2}$ of the user. Optionally, these feature values may include various blood flow baselines for the user, which correspond to a certain situation the user was in when the previous measurements were taken.

In some embodiments, at least some of the feature values may be "raw" or minimally processed measurements of the at least one right-side head-mounted device and/or at least one left-side head-mounted device. In one example, at least some of the feature values may be values obtained from contact PPG devices. In another example, at least some of the feature values may be pixel values obtained by inward-facing head-mounted cameras. Optionally, the pixel values may be provided as input to functions in order to generate at feature values that are low-level image-based features. Some examples of low-level features, which may be derived from images, include feature generated using Gabor filters, local binary patterns (LBP) and their derivatives, algorithms such as SIFT and/or SURF (and their derivatives), image keypoints, histograms of oriented gradients (HOG) descriptors, and products of statistical procedures such independent component analysis (ICA), principal component analysis (PCA), or linear discriminant analysis (LDA). Optionally, one or more of the feature values may be derived from multiple images taken at different times, such as volume local binary patterns (VLBP), cuboids, and/or optical strain-based features. In one example, one or more of the feature values may represent a difference between values of pixels at one time t and values of other pixels at a different region at some other time t+x (which, for example, can help detect different arrival times of a pulse wave).

In some embodiments, at least some feature values may be generated based on other data sources (in addition to PPG signals). In some examples, at least some feature values may be generated based on other sensors, such as movement sensors (which may be head-mounted, wrist-worn, or carried by the user some other way), head-mounted thermal cameras (e.g., as mentioned above), or other sensors used to measure the user. In other examples, at least some feature values may be indicative of environmental conditions, such as the temperature, humidity, and/or extent of illumination (e.g., as obtained utilizing an outward-facing head-mounted camera). Additionally, some feature values may be indicative of physical characteristics of the user, such as age, sex, weight, Body Mass Index (BMI), skin tone, and other characteristics and/or situations the user may be in (e.g., level of tiredness, consumptions of various substances, etc.)

Stress is a factor that can influence the diameter of the arteries, and thus influence calculated values that relate to the PPG signals and/or blood flow. In one embodiment, the computer receives a value indicative of a stress level of the user, and generates at least one of the feature values based on the received value. Optionally, the value indicative of the stress level is obtained using a thermal camera. In one example, the system may include an inward-facing head-mounted thermal camera that takes measurements of a periorbital region of the user, where the measurements of a periorbital region of the user are indicative of the stress level of the user. In another example, the system includes an inward facing head-mounted thermal camera that takes measurements of a region on the forehead of the user, where the measurements of the region on the forehead of the user are indicative of the stress level of the user. In still another example, the system includes an inward-facing head-mounted thermal camera that takes measurements of a region on the nose of the user, where the measurements of the region on the nose of the user are indicative of the stress level of the user.

Hydration is a factor that affects blood viscosity, which can affect the speed at which the blood flows in the body. In one embodiment, the computer receives a value indicative of a hydration level of the user, and generates at least one of the feature values based on the received value. Optionally, the system includes an additional camera that detects intensity of radiation that is reflected from a region of exposed skin of the user, where the radiation is in spectral wavelengths chosen to be preferentially absorbed by tissue water. In one example, said wavelengths are chosen from three primary bands of wavelengths of approximately 1100-1350 nm, approximately 1500-1800 nm, and approximately 2000-2300 nm. Optionally, measurements of the additional camera are utilized by the computer as values indicative of the hydration level of the user.

The following are examples of embodiments that utilize additional inputs to generate feature values used to detect the abnormal medical event. In one embodiment, the computer receives a value indicative of a temperature of the user's body, and generates at least one of the feature values based on the received value. In another embodiment, the computer receives a value indicative of a movement of the user's body, and generates at least one of the feature values based on the received value. For example, the computer may receive the input form a head-mounted Inertial Measurement Unit (IMU) that includes a combination of accelerometers, gyroscopes, and optionally magnetometers, and/or an IMU in a mobile device carried by the user. In yet another embodiment, the computer receives a value indicative of an orientation of the user's head, and generates at least one of the feature values based on the received value. For example, the computer may receive the values indicative of the head's orientation from an outward facing head-mounted camera, and/or from a nearby non-wearable video camera. In still another embodiment, the computer receives a value indicative of consumption of a substance by the user, and generates at least one of the feature values based on the received value. Optionally, the substance comprises a vasodilator and/or a vasoconstrictor.

The model utilized to detect the abnormal medical event may be generated, in some embodiments, based on data obtained from one or more users, corresponding to times in which the one or more users were not affected by the abnormal medical event, and additional data obtained while the abnormal medical event occurred and/or following that time. Thus, this training data may reflect PPG signals and/or blood flow both at normal times, and changes to PPG signals and/or blood flow that may ensue due to the abnormal medical event. This data may be used to generate samples, each sample including feature values generated based on PPG signals of a user and optionally additional data (as described above), and a label. The PPG signals include $PPG_{SR1}$, $PPG_{SR2}$, $PPG_{SL1}$, and $PPG_{SL2}$ of the user at a certain time, and optionally previous $PPG_{SR1}$, $PPG_{SR2}$, $PPG_{SL1}$, and $PPG_{SL2}$ of the user, taken before the certain time. The label is a value related to the status of the abnormal medical event. For example, the label may be indicative of whether the user, at the certain time, experienced the abnormal medical event. In another example, the label may be indicative of the extent or severity of the abnormal medical event at the certain time. In yet another example, the label may be indicative of the duration until an onset of the abnormal medical event. In still another example, the label may be indicative of the duration that has elapsed since the onset of the abnormal medical event.

In some embodiments, the model used by the computer to detect the abnormal medical event from measurements of a certain user may be generated, at least in part, based on data that includes previous measurements of the certain user (and as such, may be considered personalized to some extent for the certain user). Additionally or alternatively, in some embodiments, the model may be generated based on data of other users. Optionally, the data used to train the model may include data obtained from a diverse set of users (e.g., users of different ages, weights, sexes, preexisting medical conditions, etc.). Optionally, the data used to train the model which is used to detect the abnormal medical event with a certain user includes data of other users with similar characteristics to the certain user (e.g., similar weight, age, sex, height, and/or preexisting condition).

In order to achieve a robust model, which may be useful for detecting the abnormal medical event for a diverse set of conditions, in some embodiments, the samples used for the training of the model may include samples based on data collected when users were in different conditions. Optionally, the samples are generated based on data collected on different days, while indoors and outdoors, and while different environmental conditions persisted. In one example, the model is trained on samples generated from a first set of training data taken during daytime, and is also trained on other samples generated from a second set of training data taken during nighttime. In a second example, the model is trained on samples generated from a first set of training data taken while users were exercising and moving, and is also trained on other samples generated from a second set of data taken while users were sitting and not exercising.

Utilizing the model to detect the abnormal medical event may involve the computer performing various operations, depending on the type of model. The following are some examples of various possibilities for the model and the type of calculations that may be accordingly performed by the computer, in some embodiments, in order to calculate a value indicative of whether the user was experiencing the abnormal medical event: (a) the model comprises parameters of a decision tree. Optionally, the computer simulates a traversal along a path in the decision tree, determining which branches to take based on the feature values. A value indicative of whether the user was experiencing the abnormal medical event may be obtained at the leaf node and/or based on calculations involving values on nodes and/or edges along the path; (b) the model comprises parameters of a regression model (e.g., regression coefficients in a linear regression model or a logistic regression model). Optionally, the computer multiplies the feature values (which may be considered a regressor) with the parameters of the regression model in order to obtain the value indicative of whether the user was experiencing the abnormal medical event; and/or (c) the model comprises parameters of a neural network. For example, the parameters may include values defining at least the following: (i) an interconnection pattern between different layers of neurons, (ii) weights of the interconnections, and (iii) activation functions that convert each neuron's weighted input to its output activation. Optionally, the computer provides the feature values as inputs to the neural network, computes the values of the various activation functions and propagates values between layers, and obtains an output from the network, which is the value indicative of whether the user was experiencing the abnormal medical event.

In some embodiments, a machine learning approach that may be applied to calculating a value indicative of whether the user is experiencing an abnormal medical event may be characterized as "deep learning". In one embodiment, the model may include parameters describing multiple hidden layers of a neural network Optionally, the model may include a convolution neural network (CNN). In one example, the CNN may be utilized to identify certain patterns in video images, such as the patterns of corresponding to blood volume effects and ballistocardiographic effects of the cardiac pulse. Due to the fact that calculating a value indicative of whether the user is experiencing the abnormal medical event may be based on multiple, possibly successive, images that display a certain pattern of change over time (i.e., across multiple frames), these calculations may involve retaining state information that is based on previous images. Optionally, the model may include parameters that describe an architecture that supports such a capability. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

The following method for detecting an abnormal medical event may be used by systems modeled according to FIG. 3a or FIG. 3b. The steps described below may be performed by running a computer program having instructions for implementing the method. Optionally, the instructions may be stored on a computer-readable medium, which may optionally be a non-transitory computer-readable medium. In response to execution by a system including a processor and memory, the instructions cause the system to perform the following steps:

In Step 1, measuring, utilizing at least one right-side head-mounted device, at least two signals indicative of photoplethysmographic signals ($PPG_{SR1}$ and $PPG_{SR2}$, respectively) at first and second regions of interest ($ROI_{R1}$ and $ROI_{R2}$, respectively) on the right side of a user's head. $ROI_{R1}$ and $ROI_{R2}$ are located at least 2 cm apart.

In Step 2, measuring, utilizing at least one left-side head-mounted device, at least two signals indicative of photoplethysmographic signals ($PPG_{SL1}$ and $PPG_{SL2}$, respectively) at first and second regions of interest ($ROI_{L1}$ and $ROI_{L2}$, respectively) on the left side of the user's head. $ROI_{L1}$ and $ROI_{L2}$ are located at least 2 cm apart.

And in Step 3, detecting the abnormal medical event based on an asymmetrical change to blood flow recognizable in $PPG_{SR1}$, $PPG_{SR2}$, $PPG_{SL1}$, and $PPG_{SL2}$, relative to a baseline based on previous measurements of $PPG_{SR1}$, $PPG_{SR2}$, $PPG_{SL1}$, and $PPG_{SL2}$ of the user, taken before the abnormal medical event.

In some embodiments, detecting the abnormal medical event is done utilizing a machine learning-based approach. Optionally, the method includes the following steps: generating feature values based on data comprising: (i) $PPG_{SR1}$, $PPG_{SR2}$, $PPG_{SL1}$, and $PPG_{SL2}$ of the user, and (ii) the previous measurements of $PPG_{SR1}$, $PPG_{SR2}$, $PPG_{SL1}$, and $PPG_{SL2}$ of the user; and utilizing a model to calculate, based on the feature values, a value indicative of whether the user is experiencing the abnormal medical event.

Various embodiments described herein involve detections of physiological responses based on user measurements. Some examples of physiological responses include stress, an allergic reaction, an asthma attack, a stroke, congestive heart failure, dehydration, intoxication (including drunkenness), a headache (which includes a migraine), and/or fatigue. Other examples of physiological responses include manifestations of fear, startle, sexual arousal, anxiety, joy, pain or guilt. Still other examples of physiological responses include physiological signals such as cardiovascular parameters (such as heart rate, blood pressure, and/or cardiac output), temperature, values of eye-related parameters (such as eye movements and/or pupil diameter), values of speech related parameters (such as frequencies and/or tempo), and/or values of respiratory related parameters (such as respiration rate, tidal volume, and/or exhale duration) of the user. Optionally, detecting a physiological response may involve one or more of the following: determining whether the user has/had the physiological response, identifying an imminent attack associated with the physiological response, and/or calculating the extent of the physiological response.

In some embodiments, detection of the physiological response is done by processing measurements that fall within a certain window of time that characterizes the physiological response. For example, depending on the physiological response, the window may be five seconds long, thirty seconds long, two minutes long, five minutes long, fifteen minutes long, or one hour long. Detecting the physiological response may involve analysis of measurements taken during multiple of the above-described windows, such as measurements taken during different days. In some embodiments, a computer may receive a stream of measurements, taken while the user wears an HMS with coupled cameras and/or other sensors during the day, and periodically evaluate measurements that fall within a sliding window of a certain size.

In some embodiments, models are generated based on measurements taken over long periods. Sentences of the form of "measurements taken during different days" or "measurements taken over more than a week" are not limited to continuous measurements spanning the different days or over the week, respectively. For example, "measurements taken over more than a week" may be taken by eyeglasses equipped with cameras and/or other sensors, which are worn for more than a week, 8 hours a day. In this example, the user is not required to wear the eyeglasses while sleeping in order to take measurements over more than a week. Similarly, sentences of the form of "measurements taken over more than 5 days, at least 2 hours a day" refer to a set comprising at least 10 measurements taken over 5 different days, where at least two measurements are taken each day at times separated by at least two hours.

Utilizing measurements taken over a long period (e.g., measurements taken on "different days") may have an advantage, in some embodiments, of contributing to the generalizability of a trained model. Measurements taken over the long period likely include measurements taken in different environments, and/or measurements taken while the measured user was in various physiological and/or mental states (e.g., before/after meals, and/or while the measured user was sleepy/energetic/happy/depressed, etc.). Training a model on such data can improve the performance of systems that utilize the model in the diverse settings often encountered in real-world use (as opposed to controlled laboratory-like settings). Additionally, taking the measurements over the long period may have the advantage of enabling collection of a large amount of training data that is required for some machine learning approaches (e.g., "deep learning").

Detecting the physiological response may involve performing various types of calculations by a computer. Optionally, detecting the physiological response may involve performing one or more of the following operations: comparing measurements to a threshold (when the threshold is reached that may be indicative of an occurrence of the physiological response), comparing measurements to a reference time series, and/or by performing calculations that involve a model trained using machine learning methods. Optionally, the measurements upon which the one or more operations are performed are taken during a window of time of a certain length, which may optionally depend on the type of physiological response being detected. In one example, the window may be shorter than one or more of the following durations: five seconds, fifteen seconds, one minute, five minutes, thirty minutes, one hour, four hours, one day, or one week In another example, the window may be longer than one or more of the aforementioned durations. Thus, when measurements are taken over a long period, such as measurements taken over a period of more than a week, detection of the physiological response at a certain time may be done based on a subset of the measurements that falls within a certain window near the certain time; the detection at the certain time does not necessarily involve utilizing all values collected throughout the long period.

In some embodiments, detecting the physiological response of a user may involve utilizing baseline measurement values, most of which were taken when the user was not experiencing the physiological response. Optionally, detecting the physiological response may rely on observing a change to typical measurement value at one or more ROIs (the baseline), where different users might have different typical measurement values at the ROIs (i.e., different baselines). Optionally, detecting the physiological response may rely on observing a change to a baseline level, which is determined based on previous measurements taken during the preceding minutes and/or hours.

In some embodiments, detecting a physiological response involves determining the extent of the physiological response, which may be expressed in various ways that are indicative of the extent of the physiological response, such as: (i) a binary value indicative of whether the user experienced, and/or is experiencing, the physiological response, (ii) a numerical value indicative of the magnitude of the physiological response, (iii) a categorial value indicative of the severity/extent of the physiological response, (iv) an expected change in measurements of an ROI, and/or (v) rate of change in measurements of an ROI. Optionally, when the physiological response corresponds to a physiological signal (e.g., a heart rate, a breathing rate, or an extent of frontal lobe brain activity), the extent of the physiological response may be interpreted as the value of the physiological signal.

One approach for detecting a physiological response, which may be utilized in some embodiments, involves comparing measurements of one or more ROIs to a threshold. In these embodiments, the computer may detect the physiological response by comparing the measurements, and/or values derived therefrom (e.g., a statistic of the measurements and/or a function of the measurements), to the threshold to determine whether it is reached. Optionally, the threshold may include a threshold in the time domain, a threshold in the frequency domain, an upper threshold, and/or a lower threshold. When a threshold involves a certain change to a value (such as temperature or heart rate), the certain change may be positive or negative. Different physiological responses described herein may involve different types of thresholds, which may be an upper threshold (where reaching the threshold means≥the threshold) or a lower threshold (where reaching the threshold means≤the threshold).

Another approach for detecting a physiological response, which may be utilized in some embodiments, may be applicable when the measurements of a user are treated as time series data. In some embodiments, the computer may compare measurements (represented as a time series) to one or more reference time series that correspond to periods of time in which the physiological response occurred. Additionally or alternatively, the computer may compare the measurements to other reference time series corresponding to times in which the physiological response did not occur. Optionally, if the similarity between the measurements and a reference time series corresponding to a physiological response reaches a threshold, this is indicative of the fact that the measurements correspond to a period of time during which the user had the physiological response. Optionally, if the similarity between the measurements and a reference time series that does not correspond to a physiological response reaches another threshold, this is indicative of the fact that the measurements correspond to a period of time in which the user did not have the physiological response. Time series analysis may involve various forms of processing involving segmenting data, aligning data, clustering, time warping, and various functions for determining similarity between sequences of time series data. Some of the techniques that may be utilized in various embodiments are described in Ding, Hui, et al "Querying and mining of time series data: experimental comparison of representations and distance measures." Proceedings of the VLDB Endowment 1.2 (2008): 1542-1552, and in Wang, Xiaoyue, et al "Experimental comparison of representation methods and distance measures for time series data." Data Mining and Knowledge Discovery 26.2 (2013): 275-309.

A user interface (UI) may be utilized, in some embodiments, to notify the user and/or some other entity, such as a caregiver, about the physiological response, and/or present an alert responsive to an indication that the extent of the physiological response reaches a threshold. The UI may include a screen to display the notification and/or alert, a speaker to play an audio notification, a tactile UI, and/or a vibrating UI. In some embodiments, "alerting" about a physiological response of a user refers to informing about one or more of the following non-limiting examples: the occurrence of a physiological response that the user does not usually have (e.g., a stroke, intoxication, and/or dehydration), an imminent physiological response (e.g., an allergic reaction, an epilepsy attack, and/or a migraine), and an extent of the physiological response reaching a threshold (e.g., stress and/or blood pressure reaching a predetermined level).

Due to the mostly symmetric nature of the human body, when the face undergoes temperature changes, e.g., due to external factors such as the temperature in the environment or internal factors such as an activity-related rise in body temperature, the changes to the face are generally symmetric. That is, the temperature changes at a region of interest (ROI) on the left side of the face (e.g., the left side of the forehead) are usually similar to the temperature changes at the symmetric ROI on the right side of the face (e.g., the right side of the forehead). However, when the temperature on the face changes in an asymmetric way, this can be indicative of various physiological responses and/or undesirable phenomena. Some examples of phenomena that may be identified by detecting asymmetric thermal patterns ("thermal asymmetry") on a user's face include some types of strokes. In the case of stroke, often the decreased blood flow in certain regions of the head (due to the stroke) can cause a decrease in the cutaneous temperatures near those certain regions.

Some embodiments utilize head-mounted sensors in order to detect stroke signs that involve detectable changes in temperature and/or blood flow due to a stroke event.

In some embodiments, "stroke symptoms" refers to changes to function/sensation reported by the patient. In some embodiments, "stroke signs" refers to objective changes observable by a human individual and/or a sensor. Detecting stroke symptoms and/or stroke signs may also be referred to herein as detecting "whether the user has suffered from a stroke". It is to be noted that a detection that the user has suffered from a stroke may be interpreted, in some cases, as indicating that there is a higher than normal risk that the user has suffered from a stroke, and that certain actions should be taken (such as further investigation of the user's state by other means or seeking medical attention). Thus, in some embodiments, detection by the computer that the user has suffered from a stroke may serve as an initial step that triggers further steps for diagnosing the user's condition and not a definitive final step in diagnosing the user's state.

In some embodiments, a system configured to detect a stroke based on thermal measurements includes at least one inward-facing head-mounted thermal camera (CAM) and computer. The at least one CAM is/are configured to take thermal measurements of at least first and second regions on the right and left sides of the head ($TH_{R1}$ and $TH_{L1}$, respectively) of a user. Optionally, the at least one CAM is located below the first and second regions, and does not occlude the first and second legions. The computer is configured to detect, based on $TH_{R1}$ and $TH_{L1}$, whether the user has suffered a stroke. Optionally, detecting whether the user has suffered from a stroke refers to a recent stroke event, such as an ischemic or hemorrhagic stroke event that started a short while before $TH_{R1}$ and $TH_{L1}$ were taken, where "a short while" may be a period between minutes and several hours before $TH_{R1}$ and $TH_{L1}$ were taken. In this scenario, detection that the user has suffered from a stroke may enable an intervention that can reduce the permanent damage of the stroke. Additionally detecting whether the user has suffered from a stroke may also refer, in some embodiments, to earlier stroke events, which occurred more than six hours before $TH_{R1}$ and $TH_{L1}$ were taken.

The first and second legions of which measurements are taken may include portions of various parts of the head. For example, in different embodiments, the first and second legions may cover a portion of at least one of the following pairs of regions: the right and left sides of the forehead, the right and left temples, the right and left cheeks, the right and left earlobes, behind the right and left ears, periorbital areas around the right and left eyes, the area of the right and left mastoid processes.

In one embodiment, each of the at least one CAM is physically coupled to a frame worn on a user's head, and is located less than 15 cm, 5 cm, or 2 cm from the user's face. In another embodiment, the at least one CAM is physically coupled to a clip-on, and the clip-on comprises a body configured to be attached and detached, multiple times, from a frame configured to be worn on the user's head.

In one embodiment, due to the angle between the optical axis of a certain CAM from among the at least one CAM and the Frankfort horizontal plane, the Scheimpflug principle may be employed in order to capture sharper images with the certain CAM. For example, when the user wears a frame to which the certain CAM is coupled, the certain CAM has a certain tilt greater than 2° between its sensor and lens planes, in order to capture the sharper images. Additional details regarding application of the Scheimpflug are provided herein further below.

Figure 5:
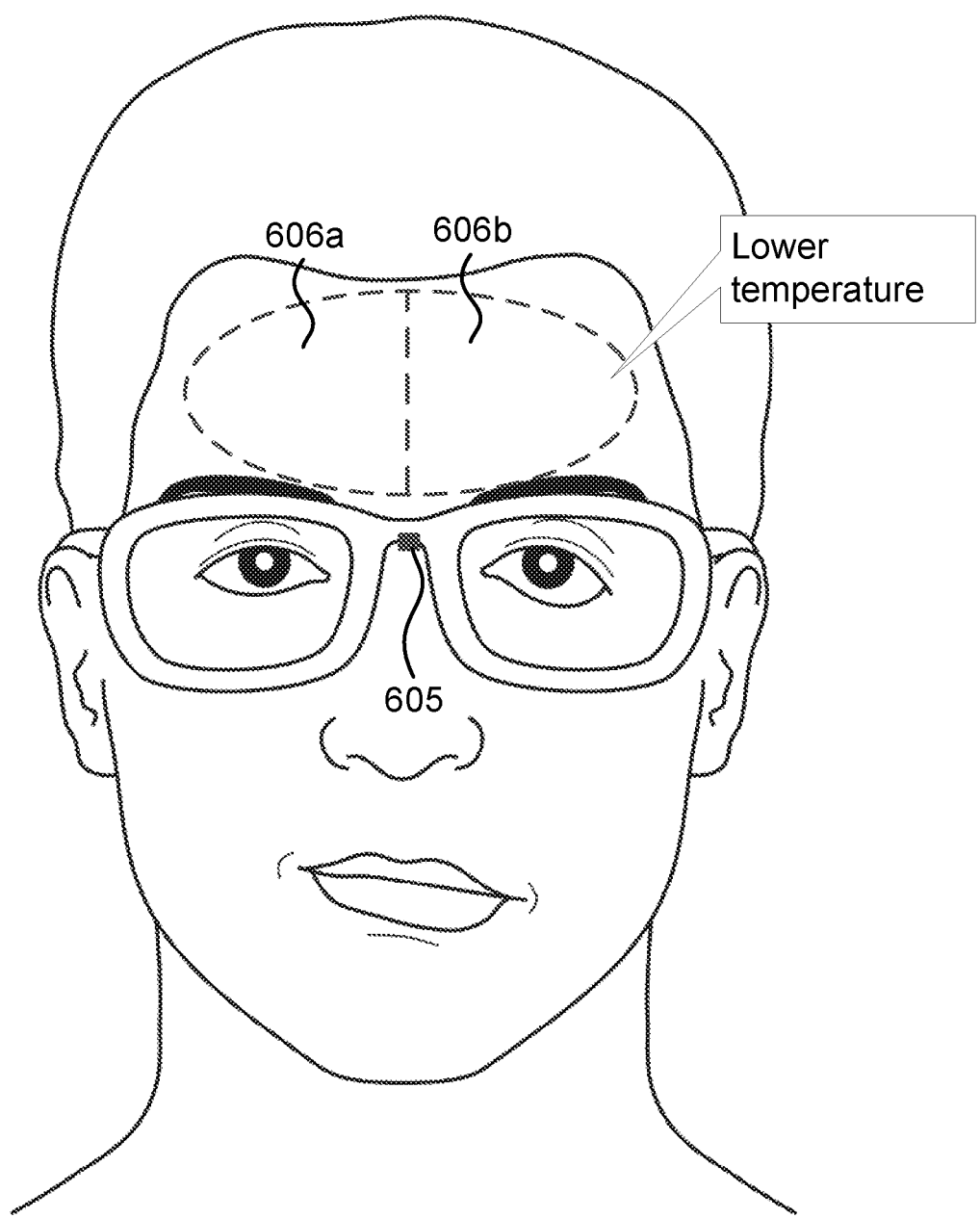
FIG. 5 illustrates an embodiment of a system that includes a single head-mounted thermal camera that may be used to detect a stroke.

The at least one CAM may be a single CAM, in one embodiment, such as a single FPA that captures images that include a portion of both sides of the forehead. In this embodiment, $TH_{R1}$ and $TH_{L1}$ include measurements that cover portions of the left side and right side of user's forehead, respectively. Optionally, $TH_{R1}$ and $TH_{L1}$ may be measured by different subsets of pixels of the FPA. An example of a system that includes a single thermal camera is illustrated in FIG. 5, which illustrates a user wearing glasses with a single thermal sensor 605 that measures ROIs 606a and 606b on the right and left of the forehead, respectively. The user in the figure has already been affected by a stroke, as is evident by the lower temperature detected on the left side of the forehead and the drooping of the left side of the face.

In other embodiments, the at least one CAM may include two or more CAMs. Optionally, the at least one CAM includes two CAMs, denoted CAM1 and CAM2. Optionally, CAM1 and CAM2 are located at least 0.5 cm to the right and to the left of the vertical symmetry axis that divides the face, respectively. Optionally, each of CAM1 and CAM2 weighs below 10 g, 5 g, or 1 g.

Figure 6:
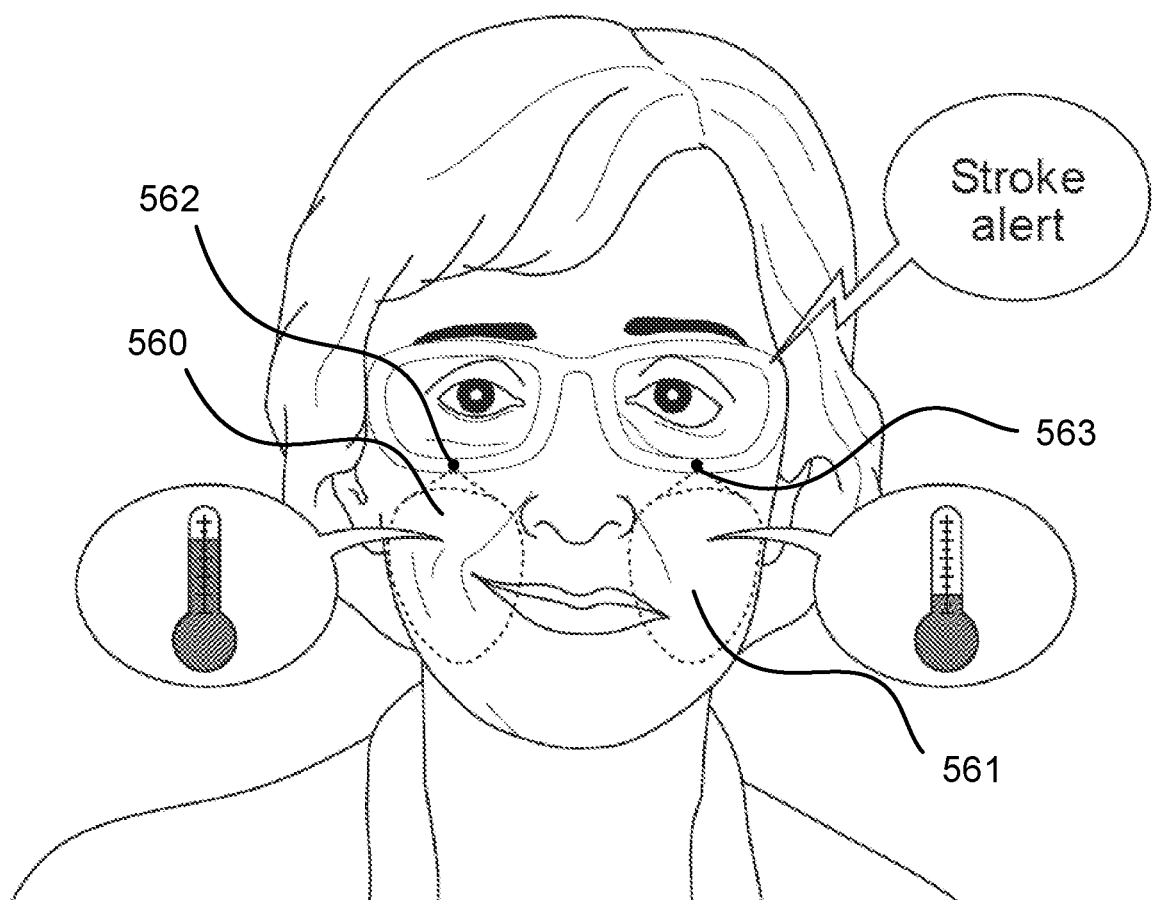
FIG. 6 illustrates a scenario in which an alert regarding a possible stroke is issued.

FIG. 6 illustrates one example of a system for detecting a stroke that includes at least CAM1 and CAM2 described above. The figure illustrates a user wearing a frame with CAM1 and CAM2 (562 and 563, respectively) coupled thereto, which measure ROIs on the right and left cheeks (ROIs 560 and 561, respectively). The measurements indicate that the left side of the face is colder than the right side of the face. Based on these measurements, and possibly additional data, the system detects the stroke and issues an alert. Optionally, the user's facial expression is slightly distorted and asymmetric, and a video camera provides additional data in the form of images that may help in detecting the stroke.

Figure 19:
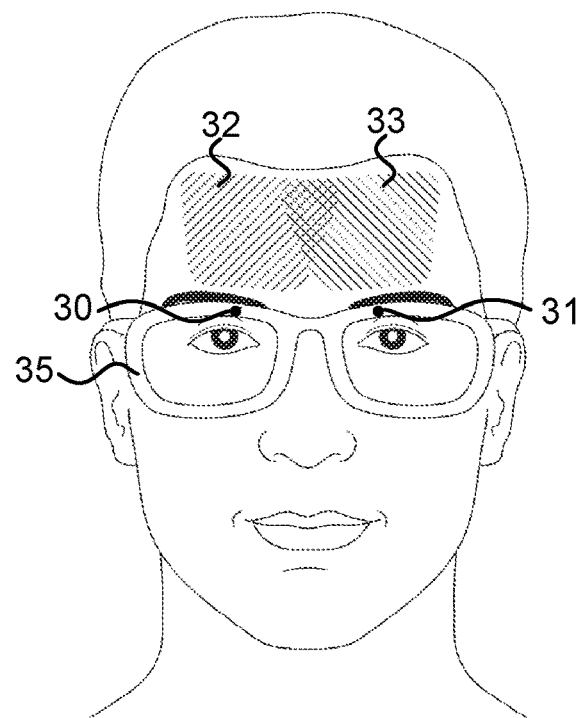
FIG. 19, FIG. 20, FIG. 21, and FIG. 22 illustrate head-mounted systems (HMSs) to measure various ROIs relevant to some of the embodiments describes herein.
Figure 20:
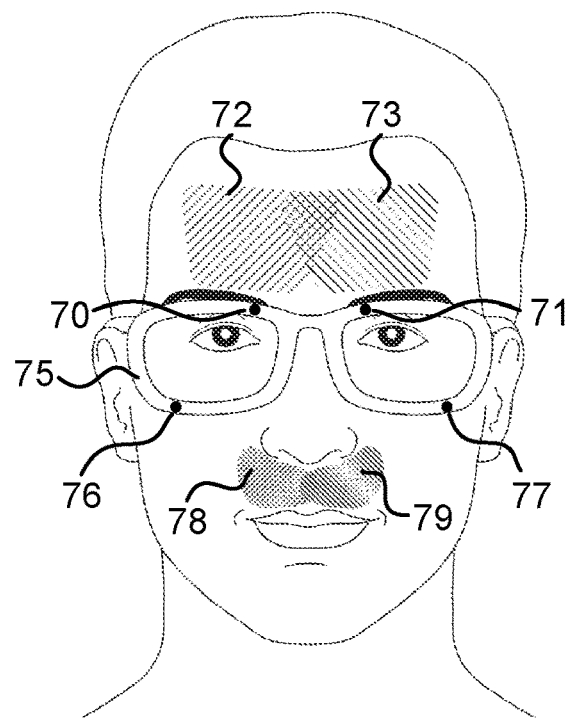
Figure 21:
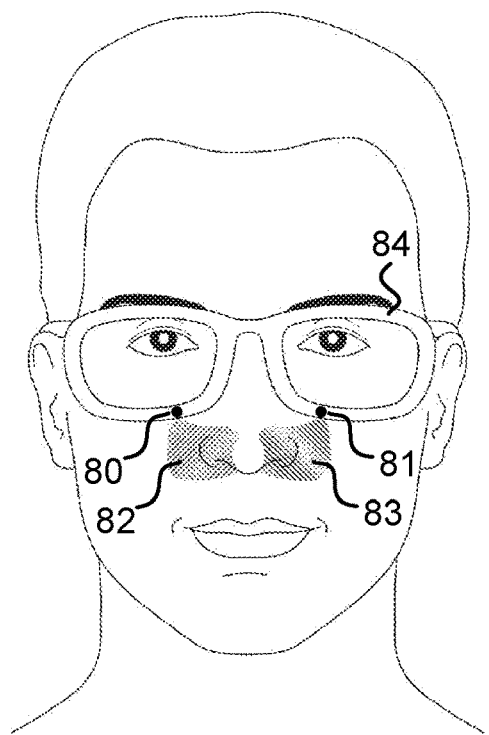
Figure 22:
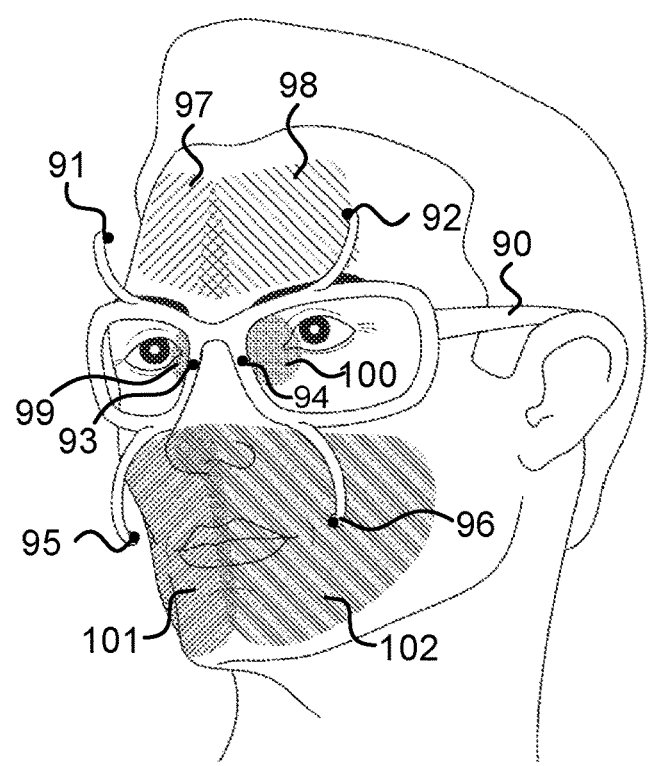

FIG. 19 to FIG. 22 illustrate HMSs that may be used to detect a stroke that include two or more CAMs. FIG. 19 illustrates inward-facing head-mounted cameras 30 and 31 that measure regions 32 and 33 on the forehead, respectively. FIG. 22 illustrates (i) inward-facing head-mounted cameras 91 and 92 that are mounted to protruding arms and measure regions 97 and 98 on the forehead, respectively, (ii) inward-facing head-mounted cameras 95 and 96, which are also mounted to protruding arms, which measure regions 101 and 102 on the lower part of the face, respectively, and (iii) head-mounted cameras 93 and 94 that measure regions on the periorbital areas 99 and 100, respectively.

Depending on the locations the at least first and second regions on the right and left sides of the head, CAM1 and CAM2 mentioned above may be located in specific locations with respect to the face. In one example, CAM1 and CAM2 are located outside the exhale stream of the mouth and/or the exhale streams of the nostrils. In another example, each of CAM1 and CAM2 is located less than 10 cm from the face and there are angles greater than 20° between the Frankfort horizontal plane and the optical axes of CAM1 and CAM2.

Measurements of additional regions on the head may be used to detect whether the user suffered from a stroke. In one embodiment, the at least one CAM is further configured to take thermal measurements of at least third and fourth regions on the right and left sides of the head ($TH_{R2}$ and $TH_{L2}$, respectively), and the computer is further configured to detect whether the user has suffered a stroke also based on $TH_{R2}$ and $TH_{L2}$ (in addition to $TH_{R1}$ and $TH_{L1}$). Optionally, the middles of the first and second regions are at least 1 cm above the middles of the third and fourth regions, respectively. Optionally, the third and fourth regions cover at least a portion of one of the following pairs of regions (which is not covered by the first and second regions): the right and left sides of the forehead, the right and left temples, the right and left cheeks, the right and left earlobes, behind the right and left ears, periorbital areas around the right and left eyes, the area of the right and left mastoid processes.

In one embodiment, the system optionally includes at least one outward facing head-mounted thermal camera ($CAM_{out}$), which is configured to take thermal measurements of the environment ($TH_{ENV}$). Optionally, the computer is further configured to also utilize $TH_{ENV}$ (in addition to $TH_{R1}$ and $TH_{L1}$) to detect whether the user has suffered a stroke.

There are various approaches that may be used by the computer, in different embodiments, to detect based on $TH_{R1}$ and $TH_{L1}$ whether the user has suffered a stroke. In some embodiments, detecting whether the user has suffered a stroke involves comparing $TH_{R1}$ and $TH_{L1}$ (referred to as current measurements) to previously taken thermal measurements (previous measurements), such as previously taken $TH_{R1}$ and $TH_{L1}$ of the user. Optionally, the previous measurements are taken at least fifteen minutes before the current measurements. Optionally, the previous measurements are taken at least one hour before the current measurements. Optionally, the previous measurements are taken at least one six hours before the current measurements. Optionally, the previous measurements are taken at least one day before the current measurements.

In some embodiments, the previous measurements are taken over a long period and are used to calculate baseline thermal values of regions of the face, and/or used to generate various models, which are used to detect a stroke, as discussed below. It is to be noted that discussion below regarding detection of the stroke based on $TH_{R1}$ and $TH_{L1}$ can be generalized to involve thermal measurements of other regions (such as $TH_{R2}$ and $TH_{L2}$ discussed above).

In one embodiment, the computer calculates a magnitude of thermal asymmetry of the head of the user based on a difference between $TH_{R1}$ and $TH_{L1}$, and compares the magnitude to a threshold. Responsive to the magnitude reaching the threshold, the computer detects that the user has suffered a stroke. Optionally, the difference between $TH_{R1}$ and $TH_{L1}$ needs to have reached the threshold (i.e., equal the threshold value or exceed it) for at least a predetermined minimal duration, such as at least one minute, at least five minutes, at least fifteen minutes, or at least some other period that is greater than 30 minutes. Optionally, the threshold is calculated based on previous magnitudes of thermal asymmetry of the head of the user, which were calculated based on previously taken $TH_{R1}$ and $TH_{L1}$ of the user. Thus, this threshold may be set according to a baseline thermal asymmetry that represents the typical difference in the temperatures of the first and second regions; a stroke may be detected when the thermal asymmetry becomes significantly different from this baseline.

In another embodiment, the computer calculates feature values and utilizes a model to calculate, based on the feature values, a value indicative of whether the user has suffered a stroke. At least some of the feature values are generated based on $TH_{R1}$ and $TH_{L1}$ of the user; examples of feature values that may be generated are given in the discussion regarding feature values that may be generated to detect a physiological response (herein suffering from a stroke is considered a type of physiological response). Optionally, at least some feature values are generated based on additional sources of information (other than the at least one CAM), such as additional thermal cameras, additional sensors that measure physiological signals of the user (e.g., heart rate or galvanic skin response), and/or additional sensors that measure the environment. Optionally, one or more of the feature values are indicative of the extent of difference between $TH_{R1}$ and $TH_{L1}$ of the user and previous $TH_{R1}$ and $TH_{L1}$ of the user, taken at least a certain period earlier (such as at least fifteen minutes earlier, one hour earlier, a day earlier, or more than a day earlier). Thus, these one or more feature values may represent a difference between the current thermal measurements and baseline thermal values for the first and second regions. Optionally, the model is generated based on data that includes previously taken $TH_{R1}$ and $TH_{L1}$ of the user and/or other users. Optionally, when data includes previously taken $TH_{R1}$ and $TH_{L1}$ of other users, at least some of the measurements of the other users were taken while they did not suffer from a stroke, and at least some of the measurements of the other users were taken while they did suffer from a stroke.

In another embodiment, the computer calculates a value indicative of a joint probability of $TH_{R1}$ and $TH_{L1}$ based on a model that includes distribution parameters calculated based on previously taken $TH_{R1}$ and $TH_{L1}$ of the user. Thus, the model describes a typical distribution of thermal measurements on regions of the user's head (when the user did not suffer from a stroke). The computer may compare the value indicative of the joint probability to a threshold, and responsive to the value being below the threshold, the computer detects that the user has suffered a stroke. The threshold may represent an atypical thermal asymmetry, with very low probability to normally occur, which warrants an alert of the possibility that the user has had a stroke.

In some embodiments described herein, detecting whether the user has suffered a stroke may involve calculating a change to thermal asymmetry on the head based on a change between thermal measurements taken at different times. This calculation can be performed in different ways, as described below.

In one embodiment, the computer calculates the change between the thermal measurements as follows: calculate a temperature difference between the first and second regions at time x ($\Delta T_x$) based on [$TH_{R1}$ and $TH_{L1}$] taken at time x, calculate a temperature difference between the first and second regions at time y ($\Delta T_y$) based on [$TH_{R1}$ and $TH_{L1}$] taken at time y, and calculate the output indicative of the change in the thermal asymmetry on the face based on a difference between $\Delta T_x$ and $\Delta T_y$.

The embodiment described above may optionally be implemented using a differential amplifier that receives $TH_{R1}$ and $TH_{L1}$ as inputs, and outputs the temperature difference between the first and second regions. Optionally, the at least one CAM is/are based on thermopile sensors. Alternatively, the at least one CAM is/are based on pyroelectric sensors. In one example, pairs of thermal sensor elements are wired as opposite inputs to a differential amplifier in order for the thermal measurements to cancel each other and thereby remove the average temperature of the field of view from the electrical signal. This allows the at least one CAM to be less prone to providing false indications of temperature changes in the event of being exposed to brief flashes of radiation or field-wide illumination. This embodiment may also minimize common-mode interference, and as a result improve the accuracy of the thermal cameras.

In another embodiment, the computer calculates the change between the thermal measurements as follows: the computer calculates a temperature change between $TH_{R1}$ taken at times $t_1$ and $t_2$ ($\Delta TH_{R1}$), calculates a temperature change between $TH_{L1}$ taken at times $t_1$ and $t_2$ ($\Delta TH_A$), and then calculates the output indicative of the thermal asymmetry on the face based on a difference between $\Delta TH_{R1}$ and $\Delta TH_{L1}$.

It is noted that sentences such as "calculate a difference between X and Y" or "detect a difference between X and Y" may be achieved by any function that is proportional to the difference between X and Y.

The detection of a stroke based on $TH_{R1}$ on $TH_{L1}$, and optionally other inputs, such as additional thermal measurements or additional physiological signals, may be sufficient, in some embodiments, to prompt the computer to take an action such as alerting the user, a caregiver, and/or emergency services. In other embodiments, the detection may be considered an indication that there is a risk that the user has suffered a stroke, and the computer may encourage the user to take a test (e.g., the FAST test described below or portions thereof), in order to validate the detection. Optionally, measurements and/or results taken during the test may be used in addition to $TH_{R1}$ and $TH_{L1}$ and the optional additional inputs, or instead of that data, in order to make a second, more accurate detection of whether the user has suffered from a stroke.

Upon detecting that the user has suffered from a stroke, in some embodiments, the computer may prompt the user to take a test to validate and/or increase the confidence in the detection. This test may involve performing one or more steps of a FAST test. Herein, FAST is an acronym used as a mnemonic to help detect and enhance responsiveness to the needs of a person having a stroke. The acronym stands for Facial drooping, Arm weakness, Speech difficulties and Time to call emergency services. Facial drooping involves a section of the face, usually only on one side, that is drooping and hard to move (often recognized by a crooked smile). Arm weakness typically involves an inability to raise one's arm fully. Speech difficulties typically involve an inability or difficulty to understand or produce speech.

Figure 7:
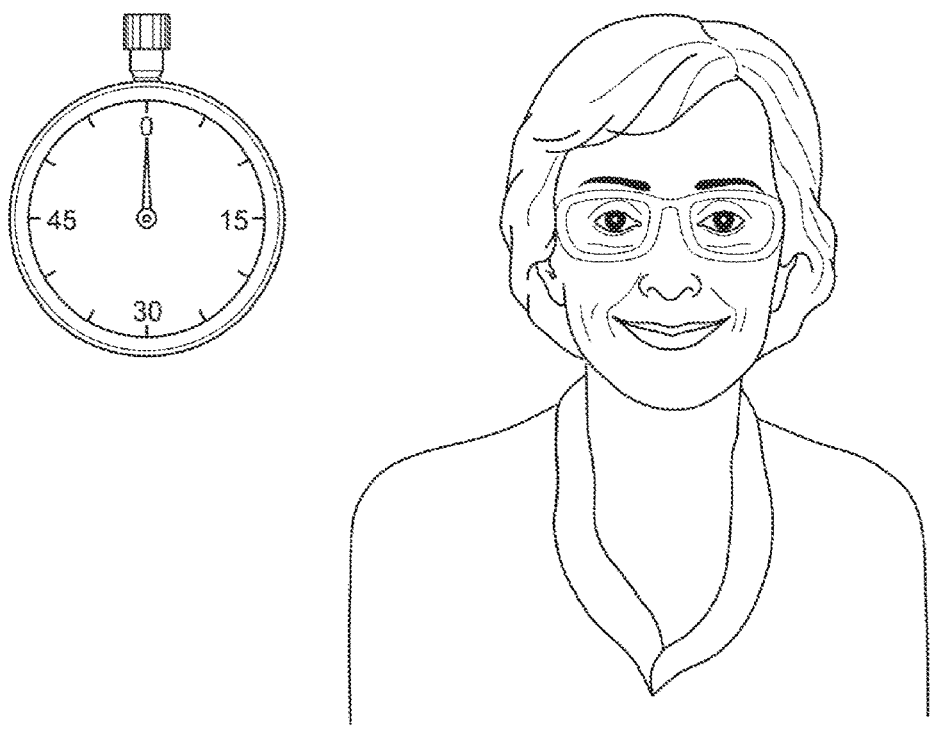
FIG. 7, FIG. 8, FIG. 9, and FIG. 10 illustrate physiological and behavioral changes that may occur following a stroke.
Figure 8:
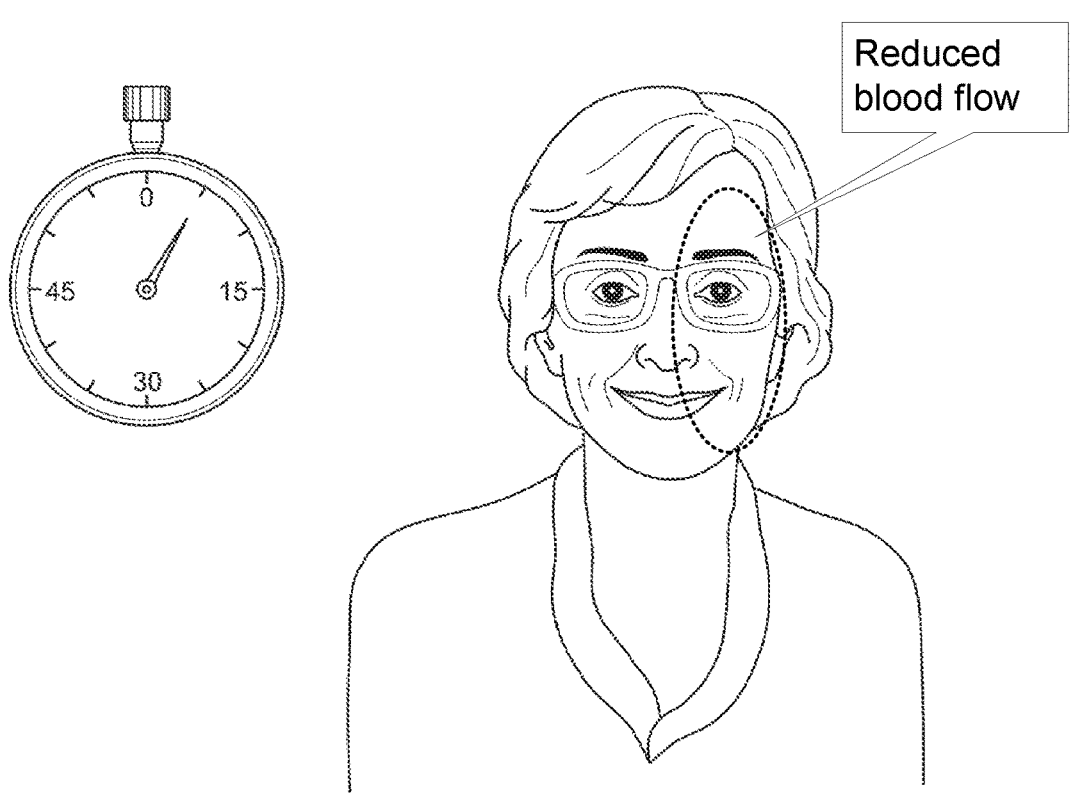
Figure 9:
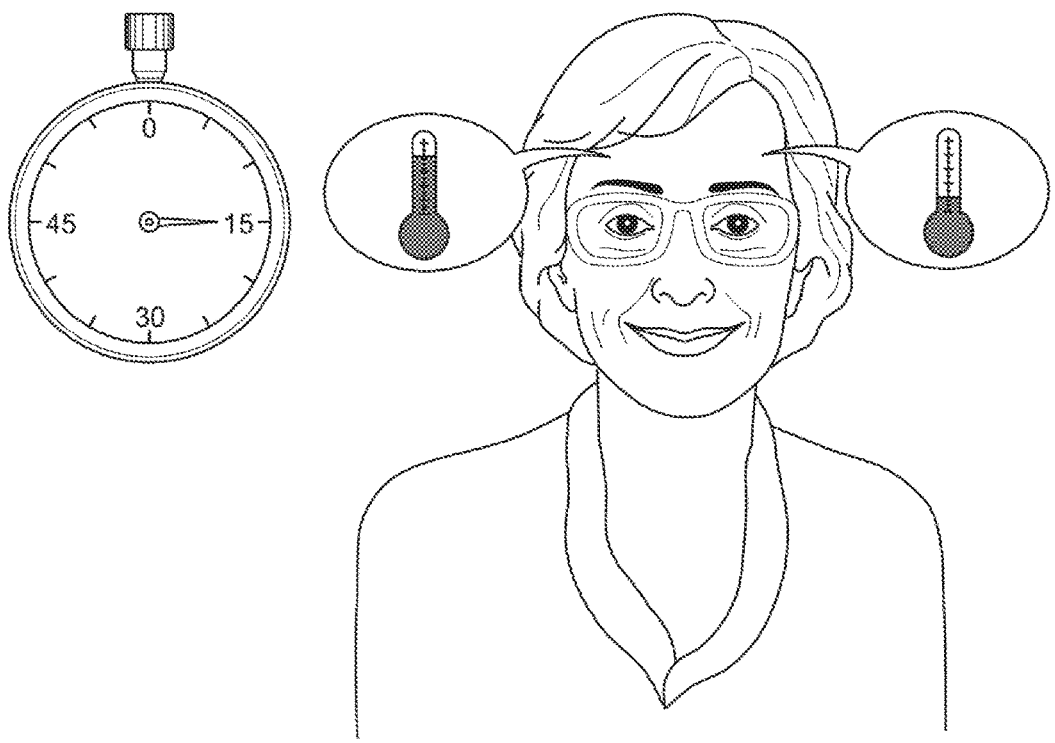
Figure 10:
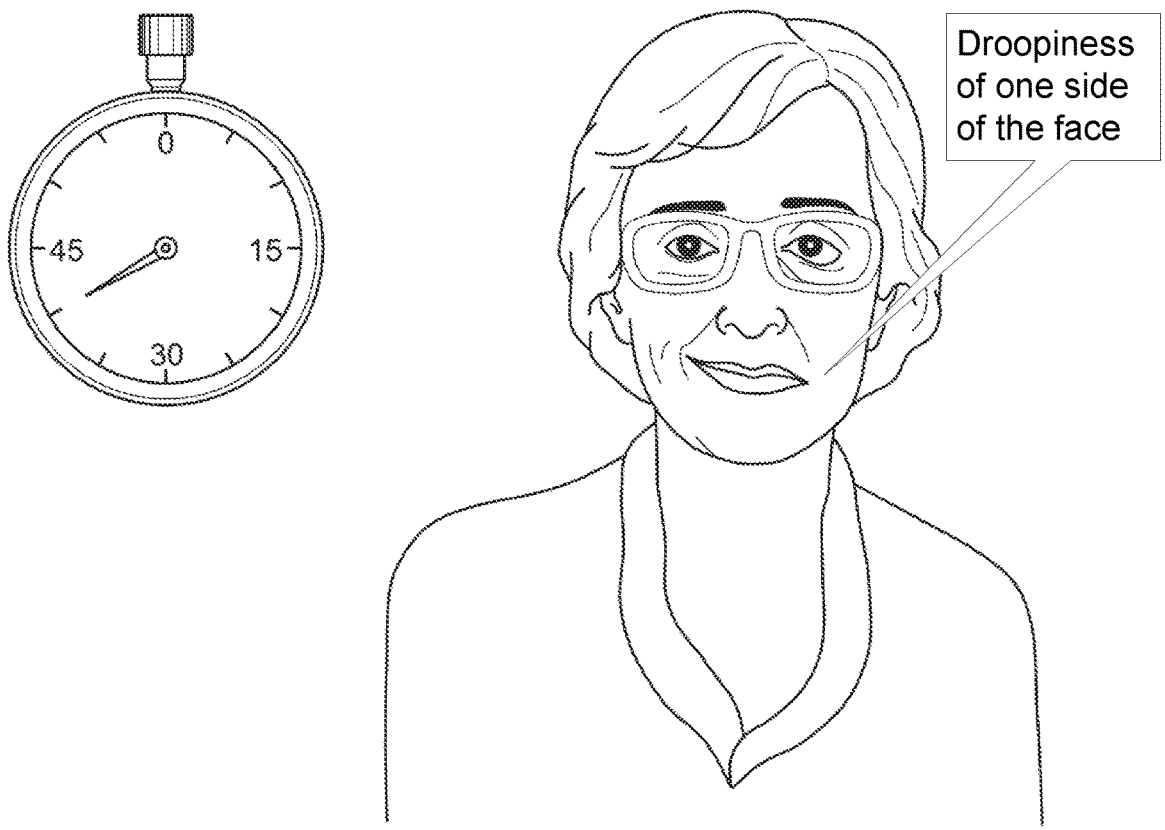

FIG. 7 to FIG. 10 illustrate physiological and behavioral changes that may occur following a stroke, which may be detected using embodiments described herein. FIG. 7 illustrates a person at time zero, at the very beginning of the onset of the stroke. At this time there may be no detectable signs of the stroke. FIG. 8 illustrates the person's state after 5 minutes since the beginning of the stroke. By this time, certain changes to the blood flow in the head, which were caused by the stroke, may be detectable. For example, the blood flow on one side of the face may decrease. FIG. 9 illustrates the person's state 15 minutes after the beginning of the stroke. At this time, temperature changes to regions of the face, which are due to the changes in blood flow, may be detectable. FIG. 10 illustrates the person's state 45 minutes after the beginning of the stroke. At this time, droopiness of one side of the face (e.g., due to reduced blood flow and impaired neurologic control) may be observable.

The following are some examples of steps that may be taken to further diagnose whether the user has suffered from a stroke (e.g., steps from a FAST test). Optionally, results of these steps may be used to further strengthen the computer's detection (e.g., to increase confidence in the detection) or change the detection (e.g., and decide the detection was a false alarm). Optionally, upon determining, based on one or more of the steps, that the user may have a suffered a stroke, the computer performs at least one of the following steps: (i) instruct the user to seek emergency medical assistance, (ii) connect the user through live video chat with a medical specialist, and (iii) automatically alert a predetermined person and/or entity about the user's condition.

Figure 11:
FIG. 11, FIG. 12, FIG. 13, and FIG. 14 illustrates various activities that a person may be requested to perform in order to determine whether the person has suffered from a stroke.
Figure 12:

In one embodiment, a camera (e.g., a cellphone camera or an inward-facing camera coupled to a frame worn by the user) takes images of at least a portion of the user's face. Optionally, the computer is further configured to (i) instruct the user, via a user interface, to smile and/or stick out the tongue, and (ii) detect, based on analysis of the images taken by the camera, whether a portion of one side of the user's face droops and/or whether the user was able to stick out the tongue. Detecting that the portion of the one side of the user's face droops may be done based on a comparison of the images of at least a portion of the user's face to previously taken images of at least the portion of the user's face, which were taken at least one hour before. Optionally, the computer utilizes a machine learning based model to determine whether the comparison indicates that the face droops. In this case, the model may be trained based on sets of images that include before and after images of people who suffered a stroke. Additionally or alternatively, detecting that the portion of the one side of the user's face droops is done using a machine learning-based model trained on examples of images of faces of people with a portion of one side of the face drooping. Optionally, detecting whether the tongue is sticking out may be done using image analysis and/or machine learning approaches (e.g., utilizing a model trained on previous images of the user and/or other users sticking out their tongue). FIG. 11 illustrates a user who is requested by a smartphone app to smile. Images of the user may be taken by the smartphone and analyzed in order to determine whether the user has smiled and/or to what extent the smile is considered "normal". Similarly, FIG. 12 illustrates a user who is requested by a smartphone app to stick out his tongue.

Figure 13:

In another embodiment, a microphone is used to record the user's speech. The computer is configured to (i) instruct the user, via a user interface, to speak (e.g., say a predetermined phrased), and (ii) detect, based on analysis of a recording of the user taken by the microphone, whether the user's speech is slurred, and/or whether a difference between the recording and previous recordings of the user exceeds a threshold that indicates excessively slurred or difficult. Optionally, the computer uses a model trained based on examples of peoples' normal and incoherent speech (e.g., recordings of people before and after they had a stroke). FIG. 13 illustrates a user who is requested by a smartphone app to say a sentence. The user's speech can be recorded by the smartphone and analyzed to detect slurry and/or uncharacteristic speech.

Figure 14:

In yet another embodiment, a sensor is used to take measurements indicative of at least one of movement and position, of at least one of the user's arms. Optionally, the computer is further configured to (i) instruct the user, via a user interface, to raise at least one the arms, and (ii) detect, based on analysis of the measurements taken by the sensor, whether an arm of the user drifts downward. In one example, the sensor is in a cellphone held by the user. In another example, the sensor is in a smartwatch or bracelet on the user's wrist. In still another example, the sensor is embedded in a garment worn by the user. FIG. 14 illustrates a user who is requested by a smartphone app to raise his arms. The user's movements can be detected by the smartphone in order to determine whether one arm falls. In the illustrated example, the user may be requested to raise the arms at least twice, each time holding the phone in a different hand. Such measurements can serve as a baseline to compare the rate of ascent and descent of each of the arms.

In still another embodiment, a sensor is used to take measurements indicative of how the user walks. Optionally, the computer is further configured to (i) instruct the user, via a user interface, to walk, and (ii) detect, based on analysis of the measurements taken by the sensor, whether a difference between the measurements taken by the sensor and previous measurements of the user taken by the sensor exceeds a threshold. Optionally, exceeding the threshold is indicative of a sudden loss of balance or coordination. In one example, the sensor is coupled to a frame worn on the user's head (e.g., a glasses frame). In another example, the sensor is in a cellphone, smartwatch, bracelet, garment, or shoe worn by the user.

Figure 15:
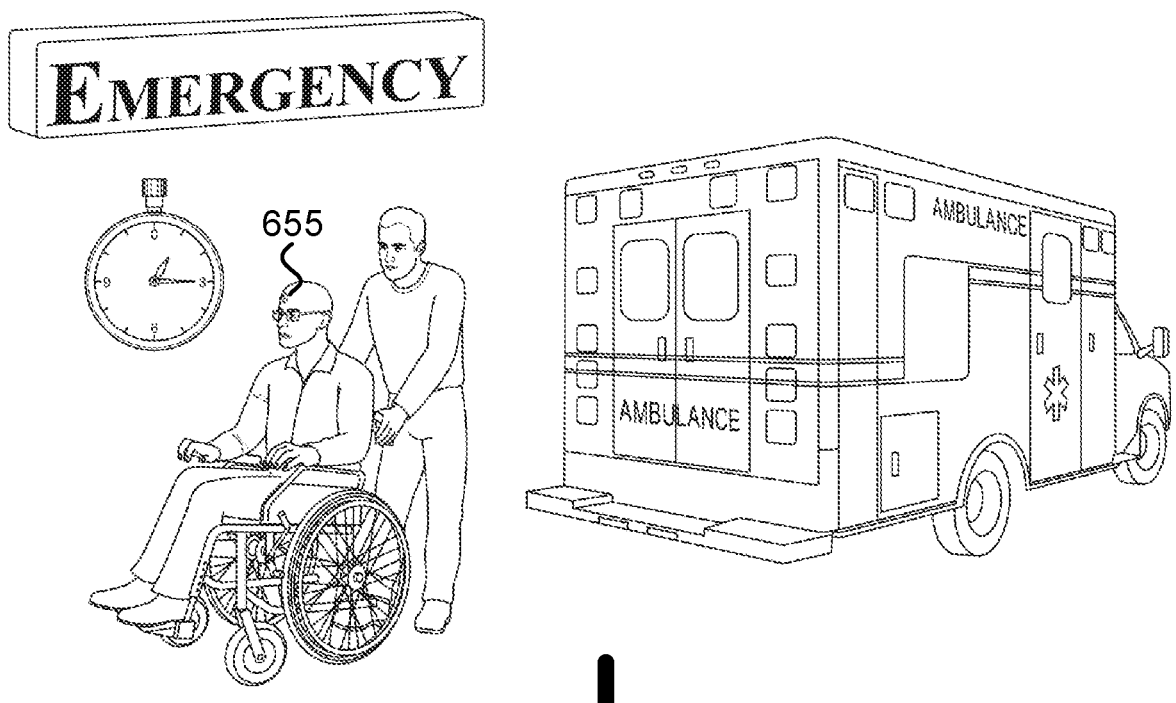
FIG. 15 and FIG. 16 illustrate the difference between a timely intervention in the event of a stroke and intervention that comes too late.
Figure 15:
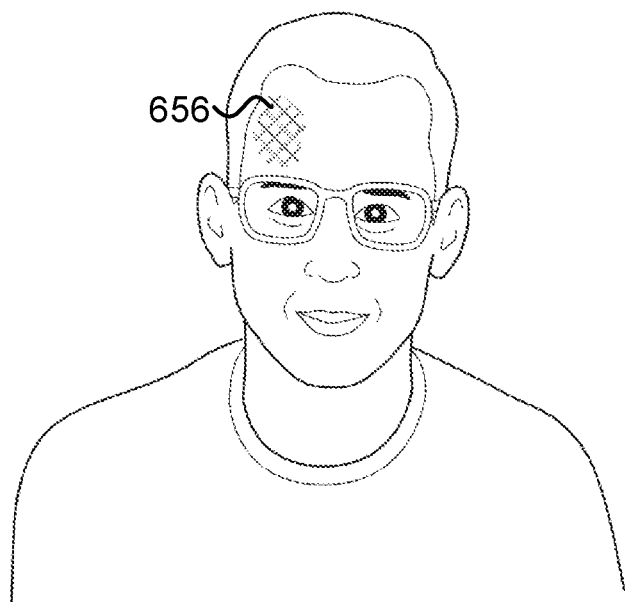
Figure 16:
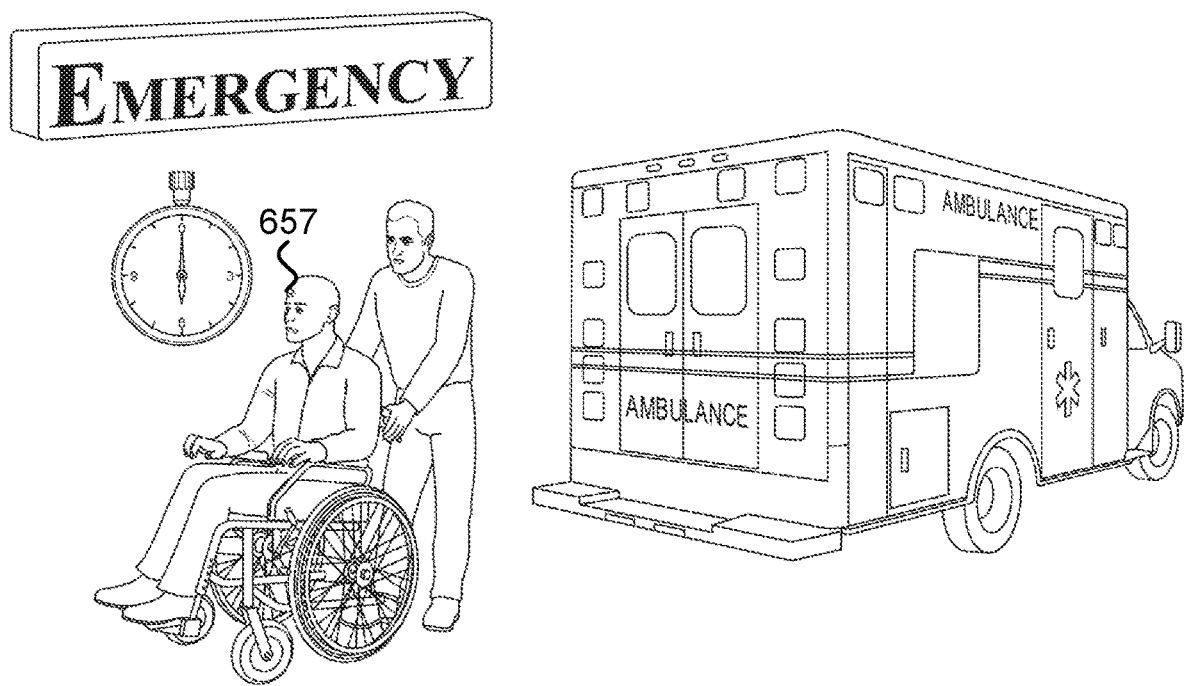
Figure 16:
Figure 16:
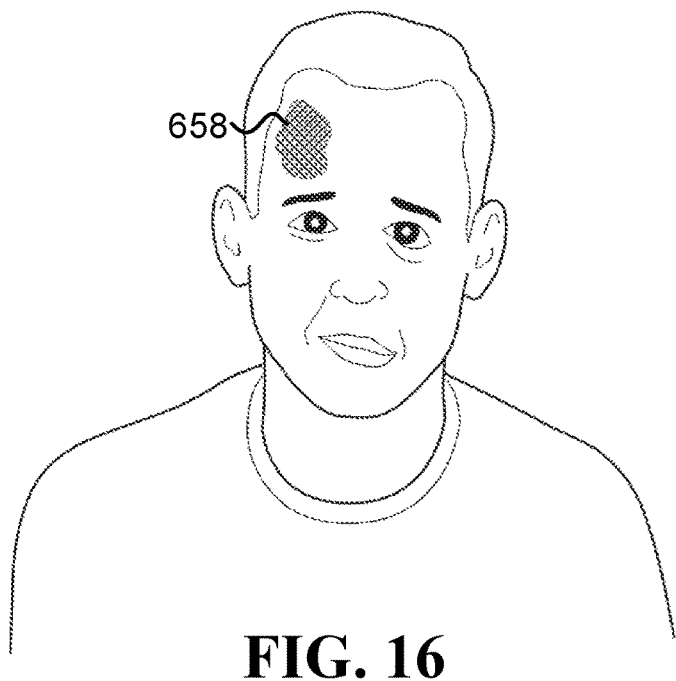

Early detection of a stroke, e.g., using one or more of the approaches described above, can be essential for minimizing the stroke-related damage. With strokes, it is certainly the case that time is of the essence. Early administration of treatment (e.g., within a few hours) can in many cases lead to minimal long term stroke-related damage. However, following a certain window of time (e.g., six hours since the start of the stroke), severe and irreversible long term damage may occur; impacting both quality of life and cost of care. FIG. 15 and FIG. 16 illustrate the difference between a timely intervention and intervention that comes too late. In FIG. 15, a patient arrives a short while (about an hour and fifteen minutes) after beginning of a stroke. This patient has moderate stroke damage (denoted by reference numeral 655). Intervention at this early stage is mostly successful, and after two months the patient has only slight long term damage (denoted by reference numeral 656), which involves a relatively small impact on the quality of life and a relatively low cost in terms of future medical expenses. FIG. 16 illustrates a case in which the patient arrives too late (e.g., six hours after the start of the stroke). In this scenario, the patient already has more severe stroke damage (denoted by reference numeral 657). Intervention at this late stage is mostly unsuccessful. Two months later, there is severe long term stroke-related damage, which involves a relatively large impact on the quality of life and a relatively high cost in terms of future medical expenses.

In addition to detecting a stroke, some embodiments may be used to detect an occurrence of a migraine attack. In one embodiment, the first and second regions are located above the user's eye level, and the computer is further configured to detect occurrence of a migraine attack based on asymmetry between $TH_{R1}$ and $TH_{L1}$. In another embodiment, the first and second regions are located above the user's eye level. The computer is further configured to generate feature values based on $TH_{R1}$ and $TH_{L1}$, and to utilize a model to calculate, based on the feature values, a value indicative of whether the user is experiencing a migraine attack or whether a migraine attack is imminent. Optionally, the model if generated based on previous $TH_{R1}$ and $TH_{L1}$ of the user taken while the user had a migraine attack or taken 30 minutes or less before the user had a migraine attack.

In some embodiments, a system configured to detect a stroke based on asymmetric changes to blood flow includes at least first and second devices and a computer. The first and second devices are located to the right and to the left of the vertical symmetry axis that divides the face of a user, respectively; the first and second devices are configured to measure first and second signals ($S_{BF1}$ and $S_{BF2}$, respectively) indicative of blood flow in regions to right and to the left of the vertical symmetry axis. The computer detects whether the user has suffered a stroke based on an asymmetric change to blood flow, which is recognizable in $S_{BF1}$ and $S_{BF2}$. Optionally, the system includes a frame configured to be worn on a user's head, and the first and second devices are head-mounted devices that are physically coupled to the right and left sides of the frame, respectively.

The first and second devices may be devices of various types. Optionally, the first and second devices are the same type of device. Alternatively, the first and second devices may be different types of devices. The following are some examples of various types of devices that can be used in embodiments described herein in order to measure a signal indicative of blood flow M a region of the body of the user.

In one embodiment, the first and second devices comprise first and second cameras, respectively. The first and second cameras are based on sensors comprising at least 3×3 pixels configured to detect electromagnetic radiation having wavelengths in at least a portion of the range of 200 nm to 1200 nm. Optionally, the asymmetric changes to blood flow lead to asymmetric facial skin color changes to the face of the user. Optionally, the system includes first and second active light sources configured to illuminate the first and second legions, respectively. In one example, the first and second devices and first and second active light sources are head-mounted, and the first and second active light sources are configured to illuminate the first and second regions with electromagnetic radiation having wavelengths in at least a portion of the range of 800 nm to 1200 nm.

In addition to the first and second cameras mentioned above, some embodiments may include first and second outward facing cameras that take images of the environment to the right and left of the user's head, respectively. Optionally, the computer utilizes the images to detect whether the user has suffered a stroke. Optionally, the images of the environment are indicative of illumination towards the face, images taken by the inward-facing cameras are indicative of reflections from the face. Thus, the images of the environment may be used to account, at least in part, for variations in ambient light that may cause errors in detections of blood flow.

In another embodiment, the first and second devices function as imaging photoplethysmography devices, and/or the first and second devices function as pulse oximeters.

There are various types of devices that may be used in embodiments described herein, and ways in which the devices may be attached to the user and/or located the user's proximity. In one example, the first and second device may be head-mounted devices, such as devices physically coupled to a frame worn on the user's head (e.g., a frame of smartglasses, such as augmented reality glasses, virtual reality glasses, or mixed reality glasses). In another example, the first and second devices are embedded in a garment worn by the user (e.g., a smart shirt) or some other wearable accessory (e.g., a necklace, bracelets, etc.). In yet another, the first and second devices may be located in headrests of a chair in which the user sits. In still another example, the first and second devices are attached to walls (e.g., of a vehicle cabin in which the user sits or a room in which the user spends time). In yet another example, the first and second devices may be coupled to robotic arms. Optionally, the robotic arms may be used to move and/or orient the devices in order to account for the user's movements, which may enable the first and second devices to measure the same regions on the user's head despite the user's movement.

The first and second devices may be utilized to measure various regions on the right and left sides of the user's head. In one embodiment, the regions on the right and left sides include portions of the right and left temples, respectively. In another embodiment, the regions on the right and left sides include portions of the right and left sides of the forehead, respectively. Optionally, the center of the region on the right is at least 3 cm from the center of the region on the left. In still another embodiment, the regions on the right and left sides include portions of the right and left cheeks, respectively. In still another embodiment, the regions on the right and left sides include areas behind the right and left ears, respectively. Optionally, the areas behind the right and left ears are below the hairline and cover at least a portion of the mastoid process in their respective sides of the head.

FIG. 17a illustrates an embodiment of a system that includes multiple pairs of right and left cameras, and locations on the face that they may be used to measure. The cameras illustrated in the figure are coupled to a frame worn by the user, which may be, for example, any of the cameras mentioned herein. The illustrated example include: (i) cameras 641a and 641b that are coupled to the right and left sides of the top of the frame, respectively, which measure ROIs 644a and 644b on the right and left of the forehead, respectively; (ii) cameras 642a and 642b that are coupled to the right and left sides of the bottom of the frame, respectively, which measure ROIs 645a and 645b on the right and left cheeks, respectively; and (iii) cameras 643a and 643b that are coupled to the frame near the right and left sides of the nose, respectively, which measure ROIs 646a and 646b in the right and left periorbital regions, respectively.

FIG. 17b illustrates a stroke sign 647, which involves decreased blood flow in the forehead, and may be detected using the system illustrated in FIG. 17a. Another stroke sign that may be detected by the system illustrated in FIG. 17c is stroke sign 648, which involves decreased temperature in the periorbital region.

Figure 18A:
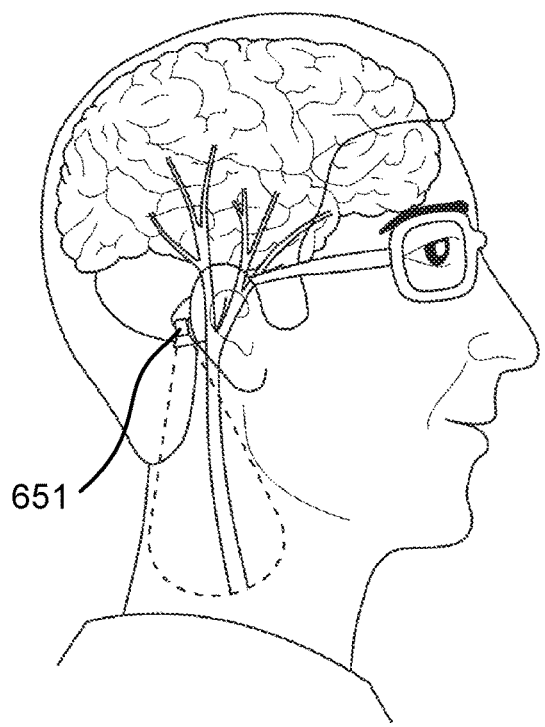
FIG. 18a and FIG. 18b illustrate embodiments of a system with a head-mounted camera located behind the ear.
Figure 18B:
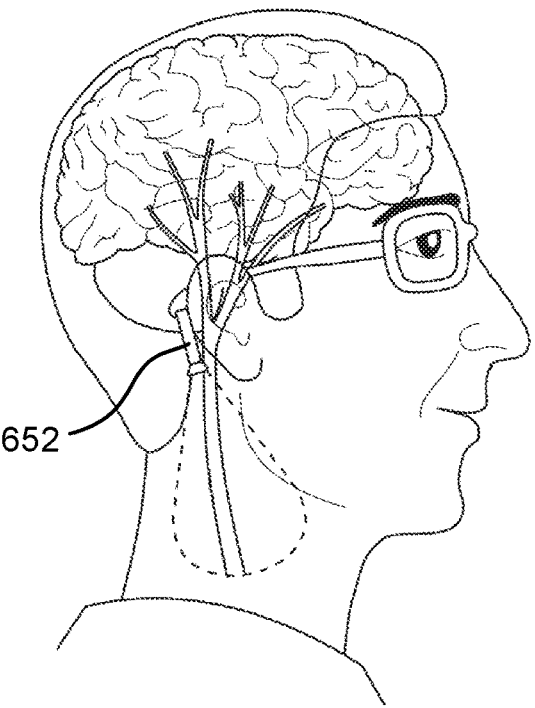

FIG. 18a illustrates a system in which the first and second devices are head-mounted cameras that are located behind the ears. The figure illustrates cameras 651, which may be a downward facing video camera that takes images that include portions of the side of the neck. FIG. 18b illustrates a variant of the system illustrated in FIG. 18a in which camera 652 is a downward-facing camera that includes an extender body which enables the camera to move beyond the hairline in order to obtain unobstructed images of the side of the neck.

Figure 18C:
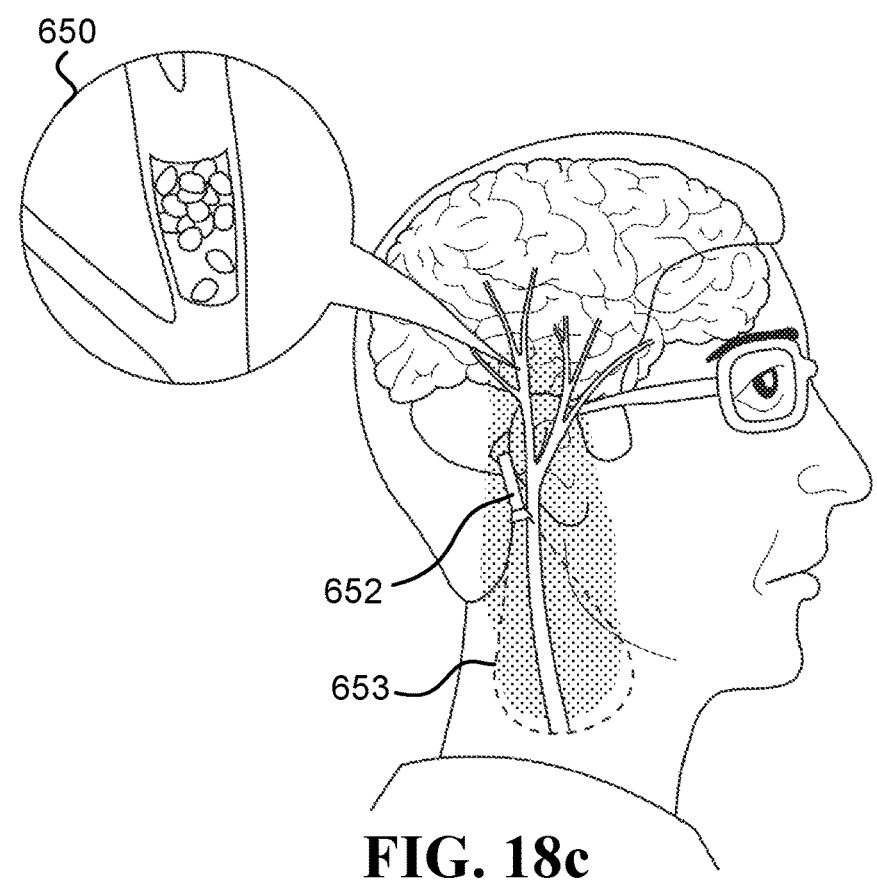
FIG. 18c illustrates an ischemic stroke that restricts the blood flow to the side of the head, which may be detected by embodiments described herein.

FIG. 18c illustrates ischemic stroke 650, which restricts the blood flow to the side of the head (illustrated as patch 653), which may be detected based on measurements of device 652 in order to alert about the user having suffered from a stroke.

Various types of values, which are indicative of blood flow (and taken by the first or second devices), can be determined based on a signal, which is denoted $S_{BF}$ in the discussion below. $S_{BF}$ may be, for example, aforementioned $S_{BF1}$ or $S_{BF2}$. Propagation of a cardiac pulse wave can lead to changes in the blood flow, with increased blood flow as a result of blood pumped during the systole, and lower blood flow at other times (e.g., during diastole). The changes in blood flow often manifest as changes to values in $S_{BF}$. For example, higher blood flow may correspond to increased intensity of certain colors of pixels (when $S_{BF}$ includes images), temperatures of pixels (when $S_{BF}$ includes thermal images), or increased absorption of certain wavelengths (when $S_{BF}$ includes measurements of a photoplethysmography device).

In some embodiments, calculating a statistic of $S_{BF}$ may provide an indication of the extent of the blood flow. For example, the statistic may be an average value (e.g., average pixel values), which is a calculated over a period, such as ten seconds, thirty seconds, or a minute. For example, in an embodiment in which the devices are cameras and $S_{BF}$ includes images, the average hue of pixels in the images can be indicative of the blood flow (e.g., a redder hue may correspond to more intense blood flow). In an embodiment in which the devices are thermal sensors and $S_{BF}$ includes thermal images, the average temperature of pixels in the thermal images can be indicative of the blood flow (e.g., a higher average temperature may correspond to more intense blood flow).

In other embodiments, analysis of propagation of cardiac pulse waves, as manifested in the values of $S_{BF}$, can be used to provide indications of the extent of blood flow. When $S_{BF}$ includes multiple pixels values (e.g., images or thermal images), propagation of a pulse wave typically involves an increase in pixel values that correspond to a period of a high blood flow during the pulse wave (e.g., when blood flow is driven by a systole) followed by a decrease in pixel values that correspond to a period of a lower blood flow during the pulse wave (e.g., decreasing towards a diastolic trough). The speed at which the pulse wave propagates along a segment of the images of $S_{BF}$ is indicative of the speed of blood flow in the segment depicted in the images. For example, the speed at which a peak (e.g., corresponding to the systole) is seen to propagate in the images is directly correlated with the blood flow.

Another parameter indicative of blood flow that can be derived from analysis of a propagation of a pulse wave, as it is manifested in values of $S_{BF}$, is the amplitude of the signal. For example, signals that display a periodic increase and decrease in values of $S_{BF}$, which corresponds to the heart rate, can be analyzed to determine the difference in values (e.g., difference in color, temperature, or intensity) between the peak and the trough observed in the values of $S_{BF}$ during the transition of a pulse wave. In some embodiments, the amplitude of the signal (e.g., the difference between the value at the peak and the value at the trough) is correlated with the blood flow. In one example, the higher the amplitude of the signal, the higher the blood flow.

Another parameter indicative of blood flow that can be derived from analysis of a propagation of a pulse wave, as it is manifested in values of $S_{BF}$, is the extent to which pixels in images (or thermal images) display a periodic change to their values that reaches a certain threshold. For example, the area on the face in which the periodic facial skin color changes (which correspond to the cardiac pulse) reach a certain threshold is correlated with the blood flow. The higher the blood flow, the larger the area.

The extent of Blood flow (e.g., the speed at which the blood flows) is correlated with the times at which a pulse wave is detected at different locations of the body. Typically, the farther a location from the heart, the later the pulse wave is detected (e.g., detection of a pulse wave may correspond to the time at which a systolic peak is observed). This phenomenon can be utilized, in some embodiments, to calculate values indicative of blood flow based on the difference in times at which pulse waves are detected at different locations. For example, analysis of one or more $S_{BF}$ signals, which include values that are indicative of propagation of a pulse wave at various locations, can determine the difference in time ($\Delta t$) between detection of a pulse wave at different locations. The value of $\Delta t$ is typically correlated with the blood flow: the higher the blood flow, the smaller $\Delta t$ is expected to be.

The computer is configured, in some embodiments, to detect whether the user has suffered a stroke based on an asymmetric change to blood flow, which is recognizable in $S_{BF1}$ and $S_{BF2}$.

Herein, sentences of the form "asymmetric change to blood flow recognizable in $S_{BF1}$ and $S_{BF2}$" refer to effects of blood flow that may be identified and/or utilized by the computer, which are usually not recognized by the naked eye (in the case of images), but are recognizable algorithmically when the signal values are analyzed. For example, blood flow may cause facial skin color changes (FSCC) that corresponds to different concentrations of oxidized hemoglobin due to varying blood pressure caused by the cardiac pulse Similar blood flow dependent effects may be viewed with other types of signals (e.g., slight changes in cutaneous temperatures due to the flow of blood.

When the blood flow on both sides of the head and/or body are monitored, asymmetric changes may be recognized. These changes are typically different from symmetric changes that can be caused by factors such as physical activity (which typically effects the blood flow on both sides in the same way). An asymmetric change to the blood flow can mean that one side has been affected by an event, such as a stroke, which does not influence the other side. In one example, the asymmetric change to blood flow comprises a change in blood flow velocity on left side of the face that is 10% greater or 10% lower than a change in blood flow velocity on one right side of the face. In another example, the asymmetric change to blood flow comprises a change in the volume of blood the flows during a certain period in the left side of the face that is 10% greater or 10% lower than the volume of blood that flows during the certain period in the right side of the face. In yet another example, the asymmetric change to blood flow comprises a change in the direction of the blood flow on one side of the face (e.g., as a result of a stroke), which is not observed at the symmetric location on the other side of the face.

In some embodiments, the computer detects whether the user has suffered a stroke based on a comparison between values belonging to a current set of $S_{BF1}$ and $S_{BF2}$ and values belonging to a previous set of $S_{BF1}$ and $S_{BF2}$ of the user. Optionally, the previous set was measured at least fifteen minutes before the current set, at least one hour before the current set, or at least one day before the current set. Optionally, the previous set serves to establish baseline blood flow values for both regions when the user was assumed not to be effected by a stroke.

In one embodiment, the computer uses a machine learning model to detect whether the user has suffered a stroke. Optionally, the computer is configured to: generate feature values based on data comprising a current set of $S_{BF1}$ and $S_{BF2}$ and a previous set of $S_{BF1}$ and $S_{BF2}$ of the user, and utilize the model to calculate, based on the feature values, a value indicative of whether the user has suffered a stroke. Optionally, the previous set was measured at least one hour before the current set. Optionally, at least some of the feature values are indicative of changes to the blood flow in each of the first and second regions between the time the current set was measured and when the previous set was measured.

In one embodiment, the model was generated based on data comprising "after" sets of $S_{BF1}$ and $S_{BF2}$ of other users and corresponding "before" sets of $S_{BF1}$ and $S_{BF2}$ of the other users. In these embodiments, the "after" sets were measured after the other users had suffered from a stroke (and the "before" sets were measured before they suffered from the stroke). Thus, training samples generated based on this data can reflect some of the types of asymmetric changes to blood flow that characterize suffering from a stroke.

In the event that a stroke is detected, the computer may prompt the user to take a FAST test (or portions thereof), as described above. In another example, the computer may suggest to the user to take images of the retinas. In this example, the computer is further configured to compare the images of the retinas with previously taken images of the retinas of the user, and to detect whether the user has suffered a stroke based on the comparison. Optionally, the comparison can take into account diameter of retinal arteries, swelling and blurring of the boundaries of the optic disk.

Blood flow usually exhibits typical patterns in the user's body. When a blood flow pattern changes, this usually happens in a predictable way (e.g., increase in blood flow due to physical activity, certain emotional responses, etc.). When a person's blood flow changes in an atypical way, this may indicate an occurrence of a certain medical incident, such as a stroke. Therefore, atypical blood flow patterns should be detected in order to investigate their cause.

In some embodiments, a system configured to detect an atypical blood flow pattern in the head of a user includes one or more head-mounted devices and a computer. The one or more head-mounted devices are configured to measure at least three signals ($S_{BF1}$, $S_{BF2}$ and $S_{BF3}$, respectively), indicative of blood flow in at least three corresponding regions of interest on the head ($ROI_1$, $ROI_2$, and $ROI_3$, respectively) of a user. Optionally, the centers of $ROI_1$, $ROI_2$ and $ROI_3$ are at least 1 cm away from each other. Optionally, the one or more head-mounted devices do not occlude $ROI_1$, $ROI_2$ and $ROI_3$.

There are various types of devices the one or more head-mounted devices may be. Optionally, each of the one or more head-mounted devices are the same type of device. Alternatively, when the one or more head-mounted devices are a plurality of devices, the plurality of devices may be of different types of devices. The following are some examples of various types of devices that can be used in embodiments described herein in order to measure a signal indicative of blood flow in a region of the body of the user.

In one embodiment, the one or more head-mounted devices include a camera that is based on a sensor comprising at least 3×3 pixels configured to detect electromagnetic radiation having wavelengths in at least a portion of the range of 200 nm to 1200 nm. Optionally, the system includes one or more light sources configured to $ROI_1$, $ROI_2$ and $ROI_3$. Optionally, the one or more light sources are configured to illuminate $ROI_1$, $ROI_2$ and $ROI_3$ with electromagnetic radiation having wavelengths in at least a portion of the range of 800 nm to 1200 nm.

In another embodiment, the one or more head-mounted devices include a device that functions as an imaging photoplethysmography device and/or a device that functions as a pulse oximeter.

The computer is configured, in one embodiment, to generate a blood flow pattern based on a current set of $S_{BF1}$, $S_{BF2}$ and $S_{BF3}$. The computer is also configured to calculate, based on a set of previous blood flow patterns of the user, a value indicative of the extent to which the blood flow pattern is atypical. Optionally, the set of previous blood flow patterns were generated based on sets of $S_{BF1}$, $S_{BF2}$ and $S_{BF3}$ measured at least one day prior to when the current set was measured. That is, the previous sets of blood flow patterns were generated based on data the comprises $S_{BF1}$, $S_{BF2}$ and $S_{BF3}$ measured at least one day before $S_{BF1}$, $S_{BF2}$ and $S_{BF3}$ in the current set. Optionally, the previous sets of blood flow patterns were generated based on data that was measured when the user was not known to be in an atypical condition (e.g., the user was considered healthy at the time).

In some embodiments, the value indicative of the extent to which the blood flow pattern is atypical is compared to a threshold. If the value reaches the threshold, the computer may take different actions. In one embodiment, responsive to the value reaching the threshold, the computer issues an alert. For example, the computer may send a message to a predetermined recipient (e.g., emergency services or a caregiver). In another example, the computer may command a user interface to generate an alert (e.g., a beeping sound, a text message, or vibrations. In another embodiment, responsive to the value reaching the threshold, the computer may prompt the user to perform a test, using an electronic device, to determine whether the user has suffered a stroke. For example, the user may be prompted to perform a FAST test (or portions thereof), as described elsewhere in this disclosure.

There are various ways in which a blood flow pattern may be generated based on $S_{BF1}$, $S_{BF2}$ and $S_{BF3}$. In one embodiment, $S_{BF1}$, $S_{BF2}$ and $S_{BF3}$ themselves may constitute the pattern. Optionally, the blood flow pattern comprises a time series that is indicative of blood flow at each of $ROI_1$, $ROI_2$, and $ROI_3$. In one example, the blood flow pattern may be a time series of the raw (unprocessed) values of $S_{BF1}$, $S_{BF2}$ and $S_{BF3}$ (e.g., a time series of values measured by the one or more head-mounted devices). In another example, blood flow pattern may be a time series of processed values, such as various statistics of $S_{BF1}$, $S_{BF2}$ and $S_{BF3}$ at different points of time (e.g., average pixel intensity for images taken by a camera at different points of time).

In another embodiment, the blood flow pattern may include statistics of the values of $S_{BF1}$, $S_{BF2}$ and $S_{BF3}$, such as values representing the average blood flow during the period $S_{BF1}$, $S_{BF2}$ and $S_{BF3}$ were measured. Values in a blood flow pattern, such as the statistics of the values of $S_{BF1}$, $S_{BF2}$ and $S_{BF3}$ may be of various types of values. The following are some examples of types of values that may be used in a "blood flow pattern". In one example, the blood flow pattern includes one or more values that describe the intensity of blood flow at each of $ROI_1$, $ROI_2$, and/or $ROI_3$. In another example, the blood flow pattern includes one or more values that describe the amplitude of changes to measurement values at $ROI_1$, $ROI_2$, and/or $ROI_3$, such as the amplitude of periodic changes (which correspond to the heart rate) to color, temperature, and/or absorbance at certain wavelengths. In yet another example, the blood flow pattern includes one or more values that describe the speed at which a pulse wave propagates through $ROI_1$, $ROI_2$, and/or $ROI_3$. In still another example, the blood flow pattern includes one or more values that describe the direction at which a pulse wave propagates in $ROI_1$, $ROI_2$, and/or $ROI_3$.

There are various ways in which the computer may utilize the previous blood flow patterns in order to determine the extent to which the blood flow pattern is atypical.

In one embodiment, the computer calculates the value indicative of the extent to which the blood flow pattern is atypical by calculating distances between the blood flow pattern and each of the previous blood flow patterns, and determining a minimal value among the distances. The larger this minimal value, the more atypical the blood flow pattern may be considered (due to its difference from all previous blood flow patterns considered). In one example, in which blood flow patterns include time series data, the distances may be calculated by finding the extent of similarity between the blood flow pattern and each of the previous blood flow patterns (e.g., using methods described in Wang, Xiaoyue, et al. "Experimental comparison of representation methods and distance measures for time series data", Data Mining and Knowledge Discovery 26.2 (2013): 275-309). In another example, distances between blood flow patterns that include dimensional data, such as blood flow patterns that may be represented as vectors of values, may be calculated using various similarity metrics known in the art such as Euclidean distances or vector dot products.

In another embodiment, the computer calculates, based on the previous sets of $S_{BF1}$, $S_{BF2}$ and $S_{BF3}$, parameters of a probability density function (pdf) for blood flow patterns. For example, each blood flow pattern may be represented as a vector of values and the pdf may be a multivariate distribution (e.g., a multivariate Gaussian) whose parameters are calculated based on vectors of values representing the previous blood flow patterns. Given a vector of values representing the blood flow pattern, the probability of the vector of values is calculated based on the parameters of the pdf. Optionally, if the probability is below a threshold, the blood flow pattern may be considered atypical. Optionally, the threshold is determined based on probabilities calculated for the vectors of values representing the previous blood flow patterns, such the at least a certain proportion of the vectors have a probability that reaches the threshold. For example, the certain proportion may be at least 75%, at least 90%, at least 99%, or 100%.

In yet another embodiment, the computer calculates the value indicative of the extent to which the blood flow pattern is atypical using a model of a one-class classifier generated based on the set of previous blood flow patterns.

In still another embodiment, the computer calculates feature values and utilizes a model to calculate, based on the feature values, the value indicative of the extent to which the blood flow pattern is atypical. Optionally, one or more of the feature values are generated based on the blood flow pattern, and at least one of the feature values is generated based on the previous blood flow patterns. Optionally, feature values generated based on a blood flow pattern include one or more of the values described in examples given above as examples of values in a blood flow pattern. Optionally, one or more of the feature values describe differences between values representing the blood flow pattern, and values representing the previous blood flow patterns. The model is generated based on samples, with each sample comprising: (i) feature values calculated based on a blood flow pattern of a certain user, from among a plurality of users, and previous blood flow patterns of the certain user, and (ii) a label indicative of an extent to which the blood flow pattern of the certain user is atypical. Additional details regarding generating the model can be found herein in the discussion regarding machine learning approaches that may be used to detect a physiological response.

In some embodiments, the computer may use additional inputs to determine whether the blood flow pattern is an atypical blood flow pattern. In one example, the computer may receive measurements of various physiological signals (e.g., heart rate, respiration, or brain activity) and use these measurements to generate at least some of the feature values. In another example, the computer may receive an indication of a state of the user and to generate one or more of the feature values based on the indication. Optionally, the state of the user is indicative of at least one of the following: an extent of physical activity of the user, and consuming a certain substance by the user (e.g., alcohol or a drug).

The physiological and emotional state of a person can often be associated with certain cortical activity. Various phenomena, which may be considered abnormal states, such as anger or displaying symptomatic behavior of Attention Deficit Disorder (ADD) or Attention Deficit Hyperactivity Disorder (ADHD), are often associated with certain atypical cortical activity. This atypical cortical activity can change the blood flow patterns on the face, and especially on the forehead area. Thus, there is a need for a way to detect such changes in blood flow in real world day-to-day situations. Preferably, in order to be comfortable and more aesthetically acceptable, these measurements should be taken without involving direct physical contact with the forehead or occluding it.

In some embodiments, a system configured to detect an attack characterized by an atypical blood flow pattern includes the one or more head-mounted devices (described above) and a computer. The one or more head-mounted devices are configured to measure at least three signals ($S_{BF1}$, $S_{BF2}$ and $S_{BF3}$, respectively), indicative of blood flow in at least three corresponding regions of interest on the head ($ROI_1$, $ROI_2$, and $ROI_3$, respectively) of a user. Optionally, the centers of $ROI_1$, $ROI_2$ and $ROI_3$ are at least 1 cm away from each other. Optionally, the one or more head-mounted devices do not occlude $ROI_1$, $ROI_2$ and $ROI_3$. Optionally, $ROI_1$, $ROI_2$ and $ROI_3$ are on the same side of the face. Alternatively, $ROI_1$, $ROI_2$ and $ROI_3$ are on all on the same side of the face. For example, ROI' may be on the left side of the face, and $ROI_2$ on the right side of the face.

The computer is configured, in one embodiment, to calculate a value, based on $S_{BF1}$, $S_{BF2}$, and $S_{BF3}$, indicative of whether the user is in a normal or abnormal state.

In one embodiment, the state of the user is determined by comparing a blood flow pattern generated based on $S_{BF1}$, $S_{BF2}$, and $S_{BF3}$ to reference blood flow patterns of the user that include at least one reference blood flow pattern that corresponds to the normal state and at least one reference blood flow pattern that corresponds to the abnormal state. Optionally, a reference blood flow pattern is determined from previous $S_{BF1}$, $S_{BF2}$, and $S_{BF3}$ of the user, taken while the user was in a certain state corresponding to the reference blood flow pattern (e.g., normal or abnormal states). Optionally, if the similarity reaches a threshold, the user is considered to be in the state to which the reference blood flow pattern corresponds.

In another embodiment, the computer determines that the user is in a certain state (e.g., normal or abnormal) by generating feature values (at least some of which are generated based on $S_{BF1}$, $S_{BF2}$, and $S_{BF3}$) and utilizing a model to calculate, based on the feature values, the value indicative of whether the user is in a normal or abnormal state. Optionally, the model is trained based on samples, each comprising feature values generated based on previous $S_{BF1}$, $S_{BF2}$, and $S_{BF3}$ of the user, taken while the user was in the certain state.

In yet another embodiment, $S_{BF1}$, $S_{BF2}$, and $S_{BF3}$ comprise time series data, and the computer calculates the value indicative of whether the user is in a normal or abnormal state based on comparing the time series to at least first and second reference time series, each generated based on previously taken $S_{BF1}$, $S_{BF2}$, and $S_{BF3}$ of the user, the first reference time series is based on previous $S_{BF1}$, $S_{BF2}$, and $S_{BF3}$ taken while the user was in a normal state, and the second reference time series is based on previous $S_{BF1}$, $S_{BF2}$, and $S_{BF3}$ taken while the user was in an abnormal state. Optionally, the time series data and/or the first and second reference time series includes data taken over at least a certain period of time (e.g., at least ten seconds, at least one minute, or at least ten minutes).

Being in a normal/abnormal state may correspond to different behavioral and/or physiological responses. In one embodiment, the abnormal state involves the user displaying symptoms of one or more of the following: an anger attack, Attention Deficit Disorder (ADD), and Attention Deficit Hyperactivity Disorder (ADHD). In this embodiment, being in the normal state refers to usual behavior of the user that does not involve displaying said symptoms. In another embodiment, when the user is in the abnormal state, the user will display within a predetermined duration (e.g., shorter than an hour), with a probability above a predetermined threshold, symptoms of one or more of the following: anger, ADD, and ADHD. In this embodiment, when the user is in the normal state, the user will display the symptoms within the predetermined duration with a probability below the predetermined threshold. In yet another embodiment, when the user is in the abnormal state the user suffers from a headache and/or migraine (or an onset of a migraine attack will occur is a short time such as less than one hour), and when the user is in the normal state, the user does not suffer from a headache and/or a migraine. In still another embodiment, the abnormal state refers to times in which the user has a higher level of concentration compared to the normal state that refers to time in which the user has a usual level of concentration. Although the blood flow patterns of the forehead are usually specific to the user, they are usually repetitive, and thus the system may able to learn some blood flow patterns of the user that correspond to various states.

Determining the user's state based on $S_{BF1}$, $S_{BF2}$, and $S_{BF3}$ (and optionally other sources of data) may be done using a machine learning-based model. Optionally, the model is trained based on samples comprising feature values generated based on previous $S_{BF1}$, $S_{BF2}$, and $S_{BF3}$ taken when the user was in a known state (e.g., for different times it was known whether the user was in the normal or abnormal state). Optionally, the user may provide indications about his/her state at the time, such as by entering values via an app when having a headache, migraine, or an anger attack. Additionally or alternatively, an observer of the user, which may be another person or a software agent, may provide the indications about the user's state. For example, a parent may determine that certain behavior patterns of a child correspond to displaying symptomatic behavior of ADHD. In another example, indications of the state of the user may be determined based on measurements of physiological signals of the user, such as measurements of the heart rate, heart rate variability, breathing rate, galvanic skin response, and/or brain activity (e.g., using EEG). Optionally, the various indications described above are used to generate labels for the samples generated based on the previous $S_{BF1}$, $S_{BF2}$, and $S_{BF3}$.

In some embodiments, one or more of the feature values in the samples may be based on other sources of data (different from $S_{BF1}$, $S_{BF2}$, and $S_{BF3}$). These may include additional physiological measurements of the user and/or measurements of the environment in which the user was while $S_{BF1}$, $S_{BF2}$, and $S_{BF3}$ were taken. In one example, at least some of the feature values used in samples include additional physiological measurements indicative of one or more of the following signals of the user: heart rate, heart rate variability, brainwave activity, galvanic skin response, muscle activity, and extent of movement. In another example, at least some of the feature values used in samples include measurements of the environment that are indicative of one or more of the following values of the environment in which the user was in: temperature, humidity level, noise level, air quality, wind speed, and infrared radiation level.

Given a set of samples comprising feature values generated based on $S_{BF1}$, $S_{BF2}$, and $S_{BF3}$ (and optionally the other sources of data) and labels generated based on the indications, the model can be trained using various machine learning-based training algorithms. Optionally, the model is utilized by a classifier that classifies the user's state (e.g., normal/abnormal) based on feature values generated based on $S_{BF1}$, $S_{BF2}$, and $S_{BF3}$ (and optionally the other sources).

The model may include various types of parameters, depending on the type of training algorithm utilized to generate the model. For example, the model may include parameters of one or more of the following: a regression model, a support vector machine, a neural network, a graphical model, a decision tree, a random forest, and other models of other types of machine learning classification and/or prediction approaches.

In some embodiments, the model is trained utilizing deep learning algorithms. Optionally, the model includes parameters describing multiple hidden layers of a neural network. Optionally, the model includes a convolution neural network (CNN), which is useful for identifying certain patterns in images, such as patterns of color changes on the forehead. Optionally, the model may be utilized to identify a progression of a state of the user (e.g., a gradual forming of a certain blood flow pattern on the forehead). In such cases, the model may include parameters that describe an architecture that supports a capability of retaining state information. In one example, the model may include parameters of a recurrent neural network (RNN), which is a connectionist model that captures the dynamics of sequences of samples via cycles in the network's nodes. This enables RNNs to retain a state that can represent information from an arbitrarily long context window. In one example, the RNN may be implemented using a long short-term memory (LSTM) architecture. In another example, the RNN may be implemented using a bidirectional recurrent neural network architecture (BRNN).

In order to generate a model suitable for identifying the state of the user in real-world day-to-day situations, in some embodiments, the samples used to train the model are based on $S_{BF1}$, $S_{BF2}$, and $S_{BF3}$ (and optionally the other sources of data) taken while the user was in different situations, locations, and/or conducting different activities. In a first example, the model may be trained based on a first set of previous $S_{BF1}$, $S_{BF2}$, and $S_{BF3}$ taken while the user was indoors and in the normal state, a second set of previous $S_{BF1}$, $S_{BF2}$, and $S_{BF3}$ taken while the user was indoors and in the abnormal state, a third set of previous $S_{BF1}$, $S_{BF2}$, and $S_{BF3}$ taken while the user was outdoors and in the normal state, and a fourth set of previous $S_{BF1}$, $S_{BF2}$, and $S_{BF3}$ taken while the user was outdoors and in the abnormal state. In a second example, the model may be trained based on a first set of previous $S_{BF1}$, $S_{BF2}$, and $S_{BF3}$ taken while the user was sitting and in the normal state, a second set of previous $S_{BF1}$, $S_{BF2}$, and $S_{BF3}$ taken while the user was sitting and in the abnormal state, a third set of previous $S_{BF1}$, $S_{BF2}$, and $S_{BF3}$ taken while the user was standing and/or moving around and in the normal state, and a fourth set of previous $S_{BF1}$, $S_{BF2}$, and $S_{BF3}$ taken while the user was standing and/or moving around and in the abnormal state. Usually the movements while standing and/or moving around, and especially when walking or running, are greater compared to the movement while sitting; therefore, a model trained on samples taken during both sitting and standing and/or moving around is expected to perform better compared to a model trained on samples taken only while sitting.

Having the ability to determine the state of the user can be advantageous when it comes to scheduling tasks for the user and/or making recommendations for the user, which suits the user's state. In one embodiment, responsive to determining that the user is in the normal state, the computer prioritizes a first activity over a second activity, and responsive to determining that the user is in the abnormal state, the computer prioritizes the second activity over the first activity. Optionally, accomplishing each of the first and second activities requires at least a minute of the user's attention, and the second activity is more suitable for the abnormal state than the first activity. Optionally, and the first activity is more suitable for the normal state than the second activity. Optionally, prioritizing the first and second activities is performed by a calendar management program, a project management program, and/or a "to do" list program. Optionally, prioritizing a certain activity over another means one or more of the following: suggesting the certain activity before suggesting the other activity, suggesting the certain activity more frequently than the other activity (in the context of the specific state), allotting more time for the certain activity than for the other activity, and giving a more prominent reminder for the certain activity than for the other activity (e.g., an auditory indication vs. a mention in a calendar program that is visible only if the calendar program is opened).

Such state-dependent prioritization may be implemented in various scenarios. In one example, the normal state refers to a normal concentration level, the abnormal state refers to a lower than normal concentration level, and the first activity requires a high attention level from the user compared to the second activity. For instance, the first and second activities may relate to different topics of a self-learning program for school; when identifying that the user is in the normal concentration state, a math class is prioritized higher than a sports lesson; and when identifying that the user is in the lower concentration state, the math class is prioritized lower than the sports lesson. In another example, the normal state refers to a normal anger level, the abnormal state refers to a higher than normal anger level, and the first activity involves more interactions of the user with other humans compared to the second activity. In still another example, the normal state refers to a normal fear level, the abnormal state refers to a panic attack, and the second activity is expected to have a more relaxing effect on the user compared to the first activity.

Passively taken sensor based measurements may be used, in some embodiments, in order to detect whether a user exhibits stroke signs. However, in some scenarios, sensors that may be used to detect stroke signs may provide inaccurate signals that can lead to a high rate of false alarms. Detecting whether a user exhibits stroke signs can also be done by an app that prompts the user to perform one or more activities involved in a FAST test, and analyzing the user's actions while performing the one or more activities. However, apps for detecting stroke signs are often not used because the person suffering from a stroke is not aware of the incident (and thus does not initiate a test). Thus, the combination of the two approaches can increase the rate at which stroke signs may be detected based on possibly inaccurate measurements, by having the sensor measurements serve as a trigger to activate an app to prompt the user to perform the one or more activities involved in the FAST test.

In one embodiment, a system configured detect stroke signs includes at least first, second, and third sensors, and a computer. The first and second sensors configured to take first and second measurements ($M_R$ and $M_L$, respectively) of regions belonging to the right and left sides of a user's body. Optionally, $M_R$ and $M_L$ are indicative of blood flow in the regions on the right and left sides of the user's body, respectively. The following are examples of various types of sensors that may be used, in some embodiments, as the first and second sensors.

In one example, the first and second sensors are electroencephalography (EEG) electrodes that measure brain activity and are positioned on the right and left sides of the head, respectively. Optionally, the first and second sensors are I-J-G electrodes implanted under the user's scalp. In another example, the first and second sensors are electromyography (EMG) sensors implanted in the left and right sides of the user's body, respectively. Alternatively, the first and second sensors may be EMG sensors attached to the surface of the user's body. In yet another example, the first and second sensors may be ultrasound sensors. Optionally, the ultrasound sensors are positioned such that they are in contact with the surface of the right and left sides of the user's body respectively. In still another example, the first and second sensors are photoplethysmogram (PPG) sensors that provide measurements indicative of the blood flow on the right and left sides of the user's body, respectively. In yet another example, the first and second sensors comprise cameras based on a sensor comprising at least 3×3 pixels configured to detect electromagnetic radiation having wavelengths in at least a portion of the range of 200 nm to 1200 nm. In yet another example, the first and second sensors are thermistors in contact with the right and left sides of the user's body. For example, the first and second sensors may be embedded in one or more of the following: a clothing item worn by the user, gloves, or a scarf. And in still another example, the first and second sensors are thermal cameras each comprising at least 3×3 pixels configured to detect electromagnetic radiation having wavelengths above 2500 nm.

The computer calculates, based on $M_R$ and $M_L$, a value indicative of a risk that the user has suffered from a stroke. Responsive to determining that the value reaches a threshold, the computer may instruct the user, via a user interface, to perform the predetermined activity. The computer may then detect whether the user exhibits stroke signs based on measurements ($M_A$) of a third sensor, which were taken while the user performed the predetermined activity. Optionally, the computer utilizes $M_R$ and $M_L$ along with $M_A$ in order to make a more accurate detection of stroke signs. Optionally, detection based on $M_R$, $M_L$, and $M_A$ is more accurate than detection based on $M_R$ alone $M_L$.

Calculating the value indicative of the risk that the user has suffered from a stroke may be done in different ways in different embodiments. In one embodiment, the value indicative of the risk is indicative difference between of extents of physiological changes in the right and left sides of the body, which are calculated based on $M_R$ and $M_L$, respectively. For example, the value may be indicative of a difference in blood flow between the right and left sides of the body, a difference in the temperature between the right and left sides, and/or a difference in skin color and/or extent of changes to skin color between the right and left sides. Optionally, when the difference reaches the threshold, this means that the user is at a risk of having suffered a stroke that is sufficiently high to warrant an additional test that involves performing the predetermined activity and measuring the user with the third sensor.

In another embodiment, the computer generates feature values based on $M_R$ and $M_L$ and utilizes a model to calculate, based on the feature values, the value indicative of the risk that the user has suffered from a stroke. Optionally, the model is generated based on previous $M_R$ and $M_L$ of multiple users. For example, the model may be generated based on data that comprises $M_R$ and $M_L$ of users who were healthy at the time the measurements were taken, and also based on $M_R$ and $M_L$ of users who suffered from a stroke while the measurements were taken.

There are various predetermined activities the computer may prompt the user to perform in order to detect whether the user exhibits stroke signs. These activities may be measured using different sensors. The following are examples of combinations of activities, and sensors that may be used to take the measurements $M_A$ of the user while the user performs the activities.

In one embodiment, performing the predetermined activity comprises smiling. Optionally, in this embodiment, the third sensor is a camera. For example, the camera may be a camera embedded in a cell phone (or some other device) held by the user or some other person. In another example, the camera may be coupled to a frame worn on the user's head. In this embodiment, $M_A$ include images of the user's face that capture the user's facial expressions while the user was instructed to smile. The computer may detect the stroke signs based on analysis of images of the user which are indicative of one side of the face drooping. Optionally, the analysis involves comparing $M_A$ to previously taken images of the user's face.

In another embodiment, performing the predetermined activity comprises raising both arms. Optionally, in this embodiment, the third sensor is an inertial measurement unit (IMU). For example, the IMU may be embedded in a cell phone, a smart watch, or another device on worn or held by the user (e.g., on the hand, wrist, or arm). In this embodiment, the computer detects the stroke signs based on analysis of measurements of movements of the user (taken by the IMU) which are indicative of one arm drifting downward.

In yet another embodiment, performing the predetermined activity comprises walking. Optionally, in this embodiment, the third sensor is an inertial measurement unit (IMU). For example, the IMU may be coupled to a frame worn on the user's head or in a device carried by the user (e.g., a smartphone or a smartwatch). In this embodiment, computer detects the stroke signs based on analysis measurements of movements of the user (taken by the IMU) which are indicative of imbalance of the user.

In still another embodiment, performing the predetermined activity comprises repeating a phrase. Optionally, in this embodiment, the third sensor is a microphone. For example, the microphone may belong to a device carried or worn by the user (e.g., a smartphone, a smartwatch, or microphone embedded in a head-mounted display). In this embodiment, computer detects the stroke signs based on analysis of a recording of voice of the user which is indicative of the user's speech being slurry. Optionally, the analysis of the recording of the user's voice is done based on a comparison with previous recordings of the user's voice.

In some embodiments, the computer may conduct tests to determine whether the user's brain function has been affected. For example, the computer may prompt the user to perform various tasks using an app that can test for memory and cognitive skills, such as answering trivia questions, solving puzzles, etc.

In some embodiments, following the user's performance of the predetermined activity and analysis of $M_A$, results of the analysis may be used to improve the accuracy of the calculation of the risk. For example, responsive to determining, based on specific $M_A$, that the user does not exhibit stroke signs after measuring specific $M_R$ and $M_L$ values (which indicated that there is sufficient risk), the computer is configured to adjust the threshold based on the specific $M_R$ and $M_L$ values. In another example, the computer may utilize the specific $M_R$ and $M_L$ to retrain a model used to calculate the risk. In this example, the specific $M_R$ and $M_L$ can constitute an example of a false positive that is used to adjust the model parameters.

One of the signs to having a stroke is sudden loss of balance or coordination. It is easier to identify loss of balance or coordination from measurements taken by a head-mounted IMU compared to measurements taken by an IMU inside a wrist band or a phone in the hand. The reason is that the movements of the head include much less noise compared to movements of a hand that is used to manipulate items. Therefore, a head-mounted IMU can be more beneficial for identifying loss of balance or coordination than a wrist-mounted IMU.

In one embodiment, a system configured to detect a medical condition, which involves a loss of at least one of balance and coordination, includes at least a head-mounted inertial measurement unit (IMU) and a computer. Some examples of medical conditions that involve loss of balance and/or coordination include a stroke and a spell of dizziness. The IMU is configured to measure movements of the head of a user wearing the IMU, and a computer. Optionally, the IMU comprises at least one of the following elements: an accelerometer, a gyroscope, and a magnetometer. Optionally, the IMU is coupled to a frame worn on the user's head. The computer is configured to detect the medical condition based on measurements of the IMU ($M_{current}$) and previous measurements of movements of the head of the user wearing the IMU ($M_{previous}$). Optionally, at least some of $M_{previous}$ were taken while the user did not have the medical condition. Optionally, the computer is further configured to alert a predetermined recipient (e.g., a caregiver or emergency services) responsive to detecting the medical condition.

There are various ways in which the medical condition may be detected based on $M_{current}$ and $M_{previous}$. In one embodiment, the computer is configured to detect the medical condition by calculating a difference between movement characteristics determined based on $M_{current}$ and typical movement characteristics of the user calculated based on $M_{previous}$. Optionally, if the difference reaches a threshold, the user is considered to have the medical condition. In another embodiment, the computer is configured to detect the medical condition by generating feature values and utilizing a model to calculate a value, based on the feature values, which is indicative of whether the user has the medical condition. Optionally, one or more of the feature values are calculated based on $M_{current}$ and the model is generated based $M_{previous}$ the user. In yet another embodiment, the computer is configured to detect the medical condition by generating feature values and utilizing a model to calculate a value, based on the feature values, which is indicative of whether the user has the medical condition. Optionally, one or more of the feature values are calculated based on movements of the head of one or more other users wearing an IMU.

The user's movement characteristics may be affected by various factors, as discussed below. Thus, receiving an indication of such factors that influence movement and balance can help improve accuracy of detecting the medical condition based on $M_{current}$ and $M_{previous}$. In some embodiments, the computer is further configured to receive an indication of a situation in which the user is in while $M_{current}$ are taken, and to utilise the indication to detect the medical condition.

In one embodiment, the situation comprises being under influence of a medication, and the indication of the situation is received from at least one of: a pill dispenser, a sensor-enabled pill, and a user tracking application. Examples of user tracking applications include: (i) software that requires a user to log events, such as consumption of a certain item, usage of a certain item, having a certain experience, and/or being in a certain situation, (ii) an image analysis software that receives images taken by the user or a third party nearby the user, and infers the situation from the images using image processing techniques. Examples of sources for the image include: smartglasses with outfacing camera, augmented reality devices, mobile phones, and webcams.

In another one embodiment, the situation comprises being under influence of at least one of alcohol and caffeine, and the indication of the situation is received from at least one of: a refrigerator, a pantry, a serving robot, and a user tracking application; and wherein the indication indicates that the user took an alcoholic beverage. In yet another embodiment, the situation comprises being under a certain stress level, and the indication of the situation is received from a sensor that measures a physiological signal of the user, such as a thermal sensor, a heart rate sensor, a sensor of galvanic skin response, or an EEG sensor. In still another embodiment, the situation is selected from a group comprising: being inside a moving vehicle, and being on a static floor, and the indication of the situation is received from a positioning system. Examples of positioning systems include: GPS, wireless positioning systems, image processing to infer position.

Typically having a stroke will influence brain activity, which can be detected through electroencephalography (EEG). However, this signal may at times be noisy and insufficient to reliably detect a stroke. Thus, additional tests may be needed. In one embodiment, a system configured to detect stroke signs based on electroencephalography (EEG) includes at least a sensor configured to take measurements ($M_A$) of the user, and a computer. The computer is configured to: receive EEG signals of the user, and to utilize a model to calculate, based on the EEG signals, a value indicative of a risk that the user has suffered from a stroke. The value indicative of the risk is compared by the computer to a threshold, and responsive to determining that the value reaches a threshold, the computer instructs the user, via a user interface, to perform a predetermined activity. The computer then detects whether the user has stroke signs based on $M_A$ taken while the user performed the predetermined activity. Optionally, the computer utilizes the EEG signals along with $M_A$ in order to make a more accurate detection of stroke signs. Optionally, detection based on the EEG signals and $M_A$ is more accurate than detection based on the EEG signals alone.

Calculating the value indicative of the risk that the user has suffered from a stroke may be done in different ways in different embodiments. In one embodiment, the value indicative of the risk is indicative difference between of extents of electrical potential changes in the right and left sides of the brain, which are calculated based on EEG signals from electrodes on the right and left sides of the head. Optionally, when the difference reaches the threshold, this means that the user is at a risk of having suffered a stroke that is sufficiently high to warrant an additional test that involves performing the predetermined activity and measuring the user with the third sensor.

In another embodiment, the computer generates feature values based on the EEG signals and utilizes a model to calculate, based on the feature values, the value indicative of the risk that the user has suffered from a stroke. Optionally, the model is generated based on previous EEG signals of multiple users. For example, the model may be generated based on data that comprises I-J-G signals of users who were healthy at the time the measurements were taken, and also based on EEG signals of users who suffered from a stroke while the measurements were taken.

There are various predetermined activities the computer may prompt the user to perform in order to detect whether the user exhibits stroke signs. These activities may be measured using different sensors. Examples of combinations of activities, and sensors that may be used to take the measurements $M_A$ of the user while the user performs the activities are given above (e.g., smiling, raising hands, walking, and speaking a phrase).

In some embodiments, following the user's performance of the predetermined activity and analysis of $M_A$ results of the analysis may be used to improve the accuracy of the calculation of the risk. For example, responsive to determining, based on specific $M_A$, that the user does not exhibit stroke signs after measuring specific EEG signals values (which indicated that there is sufficient risk), the computer is configured to adjust the threshold based on the specific EEG signals. In another example, the computer may utilize the specific EEG signals to retrain a model used to calculate the risk. In this example, the specific EEG signals can constitute an example of a false positive that is used to adjust the model parameters.

US Patent Application 2019/0223737A1, which is herein incorporated by reference in its entirety and is a previous patent application of the Applicant of this invention, discusses and illustrates in paragraphs 0040-0049, together with their associated drawings, various examples of head-mounted systems equipped with head-mounted cameras, which can be adapted to be utilized with some of the embodiments herein. For example, these paragraphs illustrate various inward-facing head-mounted cameras coupled to an eyeglasses frame, illustrate cameras that capture regions on the periorbital areas, illustrate an optional computer that may include a processor, memory, a battery and/or a communication module, illustrate inward-facing head-mounted cameras coupled to an augmented reality devices, illustrate head-mounted cameras coupled to a virtual reality device, illustrate head-mounted cameras coupled to a sunglasses frame, illustrate cameras configured to capture various ROIs, such as the forehead, the upper lip, the cheeks, and sides of the nose, illustrate inward-facing head-mounted cameras mounted to protruding arms, illustrate various inward-facing head-mounted cameras having multi-pixel sensors (FPA sensors) configured to capture various ROIs, illustrate head-mounted cameras that are physically coupled to a frame using a clip-on device configured to be attached/detached from a pair of eyeglasses in order to secure/release the device to/from the eyeglasses, illustrate a clip-on device holds at least an inward-facing camera, a processor, a battery, and a wireless communication module, illustrate right and left clip-on devices configured to be attached behind an eyeglasses frame, illustrate a single-unit clip-on device configured to be attached behind an eyeglasses frame, and illustrate right and left clip-on devices configured to be attached/detached from an eyeglasses frame and having protruding arms to hold the inward-facing head-mounted cameras.

It is noted that the elliptic and other shapes of the ROIs in some of the drawings are just for illustration purposes, and the actual shapes of the ROIs are usually not as illustrated. It is possible to calculate the accurate shape of an ROI using various methods, such as a computerized simulation using a 3D model of the face and a model of a head-mounted system (HMS) to which a camera is physically coupled, and/or by placing a LED instead of the sensor, while maintaining the same field of view (FOV) and observing the illumination pattern on the face, and/or by analyzing the image captured by the camera (when its resolution is high enough). Furthermore, illustrations and discussions of a camera represent one or more cameras, where each camera may have the same FOV and/or different FOVs. Unless indicated to the contrary, the cameras may include one or more sensing elements (pixels), even when multiple sensing elements do not explicitly appear in the figures or explicitly mentioned in the text; when a camera includes multiple sensing elements then the illustrated ROI usually refers to the total ROI captured by the camera, which is made of multiple regions that are respectively captured by the different sensing elements. The positions of the cameras in the figures are just for illustration, and the cameras may be placed at other positions on the HMS.

Sentences in the form of an "ROI on an area", such as ROI on the forehead or an ROI on the nose, refer to at least a portion of the area. Depending on the context, and especially when using a camera having a small number of pixels, the ROI may cover another area (in addition to the area). For example, a sentence in the form of "an ROI on the nose" may refer to either: 100% of the ROI is on the nose, or some of the ROI is on the nose and some of the ROI is on the upper lip.

In various embodiments, cameras are located close to a user's face, such as at most 2 cm, 5 cm, 10 cm, 15 cm, or 20 cm from the face. The distance from the face/head in sentences such as "a camera located less than 10 cm from the face/head" refers to the shortest possible distance between the camera and the face/head. The head-mounted cameras used in various embodiments may be lightweight, such that each camera weighs below 10 g, 5 g, 1 g, and/or 0.5 g (herein "g" denotes to grams).

In some embodiments, a device, such as a camera, may be positioned such that it occludes an ROI on the user's face, while in other embodiments, the device may be positioned such that it does not occlude the ROI. Non-limiting examples of occluding and non-occluding systems, which can be adapted to be utilized with some of the embodiments herein, are described in paragraph 0034 and its associated drawings in US Patent Application 2019/0223737A1.

Some of the embodiments herein may utilize the Scheimpflug principle, which is a known geometric rule that describes the orientation of the plane of focus of a camera when the lens plane is tilted relative to the sensor plane. US Patent Application 2019/0223737A1 discusses and illustrates in paragraphs 0097-0105, together with their associated drawings, various embodiments of the Scheimpflug principle, which can be adapted to be utilized with some of the embodiments herein. For example, these paragraphs discuss selecting the tilt between the lens plane and the sensor plane such as to adjust the sharpness of the various areas covered in the ROI according to their importance for detecting the user's physiological signals, discuss a fixed tilt between the lens plane and sensor plane, and discuss an adjustable electromechanical tilting mechanism.

Various embodiments described herein involve an HMS that may be connected, using wires and/or wirelessly, with a device carried by the user and/or a non-wearable device. The HMS may include a battery, a computer, sensors, and a transceiver.

FIG. 23a and FIG. 23b are schematic illustrations of possible embodiments for computers (400, 410) that are able to realize one or more of the embodiments discussed herein that include a "computer". The computer (400, 410) may be implemented in various ways, such as, but not limited to, a microcontroller, a computer on a chip, a system-on-chip (SoC), a system-on-module (SoM), a processor with its required peripherals, a server computer, a client computer, a personal computer, a cloud computer, a network device, a handheld device (e.g., a smartphone), an head-mounted system (such as smartglasses, an augmented reality system, a virtual reality system, and/or a smart-helmet), a computing device embedded in a wearable device (e.g., a smartwatch or a computer embedded in clothing), a computing device implanted in the human body, and/or any other computer form capable of executing a set of computer instructions. Further, references to a computer or a processor include any collection of one or more computers and/or processors (which may be at different locations) that individually or jointly execute one or more sets of computer instructions. This means that the singular term "computer" is intended to imply one or more computers, which jointly perform the functions attributed to "the computer". In particular, some functions attributed to the computer may be performed by a computer on a wearable device (e.g., smartglasses) and/or a computer of the user (e.g., smartphone), while other functions may be performed on a remote computer, such as a cloud-based server.

The computer 400 includes one or more of the following components: processor 401, memory 402, computer readable medium 403, user interface 404, communication interface 405, and bus 406. The computer 410 includes one or more of the following components: processor 411, memory 412, and communication interface 413.

Functionality of various embodiments may be implemented in hardware, software, firmware, or any combination thereof. If implemented at least in part in software, implementing the functionality may involve a computer program that includes one or more instructions or code stored or transmitted on a computer-readable medium and executed by one or more processors. Computer-readable media may include computer-readable storage media, which corresponds to a tangible medium such as data storage media, and/or communication media including any medium that facilitates transfer of a computer program from one place to another. Computer-readable medium may be any media that can be accessed by one or more computers to retrieve instructions, code, data, and/or data structures for implementation of the described embodiments. A computer program product may include a computer-readable medium. In one example, the computer-readable medium 403 may include one or more of the following: RAM, ROM, EEPROM, optical storage, magnetic storage, biologic storage, flash memory, or any other medium that can store computer readable data.

A computer program (also known as a program, software, software application, script, program code, or code) can be written in any form of programming language, including compiled or interpreted languages, declarative or procedural languages. The program can be deployed in any form, including as a standalone program or as a module, component, subroutine, object, or another unit suitable for use in a computing environment. A computer program may correspond to a file in a file system, may be stored in a portion of a file that holds other programs or data, and/or may be stored in one or more files that may be dedicated to the program. A computer program may be deployed to be executed on one or more computers that are located at one or more sites that may be interconnected by a communication network.

Computer-readable medium may include a single medium and/or multiple media (e.g., a centralized or distributed database, and/or associated caches and servers) that store one or more sets of instructions. In various embodiments, a computer program, and/or portions of a computer program, may be stored on a non transitory computer-readable medium, and may be updated and/or downloaded via a communication network, such as the Internet. Optionally, the computer program may be downloaded from a central repository, such as Apple App Store and/or Google Play. Optionally, the computer program may be downloaded from a repository, such as an open source and/or community run repository (e.g., GitHub).

At least some of the methods described herein are "computer-implemented methods" that are implemented on a computer, such as the computer (400, 410), by executing instructions on the processor (401, 411). Additionally, at least some of these instructions may be stored on a non transitory computer-readable medium.

As used herein, references to "one embodiment" (and its variations) mean that the feature being referred to may be included in at least one embodiment of the invention. Moreover, separate references to "one embodiment", "some embodiments", "another embodiment", "still another embodiment", etc., may refer to the same embodiment, may illustrate different aspects of an embodiment, and/or may refer to different embodiments.

Some embodiments may be described using the verb "indicating", the adjective "indicative", and/or using variations thereof. Herein, sentences in the form of "X is indicative of Y" mean that X includes information correlated with Y, up to the case where X equals Y. Stating that "X indicates Y" or "X indicating Y" may be interpreted as "X being indicative of Y". Additionally, sentences in the form of "provide/receive an indication indicating whether X happened" may refer to any indication method, including but not limited to: sending/receiving a signal when X happened and not sending/receiving a signal when X did not happen, not sending/receiving a signal when X happened and sending/receiving a signal when X did not happen, and/or sending/receiving a first signal when X happened and sending/receiving a second signal X did not happen.

Herein, "most" of something is defined as above 51% of the something (including 100% of the something). Both a "portion" of something and a "region" of something refer to a value between a fraction of the something and 100% of the something. For example, sentences in the form of a "portion of an area" may cover between 0.1% and 100% of the area. As another example, sentences in the form of a "region on the user's forehead" may cover between the smallest area captured by a single pixel (such as 0.1% or 5% of the forehead) and 100% of the forehead. The word "region" refers to an open-ended claim language, and a camera said to capture a specific region on the face may capture just a small part of the specific region, the entire specific region, and/or a portion of the specific region together with additional region(s).

The terms "comprises", "comprising", "includes", "including", "has", "having", or any other variation thereof, indicate an open-ended claim language that can include additional limitations. The "a" or "an" is employed to describe one or more, and the singular also includes the plural unless it is obvious that it is meant otherwise. For example, "a computer" refers to one or more computers, such as a combination of a wearable computer that operates together with a cloud computer.

The phrase "based on" indicates an open-ended claim language, and is to be interpreted as "based, at least in part, on". Additionally, stating that a value is calculated "based on X" and following that, in a certain embodiment, that the value is calculated "also based on Y", means that in the certain embodiment, the value is calculated based on X and Y. Variations of the terms "utilize" and "use" indicate an open-ended claim language, such that sentences in the form of "detecting X utilizing Y" are intended to mean "detecting X utilizing at least Y", and sentences in the form of "use X to calculate Y" are intended to mean "calculate Y based on X".

The terms "first", "second" and so forth are to be interpreted merely as ordinal designations, and shall not be limited in themselves. A predetermined value is a fixed value and/or a value determined any time before performing a calculation that compares a certain value with the predetermined value. A value is also considered to be a predetermined value when the logic, used to determine whether a threshold that utilizes the value is reached, is known before start performing computations to determine whether the threshold is reached.

The embodiments of the invention may include any variety of combinations and/or integrations of the features of the embodiments described herein. Although some embodiments may depict serial operations, the embodiments may perform certain operations in parallel and/or in different orders from those depicted. Moreover, the use of repeated reference numerals and/or letters in the text and/or drawings is for the purpose of simplicity and clarity and does not in itself dictate a relationship between the various embodiments and/or configurations discussed. The embodiments are not limited in their applications to the order of steps of the methods, or to details of implementation of the devices, set in the description, drawings, or examples. Moreover, individual blocks illustrated in the figures may be functional in nature and therefore may not necessarily correspond to discrete hardware elements.

Certain features of the embodiments, which may have been, for clarity, described in the context of separate embodiments, may also be provided in various combinations in a single embodiment. Conversely, various features of the embodiments, which may have been, for brevity, described in the context of a single embodiment, may also be provided separately or in any suitable sub-combination. Embodiments described in conjunction with specific examples are presented by way of example, and not limitation. Moreover, it is evident that many alternatives, modifications, and variations will be apparent to those skilled in the art. It is to be understood that other embodiments may be utilized and structural changes may be made without departing from the scope of the embodiments. Accordingly, this disclosure is intended to embrace all such alternatives, modifications, and variations that fall within the spirit and scope of the appended claims and their equivalents.

We claim:

1. A system configured to detect fever, comprising:
a head-mounted inward-facing non-contact thermal camera configured to measure skin temperature ($T_{skin}$) at a first region on a user's head;
a head-mounted temperature sensor configured to measure temperature of the environment ($T_{env}$);
a head-mounted camera sensitive to wavelengths below 1050 nanometer, configured to capture images of e second region on the user's face; and
a computer configured to:
calculate, based on the images, values indicative of hemoglobin concentrations at three or more regions on the user's face; and
detect whether the user has a fever based on $T_{skin}$, $T_{env}$, and the values indicative of hemoglobin concentrations.

2. The system of claim 1, wherein the first region covers a portion of skin that is not located above a portion of a branch of the external carotid artery, and the computer is configured to perform the detection of whether the user has the fever by (i) generating feature values based on: $T_{skin}$, $T_{env}$, and the values indicative of hemoglobin concentrations, and (ii) utilizing a machine learning-based model to calculate, based on the feature values, a values indicative of whether the user has the fever.

3. The system of claim 1, wherein the head-mounted inward-facing non-contact thermal camera is located more than 2 mm away from the user's head, the second region is larger than 2 cm², and the head-mounted camera sensitive to wavelengths below 1050 nanometer is an inward-facing head-mounted camera configured to capture the images from a distance between 5 mm and 5 cm from the user's head.

4. The system of claim 1, wherein the computer is further configured to utilize one or more calibration measurements of the user's core body temperature, taken by a thermometer that is not the head-mounted inward-facing non-contact thermal camera: or the head-mounted temperature sensor, to calibrate a model, and to utilize said calibrated model, to calculate the user's core body temperature based on $T_{skin}$, $T_{env}$ and the values; and the computer is further configured to share fever history of the user upon receiving a permission from the user.

5. The system of claim 1, wherein the computer is further configured to extract imaging photoplethysmogram signals from the image and to calculate the values indicative of hemoglobin concentrations based on the imaging photoplethysmogram signals: and the computer is further configured to utilize one or more calibration measurements of the user's core body temperature, taken by a thermometer that is not the head-mounted inward-facing non-contact thermal camera or the head-mounted temperature sensor, prior to a certain time, and to calculate the user's core body temperature based on $T_{skin}$, $T_{env}$, which were taken after the certain time, and the values indicative of the hemoglobin concentrations detected in the images that were taken after the certain time.

6. The system of claim 1, further comprising a head-mounted acoustic sensor configured to take audio recordings of the user, and a head-mounted movement sensor configured to measure a signal indicative of movements of the user's head (head-movement signal); wherein the computer is further configured to: (i) generate feature values based on $T_{skin}$, $T_{env}$, the values indicative of hemoglobin concentrations, the audio recordings, and the head-movement signal, and (ii) utilize a machine learning-based model to calculate, based on the feature values, a level of dehydration of the user.

7. The system of claim 6, wherein, for generating the feature values based on the audio recordings, the computer is further configured to extract features indicative of the user's respiratory rate and vocal changes; whereby dehydration is associated with an increase in the respiratory rate and a decrease in the speed quotient at low-pitch phonation.

8. The system of claim 1, further comprising a head-mounted acoustic sensor configured to take audio recordings of the user; wherein the detection of whether the user has the fever comprises the computer performing the following: (i) generating feature values based on $T_{skin}$, $T_{env}$, the values indicative of hemoglobin concentrations, and the audio recordings, and (ii) utilizing a machine learning-based model to calculate, based on the feature values, a value indicative of whether the user has the fever; and wherein one or more of the feature values, which were generated based on the audio recordings, are indicative of the user's respiration rate.

9. The system of claim 1, further comprising a head-mounted movement sensor configured to measure a signal indicative of movements of the user's head (head-movement signal); wherein the detection of whether the user has the fever comprises the computer performing the following: (i) generating feature values based on $T_{skin}$, $_{env}$, the values indicative of hemoglobin concentrations, and the head-movement signal, and (ii) utilizing a machine learning-based model to calculate, based on the feature values, a value indicative of whether the user has the fever; and wherein one or more of the feature values, which were generated based on the head-movement signal are indicative of the user's physical activity level.

10. The system of claim 1, further comprising a head-mounted anemometer configured to measure a signal indicative of wind speed hitting the user's head (wind signal), and a head-mounted hygrometer configured to measure a signal indicative of humidity (humidity signal); wherein the detection of whether the user has the fever comprises the computer performing the following: (i) generating feature values based on $T_{skin}$, $T_{env}$, the values indicative of hemoglobin concentrations, the wind signal, and the humidity signal, and (ii) utilizing a machine learning-based model to calculate, based on the feature values, a value indicative of whether the user has the fever.

11. The system of claim 1, further comprising an helmet or goggles configured to be worn on the user's head, the head-mounted inward-facing non-contact thermal camera is physically coupled to the helmet or goggles, and the first region is located on the user's forehead, cheekbone, or temple.

12. The system of claim 1, further comprising an eyeglasses frame configured to be worn on the user's head, the head-mounted inward-facing non-contact thermal camera is physically coupled to the frame, and the first region is located on the user's nose or temple; and wherein the computer is further configured to: calculate, based on additional images captured with the head-mounted camera sensitive to wavelengths below 1050 nanometer while the user had a fever, additional values indicative of hemoglobin concentrations at the three or more regions on the user's face while the user had the fever, and base the detection of whether the user has the fever also on a deviation of the values from the additional values.

13. The system of claim 1, wherein the images comprise a first channel corresponding to wavelengths that are mostly below 580 nanometers and a second channel corresponding to wavelengths mostly above 580 nanometers; and wherein the values indicative of hemoglobin concentrations comprise: (i) first values derived based on the first channel in the images, and (ii) second values derived based on the second channel in the images.

14. The system of claim 1, further comprising at least one sensor selected from among the following sensors: a head-mounted acoustic sensor configured to take audio recordings of the user, a head-mounted movement sensor configured to measure a signal indicative of movements of the user's head, a head-mounted anemometer configured to measure a signal indicative of wind speed hitting the user's head, and a head-mounted hygrometer configured to measure a signal indicative of humidity; wherein the computer is further configured to: (i) generate feature values based on $T_{skin}$, $T_{env}$, the values indicative of hemoglobin concentrations, measurements taken with the at least one sensor, and (ii) utilize a machine learning-based model to calculate, based on the feature values, a value indicative of the core body temperature of the user.

15. A method for detecting fever, comprising:
receiving, from a head-mounted inward-facing non-contact thermal camera, measurements of skin temperature ($T_{skin}$) at a first region on a user's head;
receiving, from a head-mounted temperature sensor, measurements of temperature of the environment ($T_{env}$);
receiving, from a head-mounted camera sensitive to wavelengths below 1050 nanometer, images of a second region on the user's face;
calculating, based on the images, values indicative of hemoglobin concentrations at three or more regions on the user's face; and
detecting whether the user has a fever based on $T_{skin}$, $T_{env}$, and the values indicative of hemoglobin concentrations.

16. The method of claim 15, wherein the first region covers a portion of skin that is not located above a portion of a branch of the external carotid artery, and the detecting of whether the user has the fever comprises (i) generating feature values based on: $T_{skin}$, $T_{env}$, and the values indicative of hemoglobin concentrations, and (ii) utilizing a machine learning-based model to calculate, based on the feature values, a values indicative of whether the user has the fever.

17. The method of claim 15, further comprising: utilizing one or more calibration measurements of the user's core body temperature, taken by a different device, to calibrate a model, and utilizing said calibrated model to calculate the user's core body temperature based on $T_{skin}$, $T_{env}$, and the values indicative of hemoglobin concentrations.

18. A non-transitory computer readable medium storing one or more computer programs configured to cause a processor based system to execute steps comprising:
receiving, from a head-mounted inward-facing non-contact thermal camera, measurements of skin temperature ($T_{skin}$) at a first region on a user's head;
receiving, from a head-mounted temperature sensor, measurements of temperature of the environment ($T_{env}$);
receiving, from a head-mounted camera sensitive to wavelengths below 1050 nanometer, images of a second region on the user's face;
calculating, based on the images, values indicative of hemoglobin concentrations at three or more regions on the user's face; and
detecting whether the user has a fever based on $T_{skin}$, $T_{env}$, and the values indicative of hemoglobin concentrations.

19. The non-transitory computer readable medium of claim 18, further comprising instructions for execution of the following steps involved in detecting whether the user has the fever: (i) generating feature values based on: $T_{skin}$, $T_{env}$, and the values indicative of hemoglobin concentrations, and (ii) utilizing a machine learning-based model to calculate, based on the feature values, a values indicative of whether the user has the fever.

20. The non-transitory computer readable medium of claim 18, further comprising instructions for execution of the following steps: utilizing one or more calibration measurements of the user's core body temperature, taken by a different device, to calibrate a model, and utilizing said calibrated model to calculate the user's core body temperature based on $T_{skin}$, $T_{env}$, and the values indicative of hemoglobin concentrations.

\* \* \* \* \*